US006713300B1

(12) United States Patent
Allikmets et al.

(10) Patent No.: US 6,713,300 B1
(45) Date of Patent: Mar. 30, 2004

(54) NUCLEIC ACID AND AMINO ACID SEQUENCES FOR ATP-BINDING CASSETTE TRANSPORTER AND METHODS OF SCREENING FOR AGENTS THAT MODIFY ATP-BINDING CASSETTE TRANSPORTER

(75) Inventors: Rando Allikmets, Frederick, MD (US); Kent L. Anderson, Houston, TX (US); Michael Dean, Frederick, MD (US); Mark Leppert, Salt Lake City, UT (US); Richard A. Lewis, Houston, TX (US); Yixin Li, Houston, TX (US); James R. Lupski, Houston, TX (US); Jeremy Nathans, Baltimore, MD (US); Amir Rattner, Baltimore, MD (US); Noah F. Shroyer, Houston, TX (US); Nanda Singh, Salt Lake City, UT (US); Philip Smallwood, Woodbine, MD (US); Hui Sun, Baltimore, MD (US)

(73) Assignees: University of Utah Research Foundation, Salt Lake City, UT (US); Baylor College of Medicine, Houston, TX (US); Johns Hopkins University, Baltimore, MD (US); The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/032,438

(22) Filed: Feb. 27, 1998

Related U.S. Application Data

(60) Provisional application No. 60/039,388, filed on Feb. 27, 1997.

(51) Int. Cl.[7] .......................... C12N 15/00; C12N 5/00; C12N 15/63; C07H 21/62; C07H 21/04
(52) U.S. Cl. .................. 435/325; 435/69.1; 435/320.1; 435/455; 536/23.1; 536/23.5
(58) Field of Search .............................. 435/69.1, 70.1, 435/70.3, 71.1, 320.1, 325, 455; 536/23.1, 23.5; 514/44

(56) References Cited

U.S. PATENT DOCUMENTS

| 4,683,195 A | 7/1987 | Mullis et al. ................... 435/6 |
| 4,683,202 A | 7/1987 | Mullis .......................... 435/91 |
| 4,800,159 A | 1/1989 | Mullis et al. ............. 435/172.3 |
| 4,883,750 A | 11/1989 | Whiteley et al. ............... 435/6 |
| 5,489,519 A * | 2/1996 | Deeley et al. .............. 435/69.1 |

FOREIGN PATENT DOCUMENTS

| EP | 329 822 | 6/1994 |
| GB | 2 202 328 | 9/1988 |
| WO | WO 87/06270 | 11/1987 |
| WO | WO 88/10315 | 12/1988 |
| WO | WO 89/06700 | 7/1989 |
| WO | PCT/US89/01025 | 10/1989 |

OTHER PUBLICATIONS

Ledley, F.D., Pharmaceutical Research, 13:1595–1614, 1996.*
Verma et al., Nature, 389:239–242, 1997.*
Orkin et al., in "Report And Recommendations Of The Panel To Assess The NIH Investment In Research On Gene Therapy", Dec. 7, pp. 1–41, 1996.*
Allikmets, R. et al., "A Photoreceptor cell–specific ATP–binding Transporter Gene (ABCR) is mutated in recessive Stargardt macular dystrophy", *Nature Genetics*, 1997, 15, 236–246.
Allikmets, R. et al., "Mutation of the Stargardt Disease Gene (ABCR) in Age–Related Macular Degeneration", *Science*, 1997, 277, 1805–1807.
Allikmets, R. et al., "Characterization of the human ABC superfamily: isolation an dmapping of 21 new genes using the Expressed Sequence Tags database", *Hum. Mol. Genet.*, 1996, 5, 1649–1655.
Allikmets, R. et al., "Charactization and mapping of three new mammalian ATP–binding transporter genes from an EST database", *Mam. Genome*, 1995, 6, 114–117.
Allikmets, R. et al., "Cloning and organization of the abc and mdl genes of *Escherichia coli*: relationship to eukaryotic multidrug resistance", *Gene*, 1993, 136, 231–236.
Altschul, S.F. et al., "Basic Local Alignment Search Tool", *J. Mol. Biol.*, 1990, 215, 403–410.
Anderson, K.L., "Towards the Isolation of Genes for Recessively Inherited Ocular Disorders; Bardet–Biedl Syndrome, Leber Congenital Amaurosis, Primary Congenital Glaucoma, and Stargardt Disease", *Ph.D. Thesis, Baylor College of Medicine*, Jul. 30, 1996 (abstract).
Anderson, R.E. et al., "Lipids of Ocular Tissues", *Arch. Biochem. Biophys.*, 1971, 151, 270–276.
Azarian, S.M. et al., "The photoreceptor rim protein is an ABC transporter encoded by the gene for recessive Stargardt's disease (ABCR)", *FEBS Letts.*, 1997, 409, 247–252.
Bellanne–Chantelot, C. et al., "Mapping the Whole Human Genome by Fingerprinting Yeast Artificial Chromosomes", *Cell*, 1992, 70, 1059–1068.
Birnbach, C.D. et al, "Histopathology and Immunocytochemistry of the Neurosensory Retina in Fundus Flavimaculatus", *Ophthalmology*, 1994, 101, 1211–1219.

(List continued on next page.)

*Primary Examiner*—Jeffrey Fredman
*Assistant Examiner*—Sumesh Kaushal
(74) *Attorney, Agent, or Firm*—Woodcock Washburn LLP

(57) ABSTRACT

The present invention provides nucleic acid and amino acid sequences of an ATP binding cassette transporter and mutated sequences thereof associated with macular degeneration. Methods of detecting agents that modify ATP-binding cassette transporter comprising combining purified ATP binding cassette transporter and at least one agent suspected of modifying the ATP binding cassette transporter an observing a change in at least one characteristic associated with ATP binding cassette transporter. Methods of detecting macular degeneration is also embodied by the present invention.

18 Claims, 19 Drawing Sheets-

OTHER PUBLICATIONS

Blacharski, D.A., *Fundus flavimaculatus. In Retinal Dystrophies and Degenerations*, D.A. Newsome, ed., 1988, New York: Raven Press, Chapter 9, 135–159.

Boguski, M.S. et al., "dbEST—database for 'expressed sequence tags'", *Nature Genet*, 1993, 4, 332–333.

Bradley, A., "Production and Analysis of Chimeric Mice", *Teratocarcinomas and Embryonic Stem Cells—A Practical Approach*, 1987, Roberson (ed.), IRL Press, 113–151.

Chen, Z.–Y., et al., "Norrie Disease Gene: Characterization of Deletions and Possible Function ", *Genomics*, 1993, 16, 533–535.

Childs, S., et al., "The MDR Superfamily of Genes and Its Biological Implications", *Importance Advances in Oncology*, 1994, DeVita, V.T., et al., eds. Lippincott Company, Philadelphia, Pennsylvania, 21–36.

Chiu, M. I. et al., "Murine and Bovine Blue Cone Pigment Genes: Cloning and Characterization of Two New Members of the S Family of Visual Pigments", *Genomics*, 1994, 21, 440–443.

Chomczynski, P. et al., "Single–Step Method of RNA Isolation by Acid Guanidinium Thiocyanate–Phenol–Chloroform Extraction", *Analyt. Biochem.*, 1987, 162, 156–159.

Cline, M.J., "Perspectives for Gene Therapy: Inserting New Genetic Information into Mammalian Cells by Physical Techniques and Viral Vectors", *Pharmac. Thera.*, 1985, 29, 69–92.

Daemen, F.J.M., "Vertebrate Rod Outer Segment Membranes", *Biochem. Biophys. Acta*, 1973, 300, 255–288.

de la Salle, H. et al., "Homozygous Human TAP Peptide Transporter Mutation in HLA Class I Deficiency", *Science*, 1994, 265, 237–241.

Dean, M. et al., "Evolution of ATP–binding cassetter transporter genes", *Curr. Opin. Genet. & Dev.*, 1995, 5, 779–785.

Dean, M. et al., "Mapping and Sequencing of Two Yeast Genes Belonging to the ATP–Binding Cassetter Superfamily", *Yeast*, 1994, 10, 377–383.

Devereaux, J. et al., "A comprehensive set of sequence analysis programs for the VAX", *Nucleic Acids Res.*, 1984, 12, 387–395.

Dowling, J. E., "Chemistry of Visual Adaptation in the Rat", *Nature*, 1960, 188, 114–118.

Dryja, T.P. et al., "Molecular genetics of retinitis pigmentosa", *Hum. Mol. Genet.*, 4, 1995, 1739–1743.

Eagle, R.C. Jr. et al., "Retinal Pigment Epithelial Abnormalities in Fundus Flavimaculatus", *Ophthalmology*, 1980, 87, 1189–1200.

Feeney, L., "Lipofuscin and melanin of human retinal pigment epithelium", *Invest. Ophthalmol. Vis. Sci.*, 1978, 17, 583–600.

Feng, D.–F. et al., "Progressive Sequence Alignment as a Prerequisite to Correct Phylognetic Trees", *J. Mol. Evol.*, 1987, 25, 351–360.

Fishman, G.A., "Fundus Flavimaculatus", *Arch Ophthalmol.*, 1976, 94, 2061–2067.

Fong, S.–L. et al., "Purification and Characterization of a Retinol–binding Glycoprotein Synthesized and Secreted by Bovine Neural Retina", *J. Biol. Chem.*, 1984, 259, 6534–6542.

Gass, J.D.M., "Stargardt's disease (Fundus Flavimaculatus)", *Stereoscopic Atlas of Macular Diseases: Diagnosis and Treatment*, 1987, vol. 1, 3rd edition, C.V. Mosby Company, St Louis, MO, 256–261.

Gerber, S. et al., "A Gene for Late–Onset Fundus Flavimaculatus with Macular Dystrophy Maps to Chromosome 1p13", *Am. J. Hum. Genet.*, 1995, 56, 396–399.

Glavač, D. et al., "Optimization of the Single–Strand Conformation Polymorphism (SSCP) Technique for Detection of Point Mutations", *Hum. Mutat.*, 1993, 2, 404–414.

Hayes, K.C., "Retinal degeneration in monkeys induced by deficiencies of vitamin E or A", *Invest. Ophthalmology*, 1974, 13, 499–510.

Hettema, E.H. et al., "The ABC transporter proteins Pat1 and Pat2 are required for import of long–chain fatty acids into peroxisomes of *Saccharomces cerevisiae*", *EMBO J.*, 1996, 15, 3813–3822.

Hoyng, C.B. et al., "Genetic fine mapping of the gene for recessive Stargardt disease", *Hum. Genet.*, 1996, 98, 500–504.

Hyde, S.C. et al., "Structural model of ATP–binding proteins associated with cystic fibrosis, multidrug resistance and bacterial transport", *Nature*, 1990, 346, 362–365.

Klein, B.A. et al., "Fundud Flavimaculatus: Clinical, Functional and Histopathic Observations", *Am. J. Ophthalmol.*, 1967, 64, 3–23.

Klugbauer, N. et al., "Primary structure of a novel ABC transporter with a chromosomal localization on the band encoding the multidrug resistance–associated protein", *FEBS Letts.*, 1996, 391, 61–65.

Kuwano, Y. et al., "Molecular Cloning and Nucleotide Sequence of DNA Complementary to Rat Ribosomal Protein S26 Messenger RNA", *J. Biochem.*, 1985, 97, 983–992.

Kwoh, D.Y. et al., "Transcription–based amplification system and detection of amplified human immunodeficiency virus type 1 with a bead–based sandwich hybridization format", *Proc. Natl. Acad. Sci. (U.S.A.)* 1989, 86, 1173–1177.

Lennon, G. et al., "The I.M.A.G.E. Consortium: An Integrated Molecular Analysis of Genomes and Their Expression", *Genomics*, 1996, 33, 151–152.

Lopez, P.F. et al., "Autosomal–dominant Fundus Flavimaculatus: Clinicopathologic Correlation", *Ophthalmology*, 1990, 97, 798–809.

Luciani, M.–F. et al., "Cloning of Two Novel ABC Transporters Mapping on Human Chromosome 9", *Genomics*, 1994, 21, 150–159.

Luciani, M.–F. et al., "The ATP binding cassette transporter ABC1, is required for the engulfment of corpses generated by apoptotic cell death", *EMBO J.*, 1996, 15, 226–235.

McDonnell, P.J. et al., "Fundus Flavimaculatus without Maculopathy: A Clinicopathologic Study" *Ophthalmology*, 1986, 93, 116–119.

Meindl, A. et al., "Norrie disease is caused by mutations in an extracellular protein resembling C–terminal globular domain of mucins", *Nature Genetics*, 1992, 2, 139–143.

Meindl, A. et al., "A gene (RPGR) with homology to the RCC1 guanine nucleotide exchange factor is mutated in X–linked retinitis pigmentosa (RP3)", *Nature Genetics*, 1996, 13, 35–42.

Michaelis, S. et al., "Sequence comparison of yeast ATP binding cassette proteins", *Cold Spring Harbor Symposium on Quantitative Biology*, vol. LX: *Protein Kinesis—The Dynamics of Protein Trafficking and Stability*, 1995, Cold Spring Harbor Laboratory Press, Cold Spring Harbor.

Mosser, J. et al., "Putative X–linked adrenoleukodysrophy gene shares unexpected homology with ABC transporter", *Nature*, 1993, 361, 726–730.

Nathans, J. et al., "Molecular Genetics of Human Color Vision: The Genes Enxoding Blue, Green and Red Pigments", *Science*, 1986, 232, 193–202.

Nickells, R. W. et al., "Cloning and Characterization of Rod Opsin cDNA From the Old World Monkey, *Macaca fascicularis*", *Investigation Ophthalmology and Visual Science*, 1995, 36, 72–82.

Noble, K.G. et al., "Stargardt's Disease and Fundus Flavimaculatus", *Arch. Ophthalmol.*, 1979, 97, 1281–1285.

Ohara, O., et al., "One–sided polymerase chain reaction: The amplification of cDNA", *Proc. Natl. Acad. Sci. (U.S.A.)*, 1989, 86, 5673–5677.

Orita, M. et al., "Rapid and Sensitive Detection of Point Mutations and DNA Polymorphisms Using the Polymerase Chain Reaction", *Genomics*, 1989, 5, 874–879.

Rando, R.R., "The Chemistry of Vitamin and Vision" *Angew. Chem. Int. Ed. Engl.*, 1990, 29, 461–480.

Riordan, J.R. et al., "Identification of the Cystic Fibrosis Gene: Cloning and characterization of Complementary DNA", *Science*, 1989, 245, 1066–1073.

Roa, B.B. et al., "Charcot–Marie–Tooth Disease Type 1A: Association with a Spontaneous Point Mutation in the PMP22 Gene", *New Eng. J. Med.*, 1993, 329, 96–101.

Roa, B.B. et al., "Myelin Protein Zero (MPZ) Gene Mutations in Nonduplication Type 1 Charcot–Marie–Tooth Disease", *Hum. Mut.*, 1996, 7, 36–45.

Rowe, L.B. et al., "Maps from two interspecific backcross DNA panels available as a community genetic mapping resource", *Mammalian Genome*, 1994, 5, 253–274.

Schaeren–Wiemers, N. et al., "A single protocol to detect transcripts of various types and expression levels in neural tissue and cultured cells: in situ hybridization using digoxigenin–labeled cRNA probes", *Histochemistry*, 1993, 100, 431–440.

Seabra, M.C. et al., "Retinal Degeneration inChoroideremia: Deficiency of Rab Geranylgeranyl Transferase", *Science*, 1993, 259, 377–381.

Shani, N. et al., "A *Saccharomyces cerevisiae* homolog of the human adrenoleukodystrophy transporter is a heterodimer of two half ATP–binding cassette transporters", *Proc. Natl. Acad. Sci. USA*, 1996, 93, 11901–11906.

Shimozawa, N. et al., "A Human Gene Responsible for Zellweger Syndrome That Affects Peroxosome Assembly", *Science*, 1992, 255, 1132–1134.

Smit, J.J.M. et al., "Homozygous Disruption of the Murine mdr2 P–Glycoprotein Gene Leads to a Complete Absence of Phospholipid from Bile and to Liver Disease", *Cell*, 1993, 75, 451–462.

Steinmetz, R.L. et al., "Histopathology of Incipient Fundus Flavimaculatus", *Ophthalmology*, 1991, 98, 953–956.

Stone, E.M. et al., "Clinical Features of a Stagardt–Like Dominant Progressive Macular Dystrophy With Genetic Linkage to Chromosome 6q", *Arch. Ophthalmol.*, 1994, 112, 765–772.

Sun, H. et al., "Stargardt's ABCR is localized to the disc membrane of retinal rod outer segments", *Nature Genetics*, 1997, 17, 15–16.

Thomas, P.M. et al., "Mutations in the Sulfonylurea Receptor Gene in Familial Persistent Hyperindulinemic Hypoglycemia of Infancy", *Science*, 1995, 268, 426–429.

Valle, D. et al."The Hyperornithinemias", *The Metabolic and Molecular Basis of Inherited Disease*, Scriver, C.R. et al., eds., 1995, New York: McGraw Hill, Chapter 31, 1147–1185.

van Helvoort, A. et al., "MDR1 P–Glycoprotein Is a Lipid Translocase of Broad Specificity, While MDR3 P–Glycoprotein Specifically Translocates Phosphatidylcholine", *Cell*, 1996, 87, 507–517.

Walker, G. T. et al., "Isothermal in vitro amplification of DNA by a restriction enzyme / DNA polymerase system", *Proc. Natl. Acad, Sci. (U.S.A.)* 1992, 89, 392–396.

Wang, Y. et al., "A Large Family of Putative Transmembrane Receptors Homologous to the Product of the Drosophila Tissue Polarity Gene frizzled", *J. Biol. Chem.*, 1996, 271, 4468–4476.

Warner, L.E. et al., "Clinincal Phenotypes of Different MPZ ($P_0$) Mutations May Include Charcot–Marie–Tooth Type 1B, Dejerine–Sottas, and Congenital Hypomyelination", *Neuron*, 1996, 17, 451–460.

Weber, B.H.F. et al., "Mutations in the tissue inhibitor of metalloproteinases–3 (TIMP3) in patients with Sorsby's fundus dystrophy", *Nat. Genet.*, 1994, 8, 352–356.

Weiter, J.J. et al., "Retinal Pigment Epithelial Lipofuscin and Melanin and Choroidal Melanin in human eyes", *Invest. Ophthalmol. & Vis. Sci.*, 1986, 27, 145–152.

White, M.B. et al., "Detecting Single Base Substitutions as Heteroduplex Polymorphisms", *Genomics*, 1992, 12, 301–306.

Wing, G.L. et al., "The topography and age relationship of lipofuscin concentration in the retinal pigment epithelium", *Invest. Ophthalmol. & Vis. Sci.*, 1978, 17, 601–607.

Wu, D.Y. et al., "The Ligation Amplification Reation (LAR)—Amplification of Specific DNA Sequences Using Sequential Rounds of Template–Dependent ligation", *Genomics* 1989, 4, 560–569.

Zhang, K. et al., "A Dominant Stargardt's Macular Dystrophy Locus Maps to Chromosome 13q34", *Arch. Ophthalmol.*, 1994, 112, 759–764.

Zhou, H. et al., "Retina–Derived POU–Domain Factor–1: A Complex POU–Domain Gene Implicated in the Development of Retinal Ganglion and Amacrine Cells", *J. Neurosci.*, 1996, 16, 2261–2274.

Gerber, S. et al., "Complete Exon–Intron Structure of the Retina–Specific ATP Binding Transporter Gene (ABCR) Allows the Identification of Novel Mutations Underlying Statrgardt Disease", *Genomics*, 1998, 48, 139–142.

Anderson, K.L. et al., *Am. J. Hum. Genet.*, 1995, 57, 1351–1363.

Lincoln, A.L. et al., Primer: a computer program for automatically selecting PCR primers, 1991, *Whitehead Institute Technical Report*.

Maxam et al., *Proc. Natl. Acad. Sci.*. 1977, 74, 560–564.

Pinkert, C., *Transgenic Animal Technology*, 1994, Academic Press, Inc., San Diego, CA.

Sanger et al., *Proc. Nat'l Acad. Sci, U.S.A.*, 1977, 74, 5463.

Zinn, K. M. et al., *The Retinal Pigment Epithelium*, 1979, Harvard University Press, Cambridge, MA, 521.

Hillier, L., et al., "ys81h09.r1 soares retina N2b4HR homo sapiens cDNA clone IMAGE:221249 5' similar to SP: C48B4.5 CE00488 ATP–binding tansport protein; mRNA sequence," *Database EMBL Online!* Dec. 1, 1995, Acc. No. H91947, XP002191077, 1 page.

Illing, M., et al., "The 220–kDa rim protein of retinal rod outer segments is a member of the ABC transporter superfamily," *J. of Biological Chem.*, Apr. 11, 1997, *272(15)*, 10303–10310.

Nasonkin, I., et al., "Mapping of the rod photoreceptor ABC transporter (ABCR) to 1p21–p22.1 and identification of novel mutations in Stargardt's disease," *Hum Genet*, 1998, *102*, 21–26.

* cited by examiner

```
                -580                  -560                  -540
        CCCCTACCCCTCTGCTAAGCTCAGGGATAACCCAACTAGCTGACCATAATGACTTCAGTC
                -520                  -500                  -480
        ATTACGGAGCAAGATGAAAGACTAAAAGAGGGAGGGATCACTTCAGATCTGCCGAGTGAG
                -460                  -440                  -420
        TCGATTGGACTTAAAGGGCCAGTCAAACCCTGACTGCCGGCTCATGGCAGGCTCTTGCCG
                -400                  -380                  -360
        AGGACAAATGCCCAGCCTATATTTATGCAAAGAGATTTTGTTCCAAACTTAAGGTCAAAG
                -340                  -320                  -300
        ATACCTAAAGACATCCCCCTCAGGAACCCCTCTCATGGAGGAGAGTGCCTGAGGGTCTTG
                -280                  -260                  -240
        GTTTCCCATTGCATCCCCCACCTCAATTTCCCTGGTGCCCAGCCACTTGTGTCTTTAGGG
                -220                  -200                  -180
        TTCTCTTTCTCTCCATAAAAGGGAGCCAACACAGTGTCGGCCTCCTCTCCCCAACTAAGG
                -160                  -140                  -120
        GCTTATGTGTAATTAAAAGGGATTATGCTTTGAAGGGGAAAAGTAGCCTTTAATCACCAG
                -100                  -80                   -60
        GAGAAGGACACAGCGTCCGGAGCCAGAGGCGCTCTTAACGGCGTTTATGTCCTTTGCTGT
                -40                   -20                    0
        CCTGAGGGGCCTCAGCTCTGACCAATCTGGTCTTCGTGTGGTCATTAGCATGGGCTTCGT
                                                         M   G   F   V
                 20                    40                   60
        GAGACAGATACAGCTTTTGCTCTGGAAGAACTGGACCCTGCGGAAAAGGCAAAAGATTCG
         R   Q   I   Q   L   L   W   K   N   W   T   L   R   K   R   Q   K   I   R
                 80                   100                   120
        CTTTGTGGTGGAACTCGTGTGGCCTTTATCTTTATTTCTGGTCTTGATCTGGTTAAGGAA
         F   V   V   E   L   V   W   P   L   S   L   F   L   V   L   I   W   L   R   N
                140                   160                   180
        TGCCAACCCGCTCTACAGCCATCATGAAT|GCCATTTCCCCAACAAGGCGATGCCCTCAGC
         A   N   P   L   Y   S   H   H   E   C   H   F   P   N   K   A   M   P   S   A
                200                   220                   240
        AGGAATGCTGCCGTGGCTCCAGGGGATCTTCTGCAATGTGAACAATCCCTGTTTTCAAAG
         G   M   L   P   W   L   Q   G   I   F   C   N   V   N   N   P   C   F   Q   S
                260                   280                   300
        CCCCACCCCAGGAGAATCTCCTGGAATTGTGTCAAACTATAACAACTCCAT|CTTGGCAAG
         P   T   P   G   E   S   P   G   I   V   S   N   Y   N   N   S   I   L   A   R
                320                   340                   360
        GGTATATCGAGATTTTCAAGAACTCCTCATGAATGCACCAGAGAGCCAGCACCTTGGCCG
         V   Y   R   D   F   Q   E   L   L   M   N   A   P   E   S   Q   H   L   G   R
                380                   400                   420
        TATTTGGACAGAGCTACACATCTTGTCCCAATTCATGGACACCCTCCGGACTCACCCGGA
         I   W   T   E   L   H   I   L   S   Q   F   M   D   T   L   R   T   H   P   E
                440                   460                   480
        GAGAATTGCAG|GAAGAGGAATACGAATAAGGGATATCTTGAAAGATGAAGAAACACTGAC
         R   I   A   G   R   G   I   R   I   R   D   I   L   K   D   E   E   T   L   T
                500                   520                   540
        ACTATTTCTCATTAAAAACATCGGCCTGTCTGACTCAGTGGTCTACCTTCTGATCAACTC
         L   F   L   I   K   N   I   G   L   S   D   S   V   V   Y   L   L   I   N   S
```

*FIG. 3A*

```
       560                  580                  600
TCAAGTCCGTCCAGAGCAG|TTCGCTCATGGAGTCCCGGACCTGGCGCTGAAGGACATCGC
  Q  V  R  P  E  Q   F  A  H  G  V  P  D  L  A  L  K  D  I  A
       620                  640                  660
CTGCAGCGAGGCCCTCCTGGAGCGCTTCATCATCTTCAGCCAGAGACGCGGGCAAAGAC
  C  S  E  A  L  L  E  R  F  I  I  F  S  Q  R  R  G  A  K  T
       680                  700                  720
GGTGCGCTATGCCCTGTGCTCCCTCTCCCAGGGCACCCTACAGTGGATAGAAGACACTCT
  V  R  Y  A  L  C  S  L  S  Q  G  T  L  Q  W  I  E  D  T  L
       740                  760                  780
GTATGCCAACGTGGACTTCTTCAAGCTCTTCCGTGTG|CTTCCCACACTCCTAGACAGCCG
  Y  A  N  V  D  F  F  K  L  F  R  V   L  P  T  L  L  D  S  R
       800                  820                  840
TTCTCAAGGTATCAATCTGAGATCTTGGGGAGGAATATTATCTGATATGTCACCAAGAAT
  S  Q  G  I  N  L  R  S  W  G  G  I  L  S  D  M  S  P  R  I
       860                  880                  900
TCAAGAG|TTTATCCATCGGCCGAGTATGCAGGACTTGCTGTGGGTGACCAGGCCCCTCAT
  Q  E   F  I  H  R  P  S  M  Q  D  L  L  W  V  T  R  P  L  M
       920                  940                  960
GCAGAATGGTGGTCCAGAGACCTTTACAAAGCTGATGGGCATCCTGTCTGACCTCCTGTG
  Q  N  G  G  P  E  T  F  T  K  L  M  G  I  L  S  D  L  L  C
       980                  1000                 1020
TGGCTACCCCGAGGGAGGTGGCTCTCGGGTGCTCTCCTTCAACTGGTATGAAGACAATAA
  G  Y  P  E  G  G  G  S  R  V  L  S  F  N  W  Y  E  D  N  N
       1040                 1060                 1080
CTATAAGGCCTTTCTGGGGATTGACTCCACAAGGAAGGATCCTATCTATTCTTATGACAG
  Y  K  A  F  L  G  I  D  S  T  R  K  D  P  I  Y  S  Y  D  R
       1100                 1120                 1140
AAGAACAA|CATCCTTTTGTAATGCATTGATCCAGAGCCTGGAGTCAAATCCTTTAACCAA
  R  T  T   S  F  C  N  A  L  I  Q  S  L  E  S  N  P  L  T  K
       1160                 1180                 1200
AATCGCTTGGAGGGCGGCAAAGCCTTTGCTGATGGGAAAAATCCTGTACACTCCTGATTC
  I  A  W  R  A  A  K  P  L  L  M  G  K  I  L  Y  T  P  D  S
       1220                 1240                 1260
ACCTGCAGCACGAAGGATACTGAAGAAT|GCCAACTCAACTTTTGAAGAACTGGAACACGT
  P  A  A  R  R  I  L  K  N   A  N  S  T  F  E  E  L  E  H  V
       1280                 1300                 1320
TAGGAAGTTGGTCAAAGCCTGGGAAGAAGTAGGGCCCCAGATCTGGTACTTCTTTGACAA
  R  K  L  V  K  A  W  E  E  V  G  P  Q  I  W  Y  F  F  D  N
       1340                 1360                 1380
CAGCACACAGATGAACATGATCAGA|GATACCCTGGGGAACCCAACAGTAAAAGACTTTTT
  S  T  Q  M  N  M  I  R   D  T  L  G  N  P  T  V  K  D  F  L
       1400                 1420                 1440
GAATAGGCAGCTTGGTGAAGAAGGTATTACTGCTGAAGCCATCCTAAACTTCCTCTACAA
  N  R  Q  L  G  E  E  G  I  T  A  E  A  I  L  N  F  L  Y  K
       1460                 1480                 1500
GGGCCCTCGGGAAAGCCAGGCTGACGACATGGCCAACTTCGACTGGAGGGACATATTTAA
  G  P  R  E  S  Q  A  D  D  M  A  N  F  D  W  R  D  I  F  N
       1520                 1540                 1560
CATCACTGATCGCACCCTCCGCCTGGTCAATCAATACCTGGAG|TGCTTGGTCCTGGATAA
  I  T  D  R  T  L  R  L  V  N  Q  Y  L  E   C  L  V  L  D  K
```

*FIG. 3B*

```
         1580              1600              1620
GTTTGAAAGCTACAATGATGAAACTCAGCTCACCCAACGTGCCCTCTCTCTACTGGAGGA
  F  E  S  Y  N  D  E  T  Q  L  T  Q  R  A  L  S  L  L  E  E
         1640              1660              1680
AAACATGTTCTGGGCCGGAGTGGTATTCCCTGACATGTATCCCTGGACCAGCTCTCTACC
  N  M  F  W  A  G  V  V  F  P  D  M  Y  P  W  T  S  S  L  P
         1700              1720              1740
ACCCCACGTGAAGTATAAGATCCGAATGGACATAGACGTGGTGGAGAAAACCAATAAGAT
  P  H  V  K  Y  K  I  R  M  D  I  D  V  V  E  K  T  N  K  I
         1760              1780              1800
TAAAGACAG|GTATTGGGATTCTGGTCCCAGAGCTGATCCCGTGGAAGATTTCCGGTACAT
  K  D  R  Y  W  D  S  G  P  R  A  D  P  V  E  D  F  R  Y  I
         1820              1840              1860
CTGGGGCGGGTTTGCCTATCTGCAGGACATGGTTGAACAGGGGATCACAAGGAGCCAGGT
  W  G  G  F  A  Y  L  Q  D  M  V  E  Q  G  I  T  R  S  Q  V
         1880              1900              1920
GCAGGCGGAGGCTCCAGTTGGAATCTACCTCCAGCAGATGCCCTACCCCTGCTTCGTGGA
  Q  A  E  A  P  V  G  I  Y  L  Q  Q  M  P  Y  P  C  F  V  D
         1940              1960              1980
CGATTC|TTTTCATGATCATCCTGAACCGCTGTTTCCCTATCTTCATGGTGCTGGCATGGAT
  D  S  F  M  I  I  L  N  R  C  F  P  I  F  M  V  L  A  W  I
         2000              2020              2040
CTACTCTGTCTCCATGACTGTGAAGAGCATCGTCTTGGAGAAGGAGTTGCGACTGAAGGA
  Y  S  V  S  M  T  V  K  S  I  V  L  E  K  E  L  R  L  K  E
         2060              2080              2100
GACCTTGAAAAATCAGGGTGTCTCCAATGCAGTGATTTGGTGTACCTGGTTCCTGGACAG
  T  L  K  N  Q  G  V  S  N  A  V  I  W  C  T  W  F  L  D  S
         2120              2140              2160
CTTCTCCATCATGTCGATGAGCATCTTCCTCCTGACGATATTCATCATG|CATGGAAGAAT
  F  S  I  M  S  M  S  I  F  L  L  T  I  F  I  M     H  G  R  I
         2180              2200              2220
CCTACATTACAGCGACCCATTCATCCTCTTCCTGTTCTTGTTGGCTTTCTCCACTGCCAC
  L  H  Y  S  D  P  F  I  L  F  L  F  L  L  A  F  S  T  A  T
         2240              2260              2280
CATCATGCTGTGCTTTCTGCTCAGCACCTTCTTCTCCAAGGCCAGTCTGGCAGCAGCCTG
  I  M  L  C  F  L  L  S  T  F  F  S  K  A  S  L  A  A  A  C
         2300              2320              2340
TAGTGGTGTCATCTATTTCACCCTCTACCTGCCACACATCCTGTGCTTCGCCTGGCAGGA
  S  G  V  I  Y  F  T  L  Y  L  P  H  I  L  C  F  A  W  Q  D
         2360              2380              2400
CCGCATGACCGCTGAGCTGAAGAAGGCTGTG|AGCTTACTGTCTCCGGTGGCATTTGGATT
  R  M  T  A  E  L  K  K  A  V     S  L  L  S  P  V  A  F  G  F
         2420              2440              2460
TGGCACTGAGTACCTGGTTCGCTTTGAAGAGCAAGGCCTGGGGCTGCAGTGGAGCAACAT
  G  T  E  Y  L  V  R  F  E  E  Q  G  L  G  L  Q  W  S  N  I
         2480              2500              2520
CGGGAACAGTCCCACGGAAGGGGACGAATTCAGCTTCCTGCTGTCCATGCAGATGATGCT
  G  N  S  P  T  E  G  D  E  F  S  F  L  L  S  M  Q  M  M  L
         2540              2560              2580
CCTTGATGCTGCTGTCTATGGCTTACTCGCTTGGTACCTTGATCAGGTGTTTCCAG|GAGA
  L  D  A  A  V  Y  G  L  L  A  W  Y  L  D  Q  V  F  P  G  D
```

*FIG. 3C*

```
                 2600              2620             2640
         CTATGGAACCCCACTTCCTTGGTACTTTCTTCTACAAGAGTCGTATTGGCTTGGCGGTGA
           Y  G  T  P  L  P  W  Y  F  L  L  Q  E  S  Y  W  L  G  G  E
                 2660              2680             2700
         AG|GGTGTTCAACCAGAGAAGAAAGAGCCCTGGAAAAGACCGAGCCCCTAACAGAGGAAAC
            G  C  S  T  R  E  E  R  A  L  E  K  T  E  P  L  T  E  E  T
                 2720              2740             2760
         GGAGGATCCAGAGCACCCAGAAGGAATACACG|ACTCCTTCTTTGAACGTGAGCATCCAGG
           E  D  P  E  H  P  E  G  I  H  D  S  F  F  E  R  E  H  P  G
                 2780              2800             2820
         GTGGGTTCCTGGGGTATGCGTGAAGAATCTGGTAAAGATTTTTGAGCCCTGTGGCCGGCC
           W  V  P  G  V  C  V  K  N  L  V  K  I  F  E  P  C  G  R  P
                 2840              2860             2880
         AGCTGTGGACCGTCTGAACATCACCTTCTACGAGAACCAGATCACCGCATTCCTGGGCCA
           A  V  D  R  L  N  I  T  F  Y  E  N  Q  I  T  A  F  L  G  H
                 2900              2920             2940
         CAATGGAGCTGGGAAAACCACCACCTT|GTCCATCCTGACGGGTCTGTTGCCACCAACCTC
           N  G  A  G  K  T  T  T  L  S  I  L  T  G  L  L  P  P  T  S
                 2960              2980             3000
         TGGGACTGTGCTCGTTGGGGGAAGGGACATTGAAACCAGCCTGGATGCAGTCCGGCAGAG
           G  T  V  L  V  G  G  R  D  I  E  T  S  L  D  A  V  R  Q  S
                 3020              3040             3060
         CCTTGGCATGTGTCCACAGCACAACATCCTGTTCCACCA|CCTCACGGTGGCTGAGCACAT
           L  G  M  C  P  Q  H  N  I  L  F  H  H  L  T  V  A  E  H  M
                 3080              3100             3120
         GCTGTTCTATGCCCAGCTGAAAGGAAAGTCCCAGGAGGAGGCCCAGCTGGAGATGGAAGC
           L  F  Y  A  Q  L  K  G  K  S  Q  E  E  A  Q  L  E  M  E  A
                 3140              3160             3180
         CATGTTGGAGGACACAGGCCTCCACCACAAGCGGAATGAAGAGGCTCAGGACCTATCAG|G
           M  L  E  D  T  G  L  H  H  K  R  N  E  E  A  Q  D  L  S  G
                 3200              3220             3240
         TGGCATGCAGAGAAAGCTGTCGGTTGCCATTGCCTTTGTGGGAGATGCCAAGGTGGTGAT
           G  M  Q  R  K  L  S  V  A  I  A  F  V  G  D  A  K  V  V  I
                 3260              3280             3300
         TCTGGACGAACCCACCTCTGGGGTGGACCCTTACTCGAGACGCTCAATCTGGGATCTGCT
           L  D  E  P  T  S  G  V  D  P  Y  S  R  R  S  I  W  D  L  L
                 3320              3340             3360
         CCTGAAGTATCGCTCAG|GCAGAACCATCATCATGTCCACTCACCACATGGACGAGGCCGA
           L  K  Y  R  S  G  R  T  I  I  M  S  T  H  H  M  D  E  A  D
                 3380              3400             3420
         CCTCCTTGGGGACCGCATTGCCATCATTGCCCAGGGAAGGCTCTACTGCTCAGGCACCCC
           L  L  G  D  R  I  A  I  I  A  Q  G  R  L  Y  C  S  G  T  P
                 3440              3460             3480
         ACTCTTCCTGAAGAACTGCTTTGGCACAGGCTTGTACTTAACCTTGGTGCGCAAGATGAA
           L  F  L  K  N  C  F  G  T  G  L  Y  L  T  L  V  R  K  M  K
                 3500              3520             3540
         AAACATCCAGAGCCAAAGGAAAGGCAGTGAG|GGGACCTGCAGCTGCTCGTCTAAGGGTTT
           N  I  Q  S  Q  R  K  G  S  E     G  T  C  S  C  S  S  K  G  F
                 3560              3580             3600
         CTCCACCACGTGTCCAGCCCACGTCGATGACCTAACTCCAGAACAAGTCCTGGATGGGGA
           S  T  T  C  P  A  H  V  D  D  L  T  P  E  Q  V  L  D  G  D
```

FIG. 3D

```
                3620                  3640                  3660
         TGTAAATGAGCTGATGGATGTAGTTCTCCACCATGTTCCAGAGGCAAAGCTGGTGGAGTG
          V  N  E  L  M  D  V  V  L  H  H  V  P  E  A  K  L  V  E  C
                3680                  3700                  3720
         CATTGGTCAAGAACTTATCTTCCTTCTTCCAAATAAGAACTTCAAGCACAGAGCATATGC
          I  G  Q  E  L  I  F  L  L  P  N  K  N  F  K  H  R  A  Y  A
                3740                  3760                  3780
         CAGCCTTTTCAGAGAGCTGGAGGAGACGCTGGCTGACCTTGGTCTCAGCAGTTTTGGAAT
          S  L  F  R  E  L  E  E  T  L  A  D  L  G  L  S  S  F  G  I
                3800                  3820                  3840
         TTCTGACACTCCCCTGGAAGAG|ATTTTTCTGAAGGTCACGGAGGATTCTGATTCAGGACC
          S  D  T  P  L  E  E     I  F  L  K  V  T  E  D  S  D  S  G  P
                3860                  3880                  3900
         TCTGTTTGCGG|GTGGCGCTCAGCAGAAAAGAGAAAACGTCAACCCCCGACACCCCTGCTT
          L  F  A  G     G  A  Q  Q  K  R  E  N  V  N  P  R  H  P  C  L
                3920                  3940                  3960
         GGGTCCCAGAGAGAAGGCTGGACAGACACCCCAGGACTCCAATGTCTGCTCCCCAGGGGC
          G  P  R  E  K  A  G  Q  T  P  Q  D  S  N  V  C  S  P  G  A
                3980                  4000                  4020
         GCCGGCTGCTCACCCAGAGGGCCAGCCTCCCCCAGAGCCAGAGTGCCCAGGCCCGCAGCT
          P  A  A  H  P  E  G  Q  P  P  P  E  P  E  C  P  G  P  Q  L
                4040                  4060                  4080
         CAACACGGGGACACAGCTGGTCCTCCAGCATGTGCAGGCGCTGCTGGTCAAGAGATTCCA
          N  T  G  T  Q  L  V  L  Q  H  V  Q  A  L  L  V  K  R  F  Q
                4100                  4120                  4140
         ACACACCATCCGCAGCCACAAGGACTTCCTGGCGCAG|ATCGTGCTCCCGGCTACCTTTGT
          H  T  I  R  S  H  K  D  F  L  A  Q     I  V  L  P  A  T  F  V
                4160                  4180                  4200
         GTTTTTGGCTCTGATGCTTTCTATTGTTATCCCTCCTTTTGGCGAATACCCCGCTTTGAC
          F  L  A  L  M  L  S  I  V  I  P  P  F  G  E  Y  P  A  L  T
                4220                  4240                  4260
         CCTTCACCCCTGGATATATGGGCAGCAGTACACCTTCTTCAG|CATGGATGAACCAGGCAG
          L  H  P  W  I  Y  G  Q  Q  Y  T  F  F  S     M  D  E  P  G  S
                4280                  4300                  4320
         TGAGCAGTTCACGGTACTTGCAGACGTCCTCCTGAATAAGCCAGGCTTTGGCAACCGCTG
          E  Q  F  T  V  L  A  D  V  L  L  N  K  P  G  F  G  N  R  C
                4340                  4360                  4380
         CCTGAAGGAAGGGTGGCTTCC|GGAGTACCCCTGTGGCAACTCAACACCCTGGAAGACTCC
          L  K  E  G  W  L  P     E  Y  P  C  G  N  S  T  P  W  K  T  P
                4400                  4420                  4440
         TTCTGTGTCCCCAAACATCACCCAGCTGTTCCAGAAGCAGAAATGGACACAGGTCAACCC
          S  V  S  P  N  I  T  Q  L  F  Q  K  Q  K  W  T  Q  V  N  P
                4460                  4480                  4500
         TTCACCATCCTGCAG|GTGCAGCACCAGGGAGAAGCTCACCATGCTGCCAGAGTGCCCCGA
          S  P  S  C  R     C  S  T  R  E  K  L  T  M  L  P  E  C  P  E
                4520                  4540                  4560
         GGGTGCCGGGGGCCTCCCGCCCCCCCAG|AGAACACAGCGCAGCACGGAAATTCTACAAGA
          G  A  G  G  L  P  P  P  Q     R  T  Q  R  S  T  E  I  L  Q  D
```

*FIG. 3E*

```
           4580                4600                4620
CCTGACGGACAGGAACATCTCCGACTTCTTGGTAAAAACGTATCCTGCTCTTATAAGAAG
  L  T  D  R  N  I  S  D  F  L  V  K  T  Y  P  A  L  I  R  S
           4640                4660                4680
CAGC|TTAAAGAGCAAATTCTGGGTCAATGAACAGAG|GTATGGAGGAATTTCCATTGGAGG
  S   L  K  S  K  F  W  V  N  E  Q  R   Y  G  G  I  S  I  G  G
           4700                4720                4740
AAAGCTCCCAGTCGTCCCCATCACGGGGGAAGCACTTGTTGGGTTTTTAAGCGACCTTGG
  K  L  P  V  V  P  I  T  G  E  A  L  V  G  F  L  S  D  L  G
           4760                4780                4800
CCGGATCATGAATGTGAGCGGG|GGCCCTATCACTAGAGAGGCCTCTAAAGAAATACCTGA
  R  I  M  N  V  S  G   G  P  I  T  R  E  A  S  K  E  I  P  D
           4820                4840                4860
TTTCCTTAAACATCTAGAAACTGAAGACAACATTA|AGGTGTGGTTTAATAACAAAGGCTG
  F  L  K  H  L  E  T  E  D  N  I  K   V  W  F  N  N  K  G  W
           4880                4900                4920
GCATGCCCTGGTCAGCTTTCTCAATGTGGCCCACAACGCCATCTTACGGGCCAGCCTGCC
  H  A  L  V  S  F  L  N  V  A  H  N  A  I  L  R  A  S  L  P
           4940                4960                4980
TAAGGACAGGAGCCCCGAGGAGTATGGAATCACCGTCATTAGCCAACCCCTGAACCTGAC
  K  D  R  S  P  E  E  Y  G  I  T  V  I  S  Q  P  L  N  L  T
           5000                5020                5040
CAAGGAGCAGCTCTCAGAGATTACAGT|GCTGACCACTTCAGTGGATGCTGTGGTTGCCAT
  K  E  Q  L  S  E  I  T  V   L  T  T  S  V  D  A  V  V  A  I
           5060                5080                5100
CTGCGTGATTTTCTCCATGTCCTTCGTCCCAGCCAGCTTTGTCCTTTATTTGATCCAGGA
  C  V  I  F  S  M  S  F  V  P  A  S  F  V  L  Y  L  I  Q  E
           5120                5140                5160
GCGGGTGAACAAATCCAAGCACCTCCAGTTTATCAGTGGAGTGAGCCCCACCACCTACTG
  R  V  N  K  S  K  H  L  Q  F  I  S  G  V  S  P  T  T  Y  W
           5180                5200                5220
GGTGACCAACTTCCTCTGGGACATC|ATGAATTATTCCGTGAGTGCTGGGCTGGTGGTGGG
  V  T  N  F  L  W  D  I   M  N  Y  S  V  S  A  G  L  V  V  G
           5240                5260                5280
CATCTTCATCGGGTTTCAGAAGAAAGCCTACACTTCTCCAGAAAACCTTCCTGCCCTTGT
  I  F  I  G  F  Q  K  K  A  Y  T  S  P  E  N  L  P  A  L  V
           5300                5320                5340
GGCACTGCTCCTGCTGTATGG|ATGGGCGGTCATTCCCATGATGTACCCAGCATCCTTCCT
  A  L  L  L  L  Y  G   W  A  V  I  P  M  M  Y  P  A  S  F  L
           5360                5380                5400
GTTTGATGTCCCCAGCACAGCCTATGTGGCTTTATCTTGTGCTAATCTGTTCATCGGCAT
  F  D  V  P  S  T  A  Y  V  A  L  S  C  A  N  L  F  I  G  I
           5420                5440                5460
CAACAGCAGTGCTATTACCTTCATCTTGGAATTATTTGAGAATAACCGG|ACGCTGCTCAG
  N  S  S  A  I  T  F  I  L  E  L  F  E  N  N  R   T  L  L  R
           5480                5500                5520
GTTCAACGCCGTGCTGAGGAAGCTGCTCATTGTCTTCCCCCACTTCTGCCTGGGCCGGGG
  F  N  A  V  L  R  K  L  L  I  V  F  P  H  F  C  L  G  R  G
```

*FIG. 3F*

```
               5540                5560                5580
CCTCATTGACCTTGCACTGAGCCAGGCTGTGACAGATGTCTATGCCCGGTTTG|GTGAGGA
  L  I  D  L  A  L  S  Q  A  V  T  D  V  Y  A  R  F  G  E  E
         5600                5620                5640
GCACTCTGCAAATCCGTTCCACTGGGACCTGATTGGGAAGAACCTGTTTGCCATGGTGGT
  H  S  A  N  P  F  H  W  D  L  I  G  K  N  L  F  A  M  V  V
         5660                5680                5700
GGAAGGGGTGGTGTACTTCCTCCTGACCCTGCTGGTCCAGCGCCACTTCTTCCTCTCCCA
  E  G  V  V  Y  F  L  L  T  L  L  V  Q  R  H  F  F  L  S  Q
         5720                5740                5760
ATG|GATTGCCGAGCCCACTAAGGAGCCCATTGTTGATGAAGATGATGATGTGGCTGAAGA
  W  I  A  E  P  T  K  E  P  I  V  D  E  D  D  D  V  A  E  E
         5780                5800                5820
AAGACAAAGAATTATTACTGGTGGAAATAAAACTGACATCTTAAGGCTACATGAACTAAC
  R  Q  R  I  I  T  G  G  N  K  T  D  I  L  R  L  H  E  L  T
         5840                5860                5880
CAAG|ATTTATCTGGGCACCTCCAGCCCAGCAGTGGACAGGCTGTGTGTCGGAGTTCGCCC
  K  I  Y  L  G  T  S  S  P  A  V  D  R  L  C  V  G  V  R  P
         5900                5920                5940
TGGAGAG|TGCTTTGGCCTCCTGGGAGTGAATGGTGCCGGCAAAACAACCACATTCAAGAT
  G  E  C  F  G  L  L  G  V  N  G  A  G  K  T  T  T  F  K  M
         5960                5980                6000
GCTCACTGGGGACACCACAGTGACCTCAGGGGATGCCACCGTAGCAGGCAAGAG|TATTTT
  L  T  G  D  T  T  V  T  S  G  D  A  T  V  A  G  K  S  I  L
         6020                6040                6060
AACCAATATTTCTGAAGTCCATCAAAATATGGGCTACTGTCCTCAGTTTGATGCAATCGA
  T  N  I  S  E  V  H  Q  N  M  G  Y  C  P  Q  F  D  A  I  D
         6080                6100                6120
TGAGCTGCTCACAGGACGAGAACATCTTTACCTTTATGCCCGGCTTCGAGGTGTACCAGC
  E  L  L  T  G  R  E  H  L  Y  L  Y  A  R  L  R  G  V  P  A
         6140                6160                6180
AGAAGAAATCGAAAAG|GTTGCAAACTGGAGTATTAAGAGCCTGGGCCTGACTGTCTACGC
  E  E  I  E  K  V  A  N  W  S  I  K  S  L  G  L  T  V  Y  A
         6200                6220                6240
CGACTGCCTGGCTGGCACGTACAGTGGGGGCAACAAGCGGAAACTCTCCACAGCCATCGC
  D  C  L  A  G  T  Y  S  G  G  N  K  R  K  L  S  T  A  I  A
         6260                6280                6300
ACTCATTGGCTGCCCACCGCTGGTGCTGCTG|GATGAGCCCACCACAGGGATGGACCCCCA
  L  I  G  C  P  P  L  V  L  L  D  E  P  T  T  G  M  D  P  Q
         6320                6240                6360
GGCACGCCGCATGCTGTGGAACGTCATCGTGAGCATCATCAGAGAAGGGAGGGCTGTGGT
  A  R  R  M  L  W  N  V  I  V  S  I  I  R  E  G  R  A  V  V
         6380                6400                6420
CCTCACATCCCACAG|CATGGAAGAATGTGAGGCACTGTGTACCCGGCTGGCCATCATGGT
  L  T  S  H  S  M  E  E  C  E  A  L  C  T  R  L  A  I  M  V
         6440                6460                6480
AAAGGGCGCCTTTCGATGTATGGGCACCATTCAGCATCTCAAGTCCAA|ATTTGGAGATGG
  K  G  A  F  R  C  M  G  T  I  Q  H  L  K  S  K  F  G  D  G
         6500                6520                6540
CTATATCGTCACAATGAAGATCAAATCCCCGAAGGACGACCTGCTTCCTGACCTGAACCC
  Y  I  V  T  M  K  I  K  S  P  K  D  D  L  L  P  D  L  N  P
```

*FIG. 3G*

```
                6560                    6580                    6600
TGTGGAGCAGTTCTTCCAGGGGAACTTCCCAGGCAGTGTGCAGAGGGAGAGGCACTACAA
 V   E   Q   F   F   Q   G   N   F   P   G   S   V   Q   R   E   R   H   Y   N
                6620                    6640                    6660
CATGCTCCAGTTCCAGGTCTCCTCCTCCTCCCTGGCGAGGATCTTCCAGCTCCTCCTCTC
 M   L   Q   F   Q   V   S   S   S   S   L   A   R   I   F   Q   L   L   L   S
                6680                    6700                    6720
CCACAAGGACAGCCTGCTCATCGAGGAGTACTCAGTCACACAGACCACACTGGACCAG|GT
 H   K   D   S   L   L   I   E   E   Y   S   V   T   Q   T   T   L   D   Q   V
                6740                    6760                    6780
GTTTGTAAATTTTGCTAAACAGCAGACTGAAAGTCATGACCTCCCTCTGCACCCTCGAGC
 F   V   N   F   A   K   Q   Q   T   E   S   H   D   L   P   L   H   P   R   A
                6800                    6820                    6840
TGCTGGAGCCAGTCGACAAGCCCAG|GACTGATCTTTCACACCGCTCGTTCCTGCAGCCAG
 A   G   A   S   R   Q   A   Q   D   *
                6860                    6880                    6900
AAAGGAACTCTGGGCAGCTGGAGGCGCAGGAGCCTGTGCCCATATGGTCATCCAAATGGA
                6920                    6940                    6960
CTGGCCCAGCGTAAATGACCCCACTGCAGCAGAAAACAAACACACGAGGAGCATGCAGCG
                6980                    7000                    7020
AATTCAGAAAGAGGTCTTTCAGAAGGAAACCGAAACTGACTTGCTCACCTGGAACACCTG
                7040                    7060                    7080
ATGGTGAAACCAAACAAATACAAAATCCTTCTCCAGACCCCAGAACTAGAAACCCCGGGC
                7100                    7120                    7140
CATCCCACTAGCAGCTTTGGCCTCCATATTGCTCTCATTTCAAGCAGATCTGCTTTTCTG
                7160                    7180
CATGTTTGTCTGTGTGTCTGCGTTGTGTGTGATTTTCATGGAAA
```

*FIG. 3H*

```
Abc1 M A C K P Q L R L L L W K N L T F R R R Q T C Q L L L E V A W P F I F L I L I S V R L S Y P P Y E  50
ABCR M G F V R Q I Q L L L W K N W T L R K R Q K I R F V V E L V W P L S L F L V L I W L R N A N P L Y S  50
Abc2 . . . . . . . . . . . . . . . . . . . . . . . . . . . . . . . . . . . . . . . . . . . . . . . . . .   0
ABCC M A V L R Q L A L L L W K N Y T L Q K R K V L V T V L E L F L P L L F S G I L I W L R L K I Q S E N  50

Abc1 Q H E C H F P N K A M P S A G T L P W V Q G I I C N A N N P C F R Y P T P G E A P G V V G N F N K S 100
ABCR H H E C H F P N K A M P S A G M L P W L Q G I F C N V N N P C F Q S P T P G E S P G I V S N Y N N S 100
Abc2 . . . . . . . . . . . . . . . . . . . . . . . . . . . . . . . . . . . . . . . . . . . . . . . . . .   0
ABCC V P N A T I Y P G Q S I Q E L P L F F T F P P P G D T W E L A Y I P S H S D A A K T V T E T V R R A 100

Abc1 I V S R L F S D A Q R L L L Y S Q R D T S I K D M H K V L R M L R Q I K H . . . . . . . . P N S N 141
ABCR I L A R V Y R D F Q E L L M N A P E S Q H L G R I W T E L H I L S Q F M D T L R T H P E R I A G R G 150
Abc2 . . . . . . . . . . . . . . . . . . . . . . . . . . . . . . . . . . . . . . . . . . . . . . . . .   0
ABCC L V I N M R V R G F P S E K D F E D Y I R Y D N C S S S V L A A V V F E H P F N H S K E P L P L A V 150

Abc1 L K L Q D F L V D N E T F S G F L Q H N L S L P R S T V D S L L Q K N V G L Q K V F L Q G Y Q L H L 191
ABCR I R I R D I L K D E E T L T L F L I K N I G L S D S V V Y L L I N S Q V R P E Q F A H G V P D L A L 200
Abc2 . . . . . . . . . . . . . . . . . . . . . . . . . . . . . . . . . . . . . . . . . . . . . . . . .   0
ABCC K Y H L R F S Y T R R N Y M W T Q T G S F F L K E T E G W H . . . . . . . . . . . . . . . . . . . 180

Abc1 A S L . C N G S K L E E I I Q L G D A E V S . . . . . A L C G L P R K K L D A A E R V L R Y N M D I 235
ABCR K D I A C S E A L L E R F I I F S Q R R G A K T V R Y A L C S L S Q G T L Q W I E D T L Y A N V D F 250
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 L K . . . P V V T K L N S T S H L P T Q H L A E A T T V L L D S L G G L A Q E L F S T K S W S D M R 282
ABCR F K L F R V L P T L L D S R S Q G I N L R . . . S W G G I L S D M S P R I Q E F I H R P S M Q D L L 297
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 Q E V M F L T N V N S S S S T Q I Y Q A V S R I V C G H P E G G G L K I K S L N W Y E D N N Y K A 332
ABCR W V T R P L M Q N G G P E T F T K L M G I L S D L L C G Y P E G G G S R V L S F N W Y E D N N Y K A 347
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 L F G G N N T E E D V D T F Y D N S T T P Y C N D L M K N L E S S P L S R I I W K A L K P L L V G K 382
ABCR F L G I D S T R K D P I Y S Y D R R T T S F C N A L I Q S L E S N P L T K I A W R A A K P L L M G K 397
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 I L Y T P D T P A T R Q V M A E V N K T F Q E L A V F H D L E G M W E E L S P Q I W T F M E N S Q E 432
ABCR I L Y T P D S P A A R R I L K N A N S T F E E L E H V R K L V K A W E E V G P Q I W Y F F D N S T Q 447
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 M D L V R T L L D S R G N D Q F W E Q K L D G L D W T A Q D I M A F L A K N P E D V Q S P N G S V Y 482
ABCR M N M I R D T L G N P T V K D F L N R Q L G E E G I T A E A I L N F L Y K G P R E S Q A D D M A N F 497
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 T W R E A F N E T N Q A I Q T I S R F M E C V N L N K L E P I P T E V R L I N K S M E L L D E R K F 532
ABCR D W R D I F N I T D R T L R L V N Q Y L E C L V L D K F E S Y N D E T Q L T Q R A L S L L E E N M F 547
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . . . . . . . . . . . . . . . . . . 180

Abc1 W A G I V F T G I T P D S V E L P H H V K Y K I R M D I D N V E R T N K I K D G Y W D P G P R A D P 582
ABCR W A G V V F P D M Y P W T S S L P P H V K Y K I R M D I D V V E K T N K I K D R Y W D S G P R A D P 597
Abc2 . . . . . . . . . . . . . . . . . . . . . . . . . . . . . . . . . . . . . . . . . . . . . . . . .   0
ABCC . . . . . . . . . . . . . . . . . . . . . . . . . . . . . . . . T T S L F P L F P N P G P R E P T 197
```

```
Abc1  KKEDSVSQSSSDAGLGSDHESDTLTIDVSAISNLIRKHVSEARLVEDIGH  1202
ABCR  SKGFSTTCPAHVDDLIPE---QVLDGDVNELMDVVLHHVPEAKLVECIGQ  1227
Abc2  PRLSSCSEP-----------------QVSQFIRKHVASSLLVSDTST    309
ABCC  ..................HCNPEDISQLVHHHVPNATLESSAGA       792

Abc1  ELTYVLPYEAAKEGAFVELFHEIDDRLSDLGISSYGISETTLEEIFLKVA  1252
ABCR  ELIFLLPNKNFKHRAYASLFRELEETLIADLGLSSFGISDTPLEEIFLKVT  1277
Abc2  ELSYILPSEAVKKGAFERLFQQLEHSLDALHLSSFGLMDTTLEEVFLKVS   359
ABCC  ELSFILPRESTHR--FEGLFAKLEKKQKELGIASFGASITTMEEVFLRVG   840

Abc1  EE..................SGVDAETSDGTLPARRNR-RAFGDKQ-SC  1281
ABCR  ED..................SDSGPLFAGG---AQQKR-ENVNPRH-PC  1303
Abc2  EEDQSLENSEADVKESRKDVLPGAEGLTAVGGQAGNLARCSELAQSQ-AS   408
ABCC  KLVDSSMDI----------QAIQLPALQYQHERRASDWAVDSNLCGA    877

Abc1  LHPFTEDDAVDPNDSDI----DPESRETDLLSGMD--------------  1312
ABCR  LGP-REKAGQTPQDSNVCSPGAPAAHPEGQPPPEPE--------------  1338
Abc2  LQSASSVGSARGEEGTGYSDGYGDYRPLFDNLQDPDNVSLQEAEMEALAQ   458
ABCC  MDPSDGIGALIEEERT---------------------------------   893

Abc1  .GKGSYQLKGWKLTQQQFVALLWKRLLIARSRKGFFAQIVLPAVFVCIA  1361
ABCR  .CPGPQLNTIGTQLVLQHVQALLVKRFQHTIRSHKDFLAQIVLPATFVFLAA  1387
Abc2  VGQGSRKLEGWWLKMRQFIHGLLVKRFHCARRNSKALCSQILLPAFFVCVAA   508
ABCC  ...AVKLNTGLALHCQQFWAMFLKKAAYSWREWKMVAAQVLVPLTCVTLA   940
                                                H1
Abc1  LVFSLIVPPFGKYPSLELQPWMYN-----------EQYTF-VSN  1393
ABCR  LMLSIVIPPFGEYPALTLHPWIYG-----------QQYTF-FSM  1419
Abc2  MTVALSVPEIGDLPPLVLSPSQYHNYTQPRGNFIPYANEERQEYRLRLSP   558
ABCC  LLAINYSSELFDDPMLRLTLGEYGRTVVP--------------------   940

Abc1  DA..................PEDMGTQELLNA........LTKDPGF  1414
ABCR  DE..................PGSEQFTVLADV........LLNKPGF  1440
Abc2  DASPQQLVSTFRLPSGVGATCVLKSPANGSLGPMLNLSSGESRLLAARFF   608
ABCC  ....................FSVPGTSQLGQQL................   982

Abc1  GTRCME----GNPIPDTPCLAGEEDWTISPVPQSIVDLFQNGNWTMKNPS  1460
ABCR  GNRCLK----EGWLPEYPCGNSTPWKTPS-VSPNITQLFQKQKWTQVNPS  1485
Abc2  DSMCLESFTQGLPLSNFVPPPPSPAPSDSPVKPDEDSLQAWNMSLPPTAG   658
ABCC  ...............................................   982

Abc1  PACQCSDKIKKMLPV-----------CPPGAGGLPPPQRKQKTADI  1496
ABCR  PSCRCSTREKLTMLPE-----------CPEGAGGLPPPQRTQRSTEI  1521
Abc2  PETWTSAPSLPRLVHEPVRCTCSAQGTGFSCPSSVGG-HPPQMRVVTGDI   707
ABCC  .....SEHLKDALQ------------------AEGQEPR-----EV  1000

Abc1  LQNLTGRNISDYLVKTYVQIIAKSLKNKIWVNEFRYGGFSLGVSNSQALP  1546
ABCR  LQDLTDRNIISDFLVKTYPALIRSSLKSKFWVNEQRYGGISIGGKLPVVPI  1571
Abc2  LTDITGHNVSEYLLFT--------SDRFRLH--RYGAITTFGN------   739
ABCC  LGDL-----EEFLIF---------RASVEGGGFNERCL----------  1024

Abc1  PSHEVNDAIKQMKKLLKLTKDTSADRFLSSLGRFMAGLDTKNNVKVWFNN  1596
ABCR  TGEALVGFLSDLGRIMNVSGGPITREASKEIPDFLKHLETEDNIKVWFNN  1621
Abc2  ...............VQKSIPASFGARVPPMVRKIAVRRVAQLVLYNN   771
ABCC  ...............VAASFRDVGERTVVNALFNN  1044

Abc1  KGWHAISSFLNVINNAILRANLQKGE-NPSQYGITAFNHPLNLTKQQLSE  1645
ABCR  KGWHALVSFLNVAHNAILRASLPKDR-SPEEYGITVISQPLNLTKEQLSE  1670
Abc2  KGYHSMPTYILNSLNNAILRANLPKSKGNPAAYKITVTNHPMNKTSASLS-   820
ABCC  QAYHSPATALAVDNLLFKL------LCGPHASIIVVSNFPQPRSALQAAK  1088

Abc1  VALMTTSVDVLVSICVIFAMSFVPASFVFLIQERVSKAKHLQFISGVKP  1695
ABCR  ITVLTTSVDAVVAICVIFSMSFVPASFVLYLIQERVNKSKHLQFISGVSP  1720
Abc2  LDYLLQGTDVVIAIFIIVAMSFVPASFVVFLVAEKSTKAKHLQFVSGCNP   870
ABCC  DQFNEGRKGFDIALNLLFAMAFLASTFSILAVSERAVQAKHVQFVSGVHV  1138
```

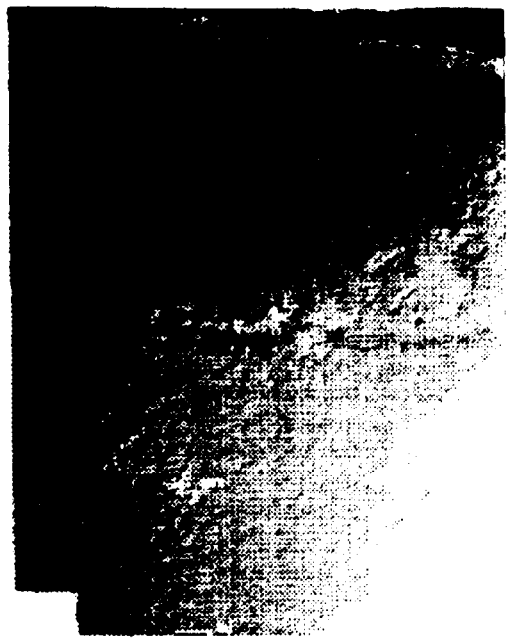 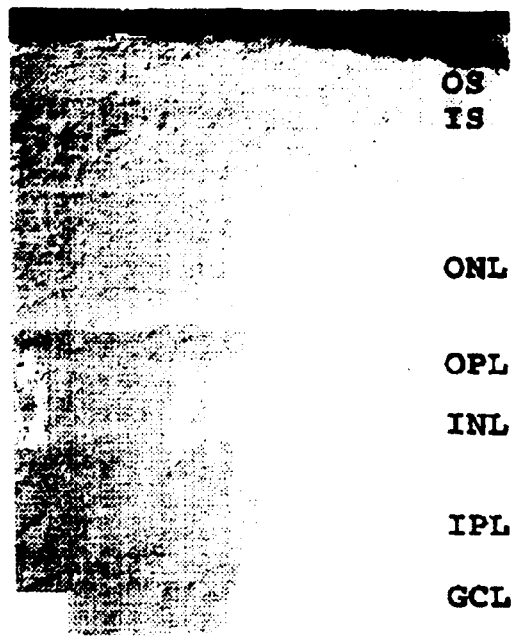
FIG. 7A  FIG. 7B
 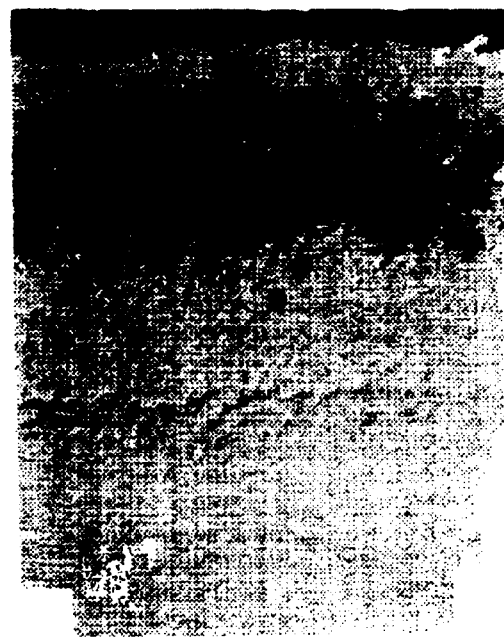
FIG. 7C  FIG. 7D

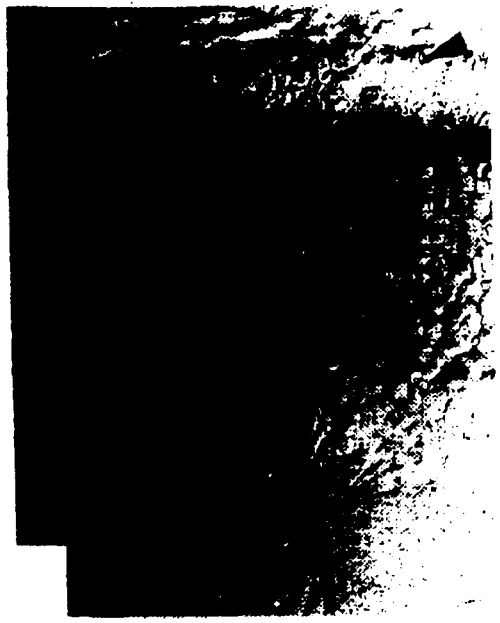 
FIG. 7E  FIG. 7F
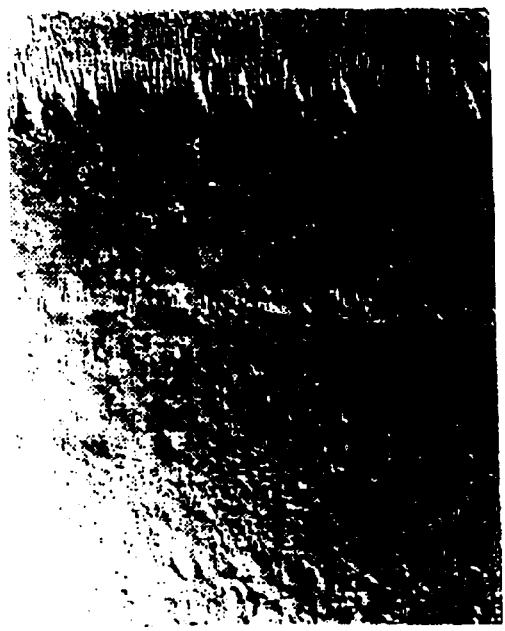 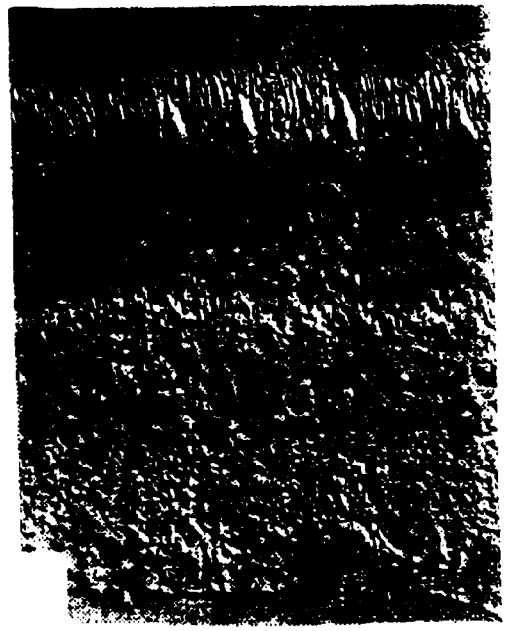
FIG. 7G  FIG. 7H

SEQUENCE LISTING

```
<160> NUMBER OF SEQ ID NOS: 120

<210> SEQ ID NO 1
<211> LENGTH: 7488
<212> TYPE: DNA
<213> ORGANISM: Homo sapiens

<400> SEQUENCE: 1
cccctacccc tctgctaagc tcagggataa cccaactagc tgaccataat gacttcagtc     60
attacggagc aagatgaaag actaaaagag ggagggatca cttcagatct gccgagtgag    120
tcgattggac ttaaagggcc agtcaaaccc tgactgccgg ctcatggcag gctcttgccg    180
aggacaaatg cccagcctat atttatgcaa agagattttg ttccaaactt aaggtcaaag    240
atacctaaag acatccccct caggaacccc tctcatggag gagagtgcct gagggtcttg    300
gtttcccatt gcatccccca cctcaatttc cctggtgccc agccacttgt gtctttaggg    360
ttctctttct ctccataaaa gggagccaac acagtgtcgg cctcctctcc ccaactaagg    420
gcttatgtgt aattaaaagg gattatgctt tgaaggggaa aagtagcctt taatcaccag    480
gagaaggaca cagcgtccgg agccagaggc gctcttaacg gcgtttatgt cctttgctgt    540
```

```
ctgaggggcc tcagctctga ccaatctggt cttcgtgtgg tcattagcat gggcttcgtg      600
agacagatac agcttttgct ctggaagaac tggaccctgc ggaaaaggca aaagattcgc      660
tttgtggtgg aactcgtgtg gcctttatct ttatttctgg tcttgatctg gttaaggaat      720
gccaacccgc tctacagcca tcatgaatgc catttcccca acaaggcgat gccctcagca      780
ggaatgctgc cgtggctcca ggggatcttc tgcaatgtga acaatccctg ttttcaaagc      840 cccacccccag gagaatctcc tggaattgtg tcaaactata caactccat cttggcaagg      900 gtatatcgag attttcaaga actcctcatg aatgcaccag agagccagca ccttggccgt      960
atttggacag agctacacat cttgtcccaa ttcatggaca ccctccggac tcacccggag     1020
agaattgcag gaagaggaat acgaataagg gatatcttga agatgaaga aacactgaca     1080 ctatttctca ttaaaaacat cggcctgtct gactcagtgg tctaccttct gatcaactct     1140
caagtccgtc cagagcagtt cgctcatgga gtcccggacc tggcgctgaa ggacatcgcc     1200
tgcagcgagg ccctcctgga gcgcttcatc atcttcagcc agagacgcgg ggcaaagacg     1260
gtgcgctatg ccctgtgctc cctctcccag ggcaccctac agtggataga agacactctg     1320
tatgccaacg tggacttctt caagctcttc cgtgtgcttc ccacactcct agacagccgt     1380
tctcaaggta tcaatctgag atcttgggga ggaatattat ctgatatgtc accaagaatt     1440
caagagttta tccatcggcc gagtatgcag gacttgctgt gggtgaccag gcccctcatg     1500
cagaatggtg gtccagagac ctttacaaag ctgatgggca tcctgtctga cctcctgtgt     1560
ggctaccccg agggaggtgg ctctcgggtg ctctccttca actggtatga agacaataac     1620
tataaggcct ttctggggat tgactccaca aggaaggatc ctatctattc ttatgacaga     1680
agaacaacat ccttttgtaa tgcattgatc cagagcctgg agtcaaatcc tttaaccaaa     1740
atcgcttgga gggcggcaaa gcctttgctg atgggaaaaa tcctgtacac tcctgattca     1800
cctgcagcac gaaggatact gaagaatgcc aactcaactt ttgaagaact ggaacacgtt     1860
aggaagttgg tcaaagcctg ggaagaagta gggccccaga tctggtactt ctttgacaac     1920
agcacacaga tgaacatgat cagagatacc ctggggaacc caacagtaaa agactttttg     1980
aataggcagc ttggtgaaga aggtattact gctgaagcca tcctaaactt cctctacaag     2040
ggccctcggg aaagccaggc tgacgacatg gccaacttcg actggaggga catatttaac     2100
atcactgatc gcaccctccg cctggtcaat caatacctgg agtgcttggt cctggataag     2160
tttgaaagct acaatgatga aactcagctc acccaacgtg ccctctctct actgaggaa     2220 aacatgttct gggccggagt ggtattccct gacatgtatc cctggaccag ctctctacca     2280 cccccacgtga agtataagat ccgaatggac atagacgtgg tggagaaaac caataagatt     2340
aaagacaggt attgggattc tggtcccaga gctgatcccg tggaagattt ccggtacatc     2400
tggggcgggt tgcctatct gcaggacatg gttaacagg ggatcacaag gagccaggtg     2460
caggcggagg ctccagttgg aatctacctc cagcagatgc cctacccctg cttcgtggac     2520
gattctttca tgatcatcct gaaccgctgt ttccctatct tcatggtgct ggcatggatc     2580
tactctgtct ccatgactgt gaagagcatc gtcttggaga aggagttgcg actgaaggag     2640
accttgaaaa atcagggtgt ctccaatgca gtgatttggt gtacctggtt cctgacagc     2700 ttctccatca tgtcgatgag catcttcctc ctgacgatat catcatgca tggaagaatc     2760 ctacattaca gcgacccatt catcctcttc ctgttcttgt tggctttctc cactgccacc     2820
atcatgctgt gctttctgct cagcaccttc ttctccaagg ccagtctggc agcagcctgt     2880
agtggtgtca tctatttcac cctctacctg ccacacatcc tgtgcttcgc ctggcaggac     2940
```

-continued

```
cgcatgaccg ctgagctgaa gaaggctgtg agcttactgt ctccggtggc atttggattt      3000
ggcactgagt acctggttcg ctttgaagag caaggcctgg ggctgcagtg gagcaacatc      3060
gggaacagtc ccacggaagg ggacgaattc agcttcctgc tgtccatgca gatgatgctc      3120
cttgatgctg ctgtctatgg cttactcgct tggtaccttg atcaggtgtt tccaggagac      3180
tatggaaccc cacttccttg gtactttctt ctacaagagt cgtattggct tggcggtgaa      3240
gggtgttcaa ccagagaaga aagagccctg gaaaagaccg agcccctaac agaggaaacg      3300
gaggatccag agcacccaga aggaatacac gactccttct ttgaacgtga gcatccaggg      3360
tgggttcctg gggtatgcgt gaagaatctg gtaaagattt ttgagccctg tggccggcca      3420
gctgtggacc gtctgaacat caccttctac gagaaccaga tcaccgcatt cctgggccac      3480
aatggagctg ggaaaaccac caccttgtcc atcctgacgg gtctgttgcc accaacctct      3540
gggactgtgc tcgttggggg aagggacatt gaaaccagcc tggatgcagt ccggcagagc      3600
cttggcatgt gtccacagca caacatcctg ttccaccacc tcacggtggc tgagcacatg      3660
ctgttctatg cccagctgaa aggaaagtcc caggaggagg cccagctgga gatggaagcc      3720
atgttggagg acacaggcct ccaccacaag cggaatgaag aggctcagga cctatcaggt      3780
ggcatgcaga gaaagctgtc ggttgccatt gcctttgtgg gagatgccaa ggtggtgatt      3840
ctggacgaac ccacctctgg ggtggaccct tactcgagac gctcaatctg ggatctgctc      3900
ctgaagtatc gctcaggcag aaccatcatc atgtccactc accacatgga cgaggccgac      3960
ctccttgggg accgcattgc catcattgcc cagggaaggc tctactgctc aggcaccccca     4020 ctcttcctga gaactgcttt tggcacaggc ttgtacttaa ccttggtgcg caagatgaaa      4080
aacatccaga gccaaaggaa aggcagtgag gggacctgca gctgctcgtc taagggtttc      4140
tccaccacgt gtccagccca cgtcgatgac ctaactccag aacaagtcct ggatggggat      4200
gtaaatgagc tgatggatgt agttctccac catgttccag aggcaaagct ggtggagtgc      4260
attggtcaag aacttatctt ccttcttcca aataagaact tcaagcacag agcatatgcc      4320
agccttttca gagagctgga ggagacgctg gctgaccttg gtctcagcag ttttggaatt      4380
tctgacactc ccctggaaga gatttttctg aaggtcacgg aggattctga ttcaggacct      4440
ctgtttgcgg gtgcgctca gcagaaaaga gaaaacgtca accccgaca cccctgcttg       4500 ggtcccagag agaaggctgg acagacaccc caggactcca atgtctgctc cccaggggcg      4560
ccggctgctc acccagaggg ccagcctccc ccagagccag agtgcccagg cccgcagctc      4620
aacacgggga cacagctggt cctccagcat gtgcaggcgc tgctggtcaa gagattccaa      4680
cacaccatcc gcagccacaa ggacttcctg gcgcagatcg tgctcccggc tacctttgtg      4740
tttttggctc tgatgctttc tattgttatc cctccttttg gcgaataccc cgctttgacc      4800
cttcacccct ggatatatgg gcagcagtac accttcttca gcatggatga accaggcagt      4860
gagcagttca cggtacttgc agacgtcctc ctgaataagc caggctttgg caaccgctgc      4920
ctgaaggaag ggtggcttcc ggagtacccc tgtggcaact caacaccctg gaagactcct      4980
tctgtgtccc caaacatcac ccagctgttc cagaagcaga atggacaca ggtcaaccct      5040 tcaccatcct gcaggtgcag caccaggagg aagctcacca tgctgccaga gtgccccgag      5100
ggtgccgggg gcctcccgcc cccccagaga acacagcgca gcacggaaat tctacaagac      5160 ctgacgggaca ggaacatctc cgacttcttg gtaaaaacgt atcctgctct tataagagc     5220 agcttaaaga gcaaattctg ggtcaatgaa cagaggtatg gaggaatttc cattggagga     5280
```

```
aagctcccag tcgtccccat cacgggggaa gcacttgttg ggttttaag cgaccttggc    5340 cggatcatga atgtgagcgg gggccctatc actagagagg cctctaaaga aatacctgat    5400
ttccttaaac atctagaaac tgaagacaac attaaggtgt ggtttaataa caaaggctgg    5460
catgccctgg tcagctttct caatgtggcc cacaacgcca tcttacgggc cagcctgcct    5520
aaggacagga gccccgagga gtatggaatc accgtcatta gccaacccct gaacctgacc    5580
aaggagcagc tctcagagat tacagtgctg accacttcag tggatgctgt ggttgccatc    5640
tgcgtgattt tctccatgtc cttcgtccca gccagctttg tcctttattt gatccaggag    5700
cgggtgaaca aatccaagca cctccagttt atcagtggag tgagcccac cacctactgg    5760 gtgaccaact tcctctggga catcatgaat tattccgtga gtgctgggct ggtggtgggc    5820
atcttcatcg ggtttcagaa gaaagcctac acttctccag aaaaccttcc tgcccttgtg    5880
gcactgctcc tgctgtatgg atgggcggtc attcccatga tgtacccagc atccttcctg    5940
tttgatgtcc ccagcacagc ctatgtggct ttatcttgtg ctaatctgtt catcggcatc    6000
aacagcagtg ctattacctt catcttggaa ttatttgaga ataaccggac gctgctcagg    6060
ttcaacgccg tgctgaggaa gctgctcatt gtcttccccc acttctgcct gggccggggc    6120
ctcattgacc ttgcactgag ccaggctgtg acagatgtct atgcccggtt tggtgaggag    6180
cactctgcaa atccgttcca ctgggacctg attgggaaga acctgtttgc catggtggtg    6240 gaagggtgg tgtacttcct cctgaccctg ctggtccagc gccacttctt cctctcccaa    6300
tggattgcca gcccactaa ggagcccatt gttgatgaag atgatgatgt ggctgaagaa    6360
agacaaagaa ttattactgg tggaaataaa actgacatct taaggctaca tgaactaacc    6420
aagatttatc caggcacctc cagcccagca gtggacaggc tgtgtgtcgg agttcgccct    6480
ggagagtgct ttggcctcct gggagtgaat ggtgccggca aacaaccac attcaagatg    6540 ctcactgggg acaccacagt gacctcaggg gatgccaccg tagcaggcaa gagtattta    6600 accaatattt ctgaagtcca tcaaaatatg ggctactgtc ctcagtttga tgcaatcgat    6660
gagctgctca caggacgaga acatctttac ctttatgccc ggcttcgagg tgtaccagca    6720
gaagaaatcg aaaaggttgc aaactggagt attaagagcc tgggcctgac tgtctacgcc    6780
gactgcctgg ctggcacgta cagtgggggc aacaagcgga aactctccac agccatcgca    6840
ctcattggct gcccaccgct ggtgctgctg gatgagccca ccacagggat ggaccccag    6900 gcacgccgca tgctgtggaa cgtcatcgtg agcatcatca gagaagggag ggctgtggtc    6960
ctcacatccc acagcatgga agaatgtgag gcactgtgta cccggctggc catcatggta    7020
aagggcgcct tcgatgtat gggcaccatt cagcatctca gtccaaatt tggagatggc    7080 tatatcgtca caatgaagat caaatcccg aaggacgacc tgcttcctga cctgaaccct    7140
gtggagcagt tcttccaggg gaacttccca ggcagtgtgc agagggagag gcactacaac    7200
atgctccagt tccaggtctc ctcctcctcc ctggcgagga tcttccagct cctcctctcc    7260
cacaaggaca gcctgctcat cgaggagtac tcagtcacac agaccacact ggaccaggtg    7320
tttgtaaatt ttgctaaaca gcagactgaa agtcatgacc tccctctgca ccctcgagct    7380
gctggagcca gtcgacaagc ccaggactga tctttcacac cgctcgttcc tgcagccaga    7440
aaggaactct gggcagctgg aggcgcagga gcctgtgccc atatggtc              7488
```

<210> SEQ ID NO 2
<211> LENGTH: 6819
<212> TYPE: DNA
<213> ORGANISM: Homo sapiens

<400> SEQUENCE: 2

```
atgggcttcg tgagacagat acagcttttg ctctggaaga actggaccct gcggaaaagg      60
caaaagattc gctttgtggt ggaactcgtg tggcctttat ctttatttct ggtcttgatc     120
tggttaagga atgccaaccc gctctacagc catcatgaat gccatttccc caacaaggcg     180
atgccctcag caggaatgct gccgtggctc caggggatct tctgcaatgt gaacaatccc     240
tgttttcaaa gccccacccc aggagaatct cctggaattg tgtcaaacta taacaactcc     300
atcttggcaa gggtatatcg agattttcaa gaactcctca tgaatgcacc agagagccag     360
caccttggcc gtatttggac agagctacac atcttgtccc aattcatgga caccctccgg     420
actcacccgg agagaattgc aggaagagga atacgaataa gggatatctt gaaagatgaa     480
gaaacactga cactatttct cattaaaaac atcggcctgt ctgactcagt ggtctacctt     540
ctgatcaact ctcaagtccg tccagagcag ttcgctcatg gagtcccgga cctggcgctg     600
aaggacatcg cctgcagcga ggccctcctg gagcgcttca tcatcttcag ccagagacgc     660
ggggcaaaga cggtgcgcta tgccctgtgc tccctctccc agggcaccct acagtggata     720
gaagacactc tgtatgccaa cgtggacttc ttcaagctct ccgtgtgct tcccacactc     780
ctagacagcc gttctcaagg tatcaatctg agatcttggg gaggaatatt atctgatatg     840
tcaccaagaa ttcaagagtt tatccatcgg ccgagtatgc aggacttgct gtgggtgacc     900
aggcccctca tgcagaatgg tggtccagag acctttacaa agctgatggg catcctgtct     960
gacctcctgt gtggctaccc cgagggaggt ggctctcggg tgctctcctt caactggtat    1020
gaagacaata actataaggc ctttctgggg attgactcca caaggaagga tcctatctat    1080
tcttatgaca gaagaacaac atccttttgt aatgcattga tccagagcct ggagtcaaat    1140
cctttaacca aaatcgcttg gagggcggca agcctttgc tgatgggaaa atcctgtac     1200
actcctgatt cacctgcagc acgaaggata ctgaagaatg ccaactcaac ttttgaagaa    1260
ctggaacacg ttaggaagtt ggtcaaagcc tgggaagaag tagggcccca gatctggtac    1320
ttctttgaca acagcacaca gatgaacatg atcagagata ccctggggaa cccaacagta    1380
aaagactttt tgaataggca gcttggtgaa gaaggtatta ctgctgaagc catcctaaac    1440
ttcctctaca agggcccctcg ggaaagccag gctgacgaca tggccaactt cgactggagg    1500
gacatattta acatcactga tcgcaccctc cgcctggtca atcaataacct ggagtgcttg    1560
gtcctggata agtttgaaag ctacaatgat gaaactcagc tcacccaacg tgccctctct    1620
ctactgagg aaaacatgtt ctgggccgga gtggtattcc ctgacatgta tcccttgggcc    1680
agctctctac cacccacgt gaagtataag atccgaatgg acatagacgt ggtggagaaa    1740
accaataaga ttaaagacag gtattgggat tctggtccca gagctgatcc cgtggaagat    1800
ttccggtaca tctggggcgg gtttgcctat ctgcaggaca tggttgaaca ggggatcaca    1860
aggagccagg tgcaggcgga ggctccagtt ggaatctacc tccagcagat gccctacccc    1920
tgcttcgtgg acgattcttt catgatcatc ctgaaccgct gtttccctat cttcatggtg    1980
ctggcatgga tctactctgt ctccatgact gtgaagagca tcgtcttgga aaggagttg     2040
cgactgaagg agaccttgaa aaatcagggt gtctccaatg cagtgatttg gtgtacctgg    2100
ttcctggaca gcttctccat catgtcgatg agcatcttcc tcctgacgat attcatcatg    2160
catggaagaa tcctacatta cagcgaccca ttcatcctct tcctgttctt gttggctttc    2220
tccactgcca ccatcatgct gtgctttctg ctcagcacct tcttctccaa ggccagtctg    2280
```

| | |
|---|---|
| gcagcagcct gtagtggtgt catctatttc accctctacc tgccacacat cctgtgcttc | 2340 |
| gcctggcagg accgcatgac cgctgagctg aagaaggctg tgagcttact gtctccggtg | 2400 |
| gcatttggat ttggcactga gtacctggtt cgctttgaag agcaaggcct ggggctgcag | 2460 |
| tggagcaaca tcgggaacag tcccacggaa ggggacgaat tcagcttcct gctgtccatg | 2520 |
| cagatgatgc tccttgatgc tgcgtgctat ggcttactcg cttggtacct tgatcaggtg | 2580 |
| tttccaggag actatggaac cccacttcct tggtactttc ttctacaaga gtcgtattgg | 2640 |
| cttagcggtg aagggtgttc aaccagagaa gaaagagccc tggaaaagac cgagccccta | 2700 |
| acagaggaaa cggaggatcc agagcaccca aaggaatac acgactcctt ctttgaacgt | 2760 |
| gagcatccag ggtgggttcc tggggtatgc gtgaagaatc tggtaaagat ttttgagccc | 2820 |
| tgtggccggc cagctgtgga ccgtctgaac atcaccttct acgagaacca gatcaccgca | 2880 |
| ttcctgggcc acaatggagc tgggaaaacc accaccttgt ccatcctgac gggtctgttg | 2940 |
| ccaccaacct ctgggactgt gctcgttggg ggaagggaca ttgaaaccag cctggatgca | 3000 |
| gtccggcaga gccttggcat gtgtccacag cacaacatcc tgttccacca cctcacggtg | 3060 |
| gctgagcaca tgctgttcta tgcccagctg aaaggaaagt cccaggagga ggcccagctg | 3120 |
| gagatgaaag ccatgttgga ggacacaggc ctccaccaca gcggaatga agaggctcag | 3180 |
| gacctatcag gtggcatgca gagaaagctg tcggttgcca ttgcctttgt gggagatgcc | 3240 |
| aaggtggtga ttctgacga acccaccctct ggggtggacc cttactcgag acgctcaatc | 3300 |
| tgggatctgc tcctgaagta tcgctcaggc agaaccatca tcatgcccac tcaccacatg | 3360 |
| gacgaggccg accaccaagg ggaccgcatt gccatcattg cccagggaag gctctactgc | 3420 |
| tcaggcaccc cactcttcct gaagaactgc tttggcacag gcttgtactt aaccttggtg | 3480 |
| cgcaagatga aaacatcca gagccaaagg aaaggcagtg aggggacctg cagctgctcg | 3540 |
| tctaagggtt tctccaccac gtgtccagcc cacgtcgatg acctaactcc agaacaagtc | 3600 |
| ctggatgggg atgtaaatga gctgatggat gtagttctcc accatgttcc agaggcaaag | 3660 |
| ctggtggagt gcattggtca agaacttatc ttccttcttc caaataagaa cttcaagcac | 3720 |
| agagcatatg ccagccttt cagagagctg gaggagacgc tggctgacct tggtctcagc | 3780 |
| agttttggaa tttctgacac tcccctggaa gagattttt gaaggtcac ggaggattct | 3840 |
| gattcaggac ctctgtttgc gggtggcgct cagcagaaaa gagaaaacgt caacccccga | 3900 |
| caccctgct gggtcccag agagaaggct ggacagacac cccaggactc caatgtctgc | 3960 |
| tccccagggg cgccggctgc tcacccagag gccagcctc cccagagcc agagtgccca | 4020 |
| ggcccgcagc tcaacacggg gacacagctg gtcctccagc atgtgcaggc gctgctggtc | 4080 |
| aagagattcc aacacaccat ccgcagccac aaggacttcc tggcgcagat cgtgctcccg | 4140 |
| gctacctttg tgttttggc tctgatgctt tctattgtta tccttccttt tggcgaatac | 4200 |
| cccgctttga cccttcaccc ctggatatat gggcagcagt acaccttctt cagcatggat | 4260 |
| gaaccaggca gtgagcagtt cacggtactt gcagacgtcc tcctgaataa gccaggctt | 4320 |
| ggcaaccgct gcctgaagga agggtggctt ccggagtacc cctgtggcaa ctcaacaccc | 4380 |
| tggaagactc cttctgtgtc cccaaacatc cccagctgt tccagaagca gaaatggaca | 4440 |
| caggtcaacc cttcaccatc ctgcaggtgc agcaccaggg agaagctcac catgctgcca | 4500 |
| gagtgccccg agggtgccgg gggcctcccg cccccccaga gaacacgcg cagcacggaa | 4560 |
| attctacaag acctgacgga caggaacatc tccgacttct tggtaaaaac gtatcctgct | 4620 |
| cttataagaa gcagcttaaa gagcaaattc tgggtcaatg aacagaggta tggaggaatt | 4680 |

-continued

```
tccattggag gaaagctccc agtcgtcccc atcacggggg aagcacttgt tgggttttta    4740
agcgaccttg gccggatcat gaatgtgagc gggggccCta tcactagaga ggcctctaaa    4800
gaaatacctg atttccttaa acatctagaa actgaagaca acattaaggt gtggtttaat    4860
aacaaaggct ggcatgccct ggtcagcttt ctcaatgtgg cccacaacgc catcttacgg    4920
gccagcctgc ctaaggacag gagccccgag gagtatggaa tcaccgtcat tagccaaccc    4980
ctgaacctga ccaaggagca gctctcagag attacagtgc tgaccacttc agtggatgct    5040
gtggttgcca tctgcgtgat tttctccatg tccttcgtcc cagccagctt tgtcctttat    5100
ttgatccagg agcgggtgaa caaatccaag cacctccagt ttatcagtgg agtgagcccc    5160
accacctact gggtgaccaa cttcctctgg gacatcatga attattccgt gagtgctggg    5220
ctggtggtgg gcatcttcat cgggtttcag aagaaagcct acacttctcc agaaaacctt    5280
cctgcccttg tggcactgct cctgctgtat ggatgggcgg tcattcccat gatgtaccca    5340
gcatccttcc tgtttgatgt ccccagcaca gcctatgtgg ctttatcttg tgctaatctg    5400
ttcatcggca tcaacagcag tgctattacc ttcatcttgg aattatttga taataaccgg    5460
acgctgctca ggttcaacgc cgtgctgagg aagctgctca ttgtcttccc ccacttctgc    5520
ctgggccggg gcctcattga ccttgcactg agccaggctg tgacagatgt ctatgcccgg    5580
tttggtgagg agcactctgc aaatccgttc cactgggacc tgattgggaa gaacctgttt    5640
gccatgGtgt tggaaggggt ggtgtacttc ctcctgaccc tgctggtcca gcgccacttc    5700
ttcctctccc aatggattgc cgagcccact aaggagccca ttgttgatga agatgatgat    5760
gtggctgaag aaagacaaag aattattact ggtggaaata aaactgacat cttaaggcta    5820
catgaactaa ccaagattta tctgggcacc tccagcccag cagtggacag gctgtgtgtc    5880
ggagttcgcc ctggagagtg ctttggcctc ctggagtga atggtgccgg caaaacaacc    5940
acattcaaga tgctcactgg ggacaccaca gtgacctcag gggatgccac cgtagcaggc    6000
aagagtattt taaccaatat ttctgaagtc catcaaaata tggctactg tcctcagttt    6060
gatgcaatcg atgagctgct cacaggacga gaacatcttt acctttatgc ccggcttcga    6120
ggtgtaccag cagaagaaat cgaaaaggtt gcaaactgga gtattaagag cctgggcctg    6180
actgtctacg ccgactgcct ggctggcacg tacagtgggg gcaacaagcg gaaactctcc    6240
acagccatcg cactcattgg ctgcccaccg ctggtgctgc tggatgagcc caccacaggg    6300
atggacCccc aggcacgccg catgctgtgg aacgtcatcg tgagcatcat cagaaaaggg    6360
agggctgtgg tcctcacatc ccacagcatg gaagaatgtg aggcactgtg tacccggctg    6420
gccatcatgg taaagggcgc ctttcgatgt atgggcacca ttcagcatct caagtccaaa    6480
tttggagatg gctatatcgt cacaatgaag atcaaatccc gaaggacga cctgcttcct    6540
gacctgaacc ctgtggagca gttcttccag gggaacttcc caggcagtgt gcagagggag    6600
aggcactaca caatgctcca gttccaggtc tcctcctcct ccctggcgag gatcttccag    6660
ctcctcctct cccacaagga cagcctgctc atcgaggagt actcagtcac acagaccaca    6720
ctggaccagg tgtttgtaaa ttttgctaaa cagcagactg aaagtcatga cctccctctg    6780
cacccctcgag ctgctggagc cagtcgacaa gcccaggac                         6819
```

<210> SEQ ID NO 3
<211> LENGTH: 2273
<212> TYPE: PRT
<213> ORGANISM: Homo sapiens

<400> SEQUENCE: 3

| | | | | | | | | | | | | | | |
|---|---|---|---|---|---|---|---|---|---|---|---|---|---|---|
|Met|Gly|Phe|Val|Arg|Gln|Ile|Gln|Leu|Leu|Leu|Trp|Lys|Asn|Trp|Thr|
|1| | | |5| | | |10| | | |15| | |
|Leu|Arg|Lys|Arg|Gln|Lys|Ile|Arg|Phe|Val|Val|Glu|Leu|Val|Trp|Pro|
| | | |20| | | | |25| | | |30| | |
|Leu|Ser|Leu|Phe|Leu|Val|Leu|Ile|Trp|Leu|Arg|Asn|Ala|Asn|Pro|Leu|
| | |35| | | | |40| | | | |45| | |
|Tyr|Ser|His|His|Glu|Cys|His|Phe|Pro|Asn|Lys|Ala|Met|Pro|Ser|Ala|
|50| | | | |55| | | | |60| | | | |
|Gly|Met|Leu|Pro|Trp|Leu|Gln|Gly|Ile|Phe|Cys|Asn|Val|Asn|Asn|Pro|
|65| | | | |70| | | | |75| | | | |80|
|Cys|Phe|Gln|Ser|Pro|Thr|Pro|Gly|Glu|Ser|Pro|Gly|Ile|Val|Ser|Asn|
| | | | |85| | | | |90| | | | |95| |
|Tyr|Asn|Asn|Ser|Ile|Leu|Ala|Arg|Val|Tyr|Arg|Asp|Phe|Gln|Glu|Leu|
| | | |100| | | | |105| | | | |110| | |
|Leu|Met|Asn|Ala|Pro|Glu|Ser|Gln|His|Leu|Gly|Arg|Ile|Trp|Thr|Glu|
| | |115| | | | |120| | | | |125| | | |
|Leu|His|Ile|Leu|Ser|Gln|Phe|Met|Asp|Thr|Leu|Arg|Thr|His|Pro|Glu|
| |130| | | | |135| | | | |140| | | | |
|Arg|Ile|Ala|Gly|Arg|Gly|Ile|Arg|Ile|Arg|Asp|Ile|Leu|Lys|Asp|Glu|
|145| | | | |150| | | | |155| | | | |160|
|Glu|Thr|Leu|Thr|Leu|Phe|Leu|Ile|Lys|Asn|Ile|Gly|Leu|Ser|Asp|Ser|
| | | | |165| | | | |170| | | | |175| |
|Val|Val|Tyr|Leu|Leu|Ile|Asn|Ser|Gln|Val|Arg|Pro|Glu|Gln|Phe|Ala|
| | | |180| | | | |185| | | | |190| | |
|His|Gly|Val|Pro|Asp|Leu|Ala|Leu|Lys|Asp|Ile|Ala|Cys|Ser|Glu|Ala|
| | |195| | | | |200| | | | |205| | | |
|Leu|Leu|Glu|Arg|Phe|Ile|Ile|Phe|Ser|Gln|Arg|Arg|Gly|Ala|Lys|Thr|
| |210| | | | |215| | | | |220| | | | |
|Val|Arg|Tyr|Ala|Leu|Cys|Ser|Leu|Ser|Gln|Gly|Thr|Leu|Gln|Trp|Ile|
|225| | | | |230| | | | |235| | | | |240|
|Glu|Asp|Thr|Leu|Tyr|Ala|Asn|Val|Asp|Phe|Phe|Lys|Leu|Phe|Arg|Val|
| | | | |245| | | | |250| | | | |255| |
|Leu|Pro|Thr|Leu|Leu|Asp|Ser|Arg|Ser|Gln|Gly|Ile|Asn|Leu|Arg|Ser|
| | | |260| | | | |265| | | | |270| | |
|Trp|Gly|Gly|Ile|Leu|Ser|Asp|Met|Ser|Pro|Arg|Ile|Gln|Glu|Phe|Ile|
| | |275| | | | |280| | | | |285| | | |
|His|Arg|Pro|Ser|Met|Gln|Asp|Leu|Leu|Trp|Val|Thr|Arg|Pro|Leu|Met|
| |290| | | | |295| | | | |300| | | | |
|Gln|Asn|Gly|Gly|Pro|Glu|Thr|Phe|Thr|Lys|Leu|Met|Gly|Ile|Leu|Ser|
|305| | | | |310| | | | |315| | | | |320|
|Asp|Leu|Leu|Cys|Gly|Tyr|Pro|Glu|Gly|Gly|Ser|Arg|Val|Leu|Ser|
| | | | |325| | | | |330| | | | |335| |
|Phe|Asn|Trp|Tyr|Glu|Asp|Asn|Asn|Tyr|Lys|Ala|Phe|Leu|Gly|Ile|Asp|
| | | |340| | | | |345| | | | |350| | |
|Ser|Thr|Arg|Lys|Asp|Pro|Ile|Tyr|Ser|Tyr|Asp|Arg|Arg|Thr|Thr|Ser|
| | |355| | | | |360| | | | |365| | | |
|Phe|Cys|Asn|Ala|Leu|Ile|Gln|Ser|Leu|Glu|Ser|Asn|Pro|Leu|Thr|Lys|
| |370| | | | |375| | | | |380| | | | |
|Ile|Ala|Trp|Arg|Ala|Ala|Lys|Pro|Leu|Leu|Met|Gly|Lys|Ile|Leu|Tyr|
|385| | | | |390| | | | |395| | | | |400|
|Thr|Pro|Asp|Ser|Pro|Ala|Ala|Arg|Arg|Ile|Leu|Lys|Asn|Ala|Asn|Ser|
| | | | |405| | | | |410| | | | |415| |

-continued

```
Thr Phe Glu Glu Leu Glu His Val Arg Lys Leu Val Lys Ala Trp Glu
            420                 425                 430

Glu Val Gly Pro Gln Ile Trp Tyr Phe Phe Asp Asn Ser Thr Gln Met
        435                 440                 445

Asn Met Ile Arg Asp Thr Leu Gly Asn Pro Thr Val Lys Asp Phe Leu
    450                 455                 460

Asn Arg Gln Leu Gly Glu Gly Ile Thr Ala Glu Ala Ile Leu Asn
465                 470                 475                 480

Phe Leu Tyr Lys Gly Pro Arg Glu Ser Gln Ala Asp Asp Met Ala Asn
                485                 490                 495

Phe Asp Trp Arg Asp Ile Phe Asn Ile Thr Asp Arg Thr Leu Arg Leu
            500                 505                 510

Val Asn Gln Tyr Leu Glu Cys Leu Val Leu Asp Lys Phe Glu Ser Tyr
        515                 520                 525

Asn Asp Glu Thr Gln Leu Thr Gln Arg Ala Leu Ser Leu Leu Glu Glu
    530                 535                 540

Asn Met Phe Trp Ala Gly Val Phe Pro Asp Met Tyr Pro Trp Thr
545                 550                 555                 560

Ser Ser Leu Pro Pro His Val Lys Tyr Lys Ile Arg Met Asp Ile Asp
                565                 570                 575

Val Val Glu Lys Thr Asn Lys Ile Lys Asp Arg Tyr Trp Asp Ser Gly
            580                 585                 590

Pro Arg Ala Asp Pro Val Glu Asp Phe Arg Tyr Ile Trp Gly Gly Phe
        595                 600                 605

Ala Tyr Leu Gln Asp Met Val Glu Gln Gly Ile Thr Arg Ser Gln Val
    610                 615                 620

Gln Ala Glu Ala Pro Val Gly Ile Tyr Leu Gln Gln Met Pro Tyr Pro
625                 630                 635                 640

Cys Phe Val Asp Asp Ser Phe Met Ile Ile Leu Asn Arg Cys Phe Pro
                645                 650                 655

Ile Phe Met Val Leu Ala Trp Ile Tyr Ser Val Ser Met Thr Val Lys
            660                 665                 670

Ser Ile Val Leu Glu Lys Glu Leu Arg Leu Lys Glu Thr Leu Lys Asn
        675                 680                 685

Gln Gly Val Ser Asn Ala Val Ile Trp Cys Thr Trp Phe Leu Asp Ser
    690                 695                 700

Phe Ser Ile Met Ser Met Ser Ile Phe Leu Leu Thr Ile Phe Ile Met
705                 710                 715                 720

His Gly Arg Ile Leu His Tyr Ser Asp Pro Phe Ile Leu Phe Leu Phe
                725                 730                 735

Leu Leu Ala Phe Ser Thr Ala Thr Ile Met Leu Cys Phe Leu Leu Ser
            740                 745                 750

Thr Phe Phe Ser Lys Ala Ser Leu Ala Ala Ala Cys Ser Gly Val Ile
        755                 760                 765

Tyr Phe Thr Leu Tyr Leu Pro His Ile Leu Cys Phe Ala Trp Gln Asp
    770                 775                 780

Arg Met Thr Ala Glu Leu Lys Lys Ala Val Ser Leu Leu Ser Pro Val
785                 790                 795                 800

Ala Phe Gly Phe Gly Thr Glu Tyr Leu Val Arg Phe Glu Glu Gln Gly
                805                 810                 815

Leu Gly Leu Gln Trp Ser Asn Ile Gly Asn Ser Pro Thr Glu Gly Asp
            820                 825                 830
```

-continued

```
Glu Phe Ser Phe Leu Leu Ser Met Gln Met Met Leu Leu Asp Ala Ala
    835                 840                 845
Cys Tyr Gly Leu Leu Ala Trp Tyr Leu Asp Gln Val Phe Pro Gly Asp
    850                 855                 860
Tyr Gly Thr Pro Leu Pro Trp Tyr Phe Leu Leu Gln Glu Ser Tyr Trp
865                 870                 875                 880
Leu Ser Gly Glu Gly Cys Ser Thr Arg Glu Arg Ala Leu Glu Lys
                885                 890                 895
Thr Glu Pro Leu Thr Glu Glu Thr Glu Asp Pro Glu His Pro Glu Gly
                900                 905                 910
Ile His Asp Ser Phe Phe Glu Arg Glu His Pro Gly Trp Val Pro Gly
        915                 920                 925
Val Cys Val Lys Asn Leu Val Lys Ile Phe Glu Pro Cys Gly Arg Pro
    930                 935                 940
Ala Val Asp Arg Leu Asn Ile Thr Phe Tyr Glu Asn Gln Ile Thr Ala
945                 950                 955                 960
Phe Leu Gly His Asn Gly Ala Gly Lys Thr Thr Thr Leu Ser Ile Leu
                965                 970                 975
Thr Gly Leu Leu Pro Pro Thr Ser Gly Thr Val Leu Val Gly Gly Arg
                980                 985                 990
Asp Ile Glu Thr Ser Leu Asp Ala Val Arg Gln Ser Leu Gly Met Cys
            995                 1000                1005
Pro Gln His Asn Ile Leu Phe His His Leu Thr Val Ala Glu His
    1010                1015                1020
Met Leu Phe Tyr Ala Gln Leu Lys Gly Lys Ser Gln Glu Glu Ala
    1025                1030                1035
Gln Leu Glu Met Glu Ala Met Leu Glu Asp Thr Gly Leu His His
    1040                1045                1050
Lys Arg Asn Glu Glu Ala Gln Asp Leu Ser Gly Gly Met Gln Arg
    1055                1060                1065
Lys Leu Ser Val Ala Ile Ala Phe Val Gly Asp Ala Lys Val Val
    1070                1075                1080
Ile Leu Asp Glu Pro Thr Ser Gly Val Asp Pro Tyr Ser Arg Arg
    1085                1090                1095
Ser Ile Trp Asp Leu Leu Leu Lys Tyr Arg Ser Gly Arg Thr Ile
    1100                1105                1110
Ile Met Pro Thr His His Met Asp Glu Ala Asp His Gln Gly Asp
    1115                1120                1125
Arg Ile Ala Ile Ile Ala Gln Gly Arg Leu Tyr Cys Ser Gly Thr
    1130                1135                1140
Pro Leu Phe Leu Lys Asn Cys Phe Gly Thr Gly Leu Tyr Leu Thr
    1145                1150                1155
Leu Val Arg Lys Met Lys Asn Ile Gln Ser Gln Arg Lys Gly Ser
    1160                1165                1170
Glu Gly Thr Cys Ser Cys Ser Ser Lys Gly Phe Ser Thr Thr Cys
    1175                1180                1185
Pro Ala His Val Asp Asp Leu Thr Pro Glu Gln Val Leu Asp Gly
    1190                1195                1200
Asp Val Asn Glu Leu Met Asp Val Val Leu His His Val Pro Glu
    1205                1210                1215
Ala Lys Leu Val Glu Cys Ile Gly Gln Glu Leu Ile Phe Leu Leu
    1220                1225                1230
Pro Asn Lys Asn Phe Lys His Arg Ala Tyr Ala Ser Leu Phe Arg
```

```
                          1235                    1240                    1245

Glu  Leu  Glu  Glu  Thr  Leu  Ala  Asp  Leu  Gly  Leu  Ser   Ser  Phe  Gly
                 1250                    1255                    1260

Ile  Ser  Asp  Thr  Pro  Leu  Glu  Ile  Phe  Leu  Lys  Val   Thr  Glu
                 1265                    1270                    1275

Asp  Ser  Asp  Ser  Gly  Pro  Leu  Phe  Ala  Gly  Gly  Ala   Gln  Gln  Lys
                 1280                    1285                    1290

Arg  Glu  Asn  Val  Asn  Pro  Arg  His  Pro  Cys  Leu  Gly   Pro  Arg  Glu
                 1295                    1300                    1305

Lys  Ala  Gly  Gln  Thr  Pro  Gln  Asp  Ser  Asn  Val  Cys   Ser  Pro  Gly
                 1310                    1315                    1320

Ala  Pro  Ala  Ala  His  Pro  Glu  Gly  Gln  Pro  Pro  Glu   Pro  Glu
                 1325                    1330                    1335

Cys  Pro  Gly  Pro  Gln  Leu  Asn  Thr  Gly  Thr  Gln  Leu   Val  Leu  Gln
                 1340                    1345                    1350

His  Val  Gln  Ala  Leu  Leu  Val  Lys  Arg  Phe  Gln  His   Thr  Ile  Arg
                 1355                    1360                    1365

Ser  His  Lys  Asp  Phe  Leu  Ala  Gln  Ile  Val  Leu  Pro   Ala  Thr  Phe
                 1370                    1375                    1380

Val  Phe  Leu  Ala  Leu  Met  Leu  Ser  Ile  Val  Ile  Leu   Pro  Phe  Gly
                 1385                    1390                    1395

Glu  Tyr  Pro  Ala  Leu  Thr  Leu  His  Pro  Trp  Ile  Tyr   Gly  Gln  Gln
                 1400                    1405                    1410

Tyr  Thr  Phe  Phe  Ser  Met  Asp  Glu  Pro  Gly  Ser  Glu   Gln  Phe  Thr
                 1415                    1420                    1425

Val  Leu  Ala  Asp  Val  Leu  Leu  Asn  Lys  Pro  Gly  Phe   Gly  Asn  Arg
                 1430                    1435                    1440

Cys  Leu  Lys  Glu  Gly  Trp  Leu  Pro  Glu  Tyr  Pro  Cys   Gly  Asn  Ser
                 1445                    1450                    1455

Thr  Pro  Trp  Lys  Thr  Pro  Ser  Val  Ser  Pro  Asn  Ile   Thr  Gln  Leu
                 1460                    1465                    1470

Phe  Gln  Lys  Gln  Lys  Trp  Thr  Gln  Val  Asn  Pro  Ser   Pro  Ser  Cys
                 1475                    1480                    1485

Arg  Cys  Ser  Thr  Arg  Glu  Lys  Leu  Thr  Met  Leu  Pro   Glu  Cys  Pro
                 1490                    1495                    1500

Glu  Gly  Ala  Gly  Gly  Leu  Pro  Pro  Pro  Gln  Arg  Thr   Gln  Arg  Ser
                 1505                    1510                    1515

Thr  Glu  Ile  Leu  Gln  Asp  Leu  Thr  Asp  Arg  Asn  Ile   Ser  Asp  Phe
                 1520                    1525                    1530

Leu  Val  Lys  Thr  Tyr  Pro  Ala  Leu  Ile  Arg  Ser  Ser   Leu  Lys  Ser
                 1535                    1540                    1545

Lys  Phe  Trp  Val  Asn  Glu  Gln  Arg  Tyr  Gly  Gly  Ile   Ser  Ile  Gly
                 1550                    1555                    1560

Gly  Lys  Leu  Pro  Val  Val  Pro  Ile  Thr  Gly  Glu  Ala   Leu  Val  Gly
                 1565                    1570                    1575

Phe  Leu  Ser  Asp  Leu  Gly  Arg  Ile  Met  Asn  Val  Ser   Gly  Gly  Pro
                 1580                    1585                    1590

Ile  Thr  Arg  Glu  Ala  Ser  Lys  Glu  Ile  Pro  Asp  Phe   Leu  Lys  His
                 1595                    1600                    1605

Leu  Glu  Thr  Glu  Asp  Asn  Ile  Lys  Val  Trp  Phe  Asn   Asn  Lys  Gly
                 1610                    1615                    1620

Trp  His  Ala  Leu  Val  Ser  Phe  Leu  Asn  Val  Ala  His   Asn  Ala  Ile
                 1625                    1630                    1635
```

-continued

```
Leu Arg Ala Ser Leu Pro Lys Asp Arg Ser Pro Glu Glu Tyr Gly
1640                1645                1650

Ile Thr Val Ile Ser Gln Pro Leu Asn Leu Thr Lys Glu Gln Leu
1655                1660                1665

Ser Glu Ile Thr Val Leu Thr Thr Ser Val Asp Ala Val Val Ala
1670                1675                1680

Ile Cys Val Ile Phe Ser Met Ser Phe Val Pro Ala Ser Phe Val
1685                1690                1695

Leu Tyr Leu Ile Gln Glu Arg Val Asn Lys Ser Lys His Leu Gln
1700                1705                1710

Phe Ile Ser Gly Val Ser Pro Thr Thr Tyr Trp Val Thr Asn Phe
1715                1720                1725

Leu Trp Asp Ile Met Asn Tyr Ser Val Ser Ala Gly Leu Val Val
1730                1735                1740

Gly Ile Phe Ile Gly Phe Gln Lys Lys Ala Tyr Thr Ser Pro Glu
1745                1750                1755

Asn Leu Pro Ala Leu Val Ala Leu Leu Leu Leu Tyr Gly Trp Ala
1760                1765                1770

Val Ile Pro Met Met Tyr Pro Ala Ser Phe Leu Phe Asp Val Pro
1775                1780                1785

Ser Thr Ala Tyr Val Ala Leu Ser Cys Ala Asn Leu Phe Ile Gly
1790                1795                1800

Ile Asn Ser Ser Ala Ile Thr Phe Ile Leu Glu Leu Phe Asp Asn
1805                1810                1815

Asn Arg Thr Leu Leu Arg Phe Asn Ala Val Leu Arg Lys Leu Leu
1820                1825                1830

Ile Val Phe Pro His Phe Cys Leu Gly Arg Gly Leu Ile Asp Leu
1835                1840                1845

Ala Leu Ser Gln Ala Val Thr Asp Val Tyr Ala Arg Phe Gly Glu
1850                1855                1860

Glu His Ser Ala Asn Pro Phe His Trp Asp Leu Ile Gly Lys Asn
1865                1870                1875

Leu Phe Ala Met Val Val Glu Gly Val Val Tyr Phe Leu Leu Thr
1880                1885                1890

Leu Leu Val Gln Arg His Phe Phe Leu Ser Gln Trp Ile Ala Glu
1895                1900                1905

Pro Thr Lys Glu Pro Ile Val Asp Glu Asp Asp Val Ala Glu
1910                1915                1920

Glu Arg Gln Arg Ile Ile Thr Gly Gly Asn Lys Thr Asp Ile Leu
1925                1930                1935

Arg Leu His Glu Leu Thr Lys Ile Tyr Leu Gly Thr Ser Ser Pro
1940                1945                1950

Ala Val Asp Arg Leu Cys Val Gly Val Arg Pro Gly Glu Cys Phe
1955                1960                1965

Gly Leu Leu Gly Val Asn Gly Ala Gly Lys Thr Thr Phe Lys
1970                1975                1980

Met Leu Thr Gly Asp Thr Thr Val Thr Ser Gly Asp Ala Thr Val
1985                1990                1995

Ala Gly Lys Ser Ile Leu Thr Asn Ile Ser Glu Val His Gln Asn
2000                2005                2010

Met Gly Tyr Cys Pro Gln Phe Asp Ala Ile Asp Glu Leu Leu Thr
2015                2020                2025
```

```
Gly Arg Glu His Leu Tyr Leu Tyr Ala Arg Leu Arg Gly Val Pro
    2030            2035            2040

Ala Glu Glu Ile Glu Lys Val Ala Asn Trp Ser Ile Lys Ser Leu
    2045            2050            2055

Gly Leu Thr Val Tyr Ala Asp Cys Leu Ala Gly Thr Tyr Ser Gly
    2060            2065            2070

Gly Asn Lys Arg Lys Leu Ser Thr Ala Ile Ala Leu Ile Gly Cys
    2075            2080            2085

Pro Pro Leu Val Leu Leu Asp Glu Pro Thr Thr Gly Met Asp Pro
    2090            2095            2100

Gln Ala Arg Arg Met Leu Trp Asn Val Ile Val Ser Ile Ile Arg
    2105            2110            2115

Lys Gly Arg Ala Val Val Leu Thr Ser His Ser Met Glu Glu Cys
    2120            2125            2130

Glu Ala Leu Cys Thr Arg Leu Ala Ile Met Val Lys Gly Ala Phe
    2135            2140            2145

Arg Cys Met Gly Thr Ile Gln His Leu Lys Ser Lys Phe Gly Asp
    2150            2155            2160

Gly Tyr Ile Val Thr Met Lys Ile Lys Ser Pro Lys Asp Asp Leu
    2165            2170            2175

Leu Pro Asp Leu Asn Pro Val Glu Gln Phe Phe Gln Gly Asn Phe
    2180            2185            2190

Pro Gly Ser Val Gln Arg Glu Arg His Tyr Asn Met Leu Gln Phe
    2195            2200            2205

Gln Val Ser Ser Ser Leu Ala Arg Ile Phe Gln Leu Leu Leu
    2210            2215            2220

Ser His Lys Asp Ser Leu Leu Ile Glu Glu Tyr Ser Val Thr Gln
    2225            2230            2235

Thr Thr Leu Asp Gln Val Phe Val Asn Phe Ala Lys Gln Gln Thr
    2240            2245            2250

Glu Ser His Asp Leu Pro Leu His Pro Arg Ala Ala Gly Ala Ser
    2255            2260            2265

Arg Gln Ala Gln Asp
    2270

<210> SEQ ID NO 4
<211> LENGTH: 114
<212> TYPE: DNA
<213> ORGANISM: Homo sapiens

<400> SEQUENCE: 4
ggagtacccc tgtggcaact caacaccctg gaagactcct tctgtgtccc caaacatcac    60
ccagctgttc cagaagcaga atggacaca ggtcaaccct tcaccatcct gcag          114

<210> SEQ ID NO 5
<211> LENGTH: 6705
<212> TYPE: DNA
<213> ORGANISM: Homo sapiens

<400> SEQUENCE: 5
atgggcttcg tgagacagat acagcttttg ctctggaaga actggaccct gcggaaaagg    60
caaaagattc gctttgtggt ggaactcgtg tggcctttat ctttatttct ggtcttgatc   120
tggttaagga atgccaaccc gctctacagc atcatgaat gccatttccc caacaaggcg   180
atgccctcag caggaatgct gccgtggctc caggggatct tctgcaatgt gaacaatccc   240
```

-continued

| | | | |
|---|---|---|---|
| tgttttcaaa | gccccacccc | aggagaatct cctggaattg | tgtcaaacta taacaactcc | 300 |
| atcttggcaa | gggtatatcg | agattttcaa gaactcctca | tgaatgcacc agagagccag | 360 |
| caccttggcc | gtatttggac | agagctacac atcttgtccc | aattcatgga caccctccgg | 420 |
| actcacccgg | agagaattgc | aggaagagga atacgaataa | gggatatctt gaaagatgaa | 480 |
| gaaacactga | cactatttct | cattaaaaac atcggcctgt | ctgactcagt ggtctacctt | 540 |
| ctgatcaact | ctcaagtccg | tccagagcag ttcgctcatg | gagtcccgga cctggcgctg | 600 |
| aaggacatcg | cctgcagcga | ggccctcctg gagcgcttca | tcatcttcag ccagagacgc | 660 |
| ggggcaaaga | cggtgcgcta | tgccctgtgc tccctctccc | agggcaccct acagtggata | 720 |
| gaagacactc | tgtatgccaa | cgtggacttc ttcaagctct | ccgtgtgct cccacactc | 780 |
| ctagacagcc | gttctcaagg | tatcaatctg agatcttggg | gaggaatatt atctgatatg | 840 |
| tcaccaagaa | ttcaagagtt | tatccatcgg ccgagtatgc | aggacttgct gtgggtgacc | 900 |
| aggcccctca | tgcagaatgg | tggtccagag acctttacaa | agctgatggg catcctgtct | 960 |
| gacctcctgt | gtggctaccc | cgagggaggt ggctctcggg | tgctctcctt caactggtat | 1020 |
| gaagacaata | actataaggc | ctttctgggg attgactcca | caaggaagga tcctatctat | 1080 |
| tcttatgaca | gaagaacaac | atccttttgt aatgcattga | tccagagcct ggagtcaaat | 1140 |
| cctttaacca | aaatcgcttg | gagggcggca aagcctttgc | tgatgggaaa aatcctgtac | 1200 |
| actcctgatt | cacctgcagc | acgaaggata ctgaagaatg | ccaactcaac ttttgaagaa | 1260 |
| ctggaacacg | ttaggaagtt | ggtcaaagcc tgggaagaag | tagggcccca gatctggtac | 1320 |
| ttctttgaca | cagcacaca | gatgaacatg atcagagata | ccctggggaa cccaacagta | 1380 |
| aaagacttt | tgaataggca | gcttggtgaa gaaggtatta | ctgctgaagc catcctaaac | 1440 |
| ttcctctaca | agggccctcg | ggaaagccag gctgacgaca | tggccaactt cgactggagg | 1500 |
| gacatattta | acatcactga | tcgcaccctc cgcctggtca | atcaatacct ggagtgcttg | 1560 |
| gtcctggata | agtttgaaag | ctacaatgat gaaactcagc | tcacccaacg tgccctctct | 1620 |
| ctactggagg | aaaacatgtt | ctgggccgga gtggtattcc | ctgacatgta tcctggacc | 1680 |
| agctctctac | caccccacgt | gaagtataag atccgaatgg | acatagacgt ggtggagaaa | 1740 |
| accaataaga | ttaaagacag | gtattgggat tctggtccca | gagctgatcc cgtggaagat | 1800 |
| ttccggtaca | tctggggcgg | gtttgcctat ctgcaggaca | tggttgaaca ggggatcaca | 1860 |
| aggagccagg | tgcaggcgga | ggctccagtt ggaatctacc | tccagcagat gcctacccc | 1920 |
| tgcttcgtgg | acgattcttt | catgatcatc ctgaaccgct | gttcctat cttcatggtg | 1980 |
| ctggcatgga | tctactctgt | ctccatgact gtgaagagca | tcgtcttgga aaggagttg | 2040 |
| cgactgaagg | agaccttgaa | aaatcagggt gtctccaatg | cagtgatttg gtgtacctgg | 2100 |
| ttcctggaca | gcttctccat | catgtcgatg agcatcttcc | tcctgacgat attcatcatg | 2160 |
| catggaagaa | tcctacatta | cagcgaccca ttcatcctct | tcctgttctt gttggctttc | 2220 |
| tccactgcca | ccatcatgct | gtgctttctg ctcagcacct | tcttctccaa ggccagtctg | 2280 |
| gcagcagcct | gtagtggtgt | catctatttc accctctacc | tgccacacat cctgtgcttc | 2340 |
| gcctggcagg | accgcatgac | gcgtgagctg aagaaggctg | tgagcttact gtctccggtg | 2400 |
| gcatttggat | ttggcactga | gtacctggtt cgctttgaag | agcaaggcct ggggctgcag | 2460 |
| tggagcaaca | tcgggaacag | tcccacggaa ggggacgaat | tcagcttcct gctgtccatg | 2520 |
| cagatgatgc | tccttgatgc | tgctgtctat ggcttactcg | cttggtacct tgatcaggtg | 2580 |
| tttccaggag | actatggaac | cccacttcct tggtactttc | ttctacaaga gtcgtattgg | 2640 |

```
cttggcggtg aagggtgttc aaccagagaa gaaagagccc tggaaaagac cgagccccta   2700
acagaggaaa cggaggatcc agagcaccca gaaggaatac acgactcctt ctttgaacgt   2760
gagcatccag ggtgggttcc tggggtatgc gtgaagaatc tggtaaagat ttttgagccc   2820
tgtggccggc cagctgtgga ccgtctgaac atcaccttct acgagaacca gatcaccgca   2880
ttcctgggcc acaatggagc tgggaaaacc accaccttgt ccatcctgac gggtctgttg   2940
ccaccaacct ctgggactgt gctcgttggg ggaagggaca ttgaaaccag cctggatgca   3000
gtccggcaga gccttggcat gtgtccacag cacaacatcc tgttccacca cctcacggtg   3060
gctgagcaca tgctgttcta tgcccagctg aaaggaaagt cccaggagga ggcccagctg   3120
gagatggaag ccatgttgga ggacacaggc ctccaccaca gcggaatgaa gaggctcag   3180 gacctatcag gtggcatgca gagaaagctg tcggttgcca ttgcctttgt gggagatgcc   3240
aaggtggtga ttctggacga acccacctct ggggtggacc cttactcgag acgctcaatc   3300
tgggatctgc tcctgaagta tcgctcaggc agaaccatca tcatgtccac tcaccacatg   3360
gacgaggccg acctccttgg ggaccgcatt gccatcattg cccagggaag gctctactgc   3420
tcaggcaccc cactcttcct gaagaactgc tttggcacag gcttgtactt aaccttggtg   3480
cgcaagatga aaaacatcca gagccaaagg aaaggcagtg aggggacctg cagctgctcg   3540
tctaagggtt tctccaccac gtgtccagcc cacgtcgatg acctaactcc agaacaagtc   3600
ctggatgggg atgtaaatga gctgatggat gtagttctcc accatgttcc agaggcaaag   3660
ctggtggagt gcattggtca agaacttatc ttccttcttc caaataagaa cttcaagcac   3720
agagcatatg ccagccttt cagagagctg gaggagacgc tggctgacct tggtctcagc   3780
agttttggaa tttctgacac tccctggaa gagatttttc tgaaggtcac ggaggattct   3840
gattcaggac tctgtttgc gggtggcgct cagcagaaaa gagaaaacgt caaccccga   3900 caccctgct tgggtcccag agagaaggct ggacagacac cccaggactc caatgtctgc   3960
tccccagggg cgccggctgc tcacccagag ggccagcctc ccccagagcc agagtgccca   4020
ggcccgcagc tcaacacggg gacacagctg gtcctccagc atgtgcaggc gctgctggtc   4080
aagagattcc aacacaccat ccgcagccac aaggacttcc tggcgcagat cgtgctcccg   4140
gctacctttg tgtttttggc tctgatgctt tctattgtta tccctccttt tggcgaatac   4200
cccgctttga cccttcaccc ctggatatat gggcagcagt acaccttctt cagcatggat   4260
gaaccaggca gtgagcagtt cacggtactt gcagacgtcc tcctgaataa gccaggcttt   4320
ggcaaccgct gcctgaagga agggtggctt ccgtgcagca ccaggagaa gctcaccatg   4380 ctgccagagt gccccgaggg tgccgggggc ctcccgcccc cccagagaac acagcgcagc   4440
acggaaattc tacaagacct gacggacagg aacatctccg acttcttggt aaaaacgtat   4500
cctgctctta taagaagcag cttaaagagc aaattctggg tcaatgaaca gaggtatgga   4560
ggaatttcca ttggaggaaa gctcccagtc gtccccatca cggggaagc acttgttggg   4620 tttttaagcg accttggccg gatcatgaat gtgagcgggg gccctatcac tagagaggcc   4680
tctaaagaaa tacctgattt ccttaaacat ctagaaactg aagcaacat taaggtgtgg   4740 tttaataaca aaggctggca tgccctggtc agctttctca atgtggccca aacgccatc   4800 ttacgggcca gcctgcctaa ggacaggagc cccgaggagt atggaatcac cgtcattagc   4860
caacccctga acctgaccaa ggagcagctc tcagagatta cagtgctgac cacttcagtg   4920
gatgctgtgg ttgccatctg cgtgattttc tccatgtcct tcgtcccagc cagctttgtc   4980
```

-continued

```
cttatttga tccaggagcg ggtgaacaaa tccaagcacc tccagtttat cagtggagtg    5040
agccccacca cctactgggt gaccaacttc ctctgggaca tcatgaatta ttccgtgagt    5100
gctgggctgg tggtgggcat cttcatcggg tttcagaaga agcctacac ttctccagaa    5160 aaccttcctg cccttgtggc actgctcctg ctgtatggat gggcggtcat tcccatgatg    5220
tacccagcat ccttcctgtt tgatgtcccc agcacagcct atgtggcttt atcttgtgct    5280
aatctgttca tcggcatcaa cagcagtgct attaccttca tcttggaatt atttgagaat    5340
aaccggacgc tgctcaggtt caacgccgtg ctgaggaagc tgctcattgt cttcccccac    5400
ttctgcctgg gccggggcct cattgacctt gcactgagcc aggctgtgac agatgtctat    5460
gcccggtttg gtgaggagca ctctgcaaat ccgttccact gggacctgat tgggaagaac    5520
ctgtttgcca tggtggtgga aggggtggtg tacttcctcc tgaccctgct ggtccagcgc    5580
cacttcttcc tctcccaatg gattgccgag cccactaagg agcccattgt tgatgaagat    5640
gatgatgtgg ctgaagaaag acaaagaatt attactggtg gaaataaaac tgacatctta    5700
aggctacatg aactaaccaa gatttatcca ggcacctcca gcccagcagt ggacaggctg    5760
tgtgtcggag ttcgccctgg agagtgcttt ggcctcctgg gagtgaatgg tgccggcaaa    5820
acaaccacat tcaagatgct cactggggac accacagtga cctcagggga tgccaccgta    5880
gcaggcaaga gtattttaac caatatttct gaagtccatc aaaatatggg ctactgtcct    5940
cagtttgatg caatcgatga gctgctcaca ggacgagaac atctttacct ttatgcccgg    6000
cttcgaggtg taccagcaga agaaatcgaa aaggttgcaa actggagtat taagagcctg    6060
ggcctgactg tctacgccga ctgcctggct ggcacgtaca gtgggggcaa caagcggaaa    6120
ctctccacag ccatcgcact cattggctgc ccaccgctgg tgctgctgga tgagcccacc    6180
acagggatgg acccccaggc acgccgcatg ctgtggaacg tcatcgtgag catcatcaga    6240
gaagggaggg ctgtggtcct cacatcccac agcatgaagg aatgtgaggc actgtgtacc    6300
cggctggcca tcatggtaaa gggcgccttt cgatgtatgg gcaccattca gcatctcaag    6360
tccaaatttg gagatggcta tatcgtcaca atgaagatca aatccccgaa ggacgacctg    6420
cttcctgacc tgaaccctgt ggagcagttc ttccagggga acttcccagg cagtgtgcag    6480
agggagaggc actacaacat gctccagttc caggtctcct cctcctccct ggcgaggatc    6540
ttccagctcc tcctctccca caaggacagc ctgctcatcg aggagtactc agtcacacag    6600
accacactgg accaggtgtt tgtaaatttt gctaaacagc agactgaaag tcatgacctc    6660
cctctgcacc ctcgagctgc tggagccagt cgacaagccc aggac                    6705
```

<210> SEQ ID NO 6
<211> LENGTH: 2235
<212> TYPE: PRT
<213> ORGANISM: Homo sapiens

<400> SEQUENCE: 6

```
Met Gly Phe Val Arg Gln Ile Gln Leu Leu Leu Trp Lys Asn Trp Thr
1               5                   10                  15

Leu Arg Lys Arg Gln Lys Ile Arg Phe Val Val Glu Leu Val Trp Pro
            20                  25                  30

Leu Ser Leu Phe Leu Val Leu Ile Trp Leu Arg Asn Ala Asn Pro Leu
        35                  40                  45

Tyr Ser His His Glu Cys His Phe Pro Asn Lys Ala Met Pro Ser Ala
    50                  55                  60

Gly Met Leu Pro Trp Leu Gln Gly Ile Phe Cys Asn Val Asn Asn Pro
```

-continued

```
            65                  70                  75                  80
Cys Phe Gln Ser Pro Thr Pro Gly Glu Ser Pro Gly Ile Val Ser Asn
                     85                  90                  95

Tyr Asn Asn Ser Ile Leu Ala Arg Val Tyr Arg Asp Phe Gln Glu Leu
                    100                 105                 110

Leu Met Asn Ala Pro Glu Ser Gln His Leu Gly Arg Ile Trp Thr Glu
                    115                 120                 125

Leu His Ile Leu Ser Gln Phe Met Asp Thr Leu Arg Thr His Pro Glu
                    130                 135                 140

Arg Ile Ala Gly Arg Gly Ile Arg Ile Arg Asp Ile Leu Lys Asp Glu
145                 150                 155                 160

Glu Thr Leu Thr Lys Phe Leu Ile Lys Asn Ile Gly Leu Ser Asp Ser
                    165                 170                 175

Val Val Tyr Leu Leu Ile Asn Ser Gln Val Arg Pro Glu Gln Phe Ala
                    180                 185                 190

His Gly Val Pro Asp Leu Ala Leu Lys Asp Ile Ala Cys Ser Glu Ala
                    195                 200                 205

Leu Leu Glu Arg Phe Ile Ile Phe Ser Gln Arg Gly Ala Lys Thr
                    210                 215                 220

Val Arg Tyr Ala Lys Cys Ser Leu Ser Gln Gly Thr Leu Gln Trp Ile
225                 230                 235                 240

Glu Asp Thr Leu Tyr Ala Asn Val Asp Phe Phe Lys Leu Phe Arg Val
                    245                 250                 255

Leu Pro Thr Leu Leu Asp Ser Arg Ser Gln Gly Ile Asn Leu Arg Ser
                    260                 265                 270

Trp Gly Gly Ile Leu Ser Asp Met Ser Pro Arg Ile Gln Glu Phe Ile
                    275                 280                 285

His Arg Pro Ser Met Gln Asp Leu Leu Trp Val Thr Arg Pro Leu Met
                    290                 295                 300

Gln Asn Gly Gly Pro Glu Thr Phe Thr Lys Leu Met Gly Ile Leu Ser
305                 310                 315                 320

Asp Leu Leu Cys Gly Tyr Pro Glu Gly Gly Ser Arg Val Leu Ser
                    325                 330                 335

Phe Asn Trp Tyr Glu Asp Asn Asn Tyr Lys Ala Phe Leu Gly Ile Asp
                    340                 345                 350

Ser Thr Arg Lys Asp Pro Ile Tyr Ser Tyr Asp Arg Arg Thr Thr Ser
                    355                 360                 365

Phe Cys Asn Ala Leu Ile Gln Ser Leu Glu Ser Asn Pro Leu Thr Lys
                    370                 375                 380

Ile Ala Trp Arg Ala Ala Lys Pro Leu Leu Met Gly Lys Ile Leu Tyr
385                 390                 395                 400

Thr Pro Asp Ser Pro Ala Ala Arg Arg Ile Leu Lys Asn Ala Asn Ser
                    405                 410                 415

Thr Phe Glu Glu Leu Glu His Val Arg Lys Leu Val Lys Ala Trp Glu
                    420                 425                 430

Glu Val Gly Pro Gln Ile Trp Tyr Phe Asp Asn Ser Thr Gln Met
                    435                 440                 445

Asn Met Ile Arg Asp Thr Leu Gly Asn Pro Thr Val Lys Asp Phe Leu
                    450                 455                 460

Asn Arg Gln Leu Gly Glu Gly Ile Thr Ala Glu Ile Leu Asn
465                 470                 475                 480

Phe Leu Tyr Lys Gly Pro Arg Glu Ser Gln Ala Asp Asp Met Ala Asn
                    485                 490                 495
```

-continued

```
Phe Asp Trp Arg Asp Ile Phe Asn Ile Thr Asp Arg Thr Leu Arg Leu
            500                 505                 510
Val Asn Gln Tyr Leu Glu Cys Leu Val Leu Asp Lys Phe Glu Ser Tyr
            515                 520                 525
Asn Asp Glu Thr Gln Leu Thr Gln Arg Ala Leu Ser Leu Leu Glu Glu
            530                 535                 540
Asn Met Phe Trp Ala Gly Val Val Phe Pro Asp Met Tyr Pro Trp Thr
545                 550                 555                 560
Ser Ser Leu Pro Pro His Val Lys Tyr Lys Ile Arg Met Asp Ile Asp
            565                 570                 575
Val Val Glu Lys Thr Asn Lys Ile Lys Asp Arg Tyr Trp Asp Ser Gly
            580                 585                 590
Pro Arg Ala Asp Pro Val Glu Asp Phe Arg Tyr Ile Trp Gly Gly Phe
            595                 600                 605
Ala Tyr Leu Gln Asp Met Val Glu Gln Gly Ile Thr Arg Ser Gln Val
            610                 615                 620
Gln Ala Glu Ala Pro Val Gly Ile Tyr Leu Gln Gln Met Pro Tyr Pro
625                 630                 635                 640
Cys Phe Val Asp Asp Ser Phe Met Ile Ile Leu Asn Arg Cys Phe Pro
                645                 650                 655
Ile Phe Met Val Leu Ala Trp Ile Tyr Ser Val Ser Met Thr Val Lys
            660                 665                 670
Ser Ile Val Leu Glu Lys Glu Leu Arg Leu Lys Glu Thr Leu Lys Asn
            675                 680                 685
Gln Gly Val Ser Asn Ala Val Ile Trp Cys Thr Trp Phe Leu Asp Ser
690                 695                 700
Phe Ser Ile Met Ser Met Ser Ile Phe Leu Leu Thr Ile Phe Ile Met
705                 710                 715                 720
His Gly Arg Ile Leu His Tyr Ser Asp Pro Phe Ile Leu Phe Leu Phe
            725                 730                 735
Leu Leu Ala Phe Ser Thr Ala Thr Ile Met Leu Cys Phe Leu Leu Ser
            740                 745                 750
Thr Phe Phe Ser Lys Ala Ser Leu Ala Ala Ala Cys Ser Gly Val Ile
            755                 760                 765
Tyr Phe Thr Leu Tyr Leu Pro His Ile Leu Cys Phe Ala Trp Gln Asp
770                 775                 780
Arg Met Thr Ala Glu Leu Lys Lys Ala Val Ser Leu Leu Ser Pro Val
785                 790                 795                 800
Ala Phe Gly Phe Gly Thr Glu Tyr Leu Val Arg Phe Glu Glu Gln Gly
                805                 810                 815
Leu Gly Leu Gln Trp Ser Asn Ile Gly Asn Ser Pro Thr Glu Gly Asp
            820                 825                 830
Glu Phe Ser Phe Leu Leu Ser Met Gln Met Met Leu Leu Asp Ala Ala
            835                 840                 845
Val Tyr Gly Leu Leu Ala Trp Tyr Leu Asp Gln Val Phe Pro Gly Asp
            850                 855                 860
Tyr Gly Thr Pro Leu Pro Trp Tyr Phe Leu Leu Gln Glu Ser Tyr Trp
865                 870                 875                 880
Leu Gly Gly Glu Gly Cys Ser Thr Arg Glu Glu Arg Ala Leu Glu Lys
                885                 890                 895
Thr Glu Pro Leu Thr Glu Thr Glu Asp Pro Glu His Pro Glu Gly
            900                 905                 910
```

-continued

```
Ile His Asp Ser Phe Phe Glu Arg Glu His Pro Gly Trp Val Pro Gly
        915                 920                 925
Val Cys Val Lys Asn Leu Val Lys Ile Phe Glu Pro Cys Gly Arg Pro
        930                 935                 940
Ala Val Asp Arg Leu Asn Ile Thr Phe Tyr Glu Asn Gln Ile Thr Ala
945                 950                 955                 960
Phe Leu Gly His Asn Gly Ala Gly Lys Thr Thr Thr Leu Ser Ile Leu
                965                 970                 975
Thr Gly Leu Leu Pro Pro Thr Ser Gly Thr Val Leu Val Gly Gly Arg
            980                 985                 990
Asp Ile Glu Thr Ser Leu Asp Ala Val Arg Gln Ser Leu Gly Met Cys
        995                 1000                1005
Pro Gln His Asn Ile Leu Phe His His Leu Thr Val Ala Glu His
    1010                1015                1020
Met Leu Phe Tyr Ala Gln Leu Lys Gly Lys Ser Gln Glu Glu Ala
    1025                1030                1035
Gln Leu Glu Met Glu Ala Met Leu Glu Asp Thr Gly Leu His His
    1040                1045                1050
Lys Arg Asn Glu Glu Ala Gln Asp Leu Ser Gly Gly Met Gln Arg
    1055                1060                1065
Lys Leu Ser Val Ala Ile Ala Phe Val Gly Asp Ala Lys Val Val
    1070                1075                1080
Ile Leu Asp Glu Pro Thr Ser Gly Val Asp Pro Tyr Ser Arg Arg
    1085                1090                1095
Ser Ile Trp Asp Leu Leu Leu Lys Tyr Arg Ser Gly Arg Thr Ile
    1100                1105                1110
Ile Met Ser Thr His His Met Asp Glu Ala Asp Leu Leu Gly Asp
    1115                1120                1125
Arg Ile Ala Ile Ile Ala Gln Gly Arg Leu Tyr Cys Ser Gly Thr
    1130                1135                1140
Pro Leu Phe Leu Lys Asn Cys Phe Gly Thr Gly Leu Tyr Leu Thr
    1145                1150                1155
Leu Val Arg Lys Met Lys Asn Ile Gln Ser Gln Arg Lys Gly Ser
    1160                1165                1170
Glu Gly Thr Cys Ser Cys Ser Ser Lys Gly Phe Ser Thr Thr Cys
    1175                1180                1185
Pro Ala His Val Asp Asp Leu Thr Pro Glu Gln Val Leu Asp Gly
    1190                1195                1200
Asp Val Asn Glu Leu Met Asp Val Val Leu His His Val Pro Glu
    1205                1210                1215
Ala Lys Leu Val Glu Cys Ile Gly Gln Glu Leu Ile Phe Leu Leu
    1220                1225                1230
Pro Asn Lys Asn Phe Lys His Arg Ala Tyr Ala Ser Leu Phe Arg
    1235                1240                1245
Glu Leu Glu Glu Thr Leu Ala Asp Leu Gly Leu Ser Ser Phe Gly
    1250                1255                1260
Ile Ser Asp Thr Pro Leu Glu Glu Ile Phe Leu Lys Val Thr Glu
    1265                1270                1275
Asp Ser Asp Ser Gly Pro Leu Phe Ala Gly Gly Ala Gln Gln Lys
    1280                1285                1290
Arg Glu Asn Val Asn Pro Arg His Pro Cys Leu Gly Pro Arg Glu
    1295                1300                1305
Lys Ala Gly Gln Thr Pro Gln Asp Ser Asn Val Cys Ser Pro Gly
```

-continued

```
         1310              1315                1320

Ala Pro  Ala Ala His Pro  Glu Gly Gln  Pro Pro  Glu Pro Glu
    1325              1330              1335

Cys Pro  Gly Pro Gln Leu  Asn Thr Gly  Thr Gln  Leu Val Leu Gln
    1340              1345              1350

His Val  Gln Ala Leu Leu  Val Lys Arg  Phe Gln  His Thr Ile Arg
    1355              1360              1365

Ser His  Lys Asp Phe Leu  Ala Gln Ile  Val Leu  Pro Ala Thr Phe
    1370              1375              1380

Val Phe  Leu Ala Leu Met  Leu Ser Ile  Val Ile  Pro Pro Phe Gly
    1385              1390              1395

Glu Tyr  Pro Ala Leu Thr  Leu His Pro  Trp Ile  Tyr Gly Gln Gln
    1400              1405              1410

Tyr Thr  Phe Phe Ser Met  Asp Glu Pro  Gly Ser  Glu Gln Phe Thr
    1415              1420              1425

Val Leu  Ala Asp Val Leu  Leu Asn Lys  Pro Gly  Phe Gly Asn Arg
    1430              1435              1440

Cys Leu  Lys Glu Gly Trp  Leu Pro Cys  Ser Thr  Arg Glu Lys Leu
    1445              1450              1455

Thr Met  Leu Pro Glu Cys  Pro Glu Gly  Ala Gly  Gly Leu Pro Pro
    1460              1465              1470

Pro Gln  Arg Thr Gln Arg  Ser Thr Glu  Ile Leu  Gln Asp Leu Thr
    1475              1480              1485

Asp Arg  Asn Ile Ser Asp  Phe Leu Val  Lys Thr  Tyr Pro Ala Leu
    1490              1495              1500

Ile Arg  Ser Ser Leu Lys  Ser Lys Phe  Trp Val  Asn Glu Gln Arg
    1505              1510              1515

Thr Gly  Gly Ile Ser Ile  Gly Gly Lys  Leu Pro  Val Val Pro Ile
    1520              1525              1530

Thr Gly  Glu Ala Leu Val  Gly Phe Leu  Ser Asp  Leu Gly Arg Ile
    1535              1540              1545

Met Asn  Val Ser Gly Gly  Pro Ile Thr  Arg Glu  Ala Ser Lys Glu
    1550              1555              1560

Ile Pro  Asp Phe Leu Lys  His Leu Glu  Thr Glu  Asp Asn Ile Lys
    1565              1570              1575

Val Trp  Phe Asn Asn Lys  Gly Trp His  Ala Leu  Val Ser Phe Leu
    1580              1585              1590

Asn Val  Ala His Asn Ala  Ile Leu Arg  Ala Ser  Leu Pro Lys Asp
    1595              1600              1605

Arg Ser  Pro Glu Glu Tyr  Gly Ile Thr  Val Ile  Ser Gln Pro Leu
    1610              1615              1620

Asn Leu  Thr Lys Glu Gln  Leu Ser Glu  Ile Thr  Val Leu Thr Thr
    1625              1630              1635

Ser Val  Asp Ala Val Val  Ala Ile Cys  Val Ile  Phe Ser Met Ser
    1640              1645              1650

Phe Val  Pro Ala Ser Phe  Val Leu Tyr  Leu Ile  Gln Glu Arg Val
    1655              1660              1665

Asn Lys  Ser Lys His Leu  Gln Phe Ile  Ser Gly  Val Ser Pro Thr
    1670              1675              1680

Thr Tyr  Trp Val Thr Asn  Phe Leu Trp  Ser Ile  Met Asn Tyr Ser
    1685              1690              1695

Val Ser  Ala Gly Leu Val  Val Gly Ile  Phe Ile  Gly Phe Gln Lys
    1700              1705              1710
```

-continued

```
Lys Ala Tyr Thr Ser Pro Glu Asn Leu Pro Ala Leu Val Ala Leu
1715                1720                1725
Leu Leu Leu Tyr Gly Trp Ala Val Ile Pro Met Met Tyr Pro Ala
1730                1735                1740
Ser Phe Leu Phe Asp Val Pro Ser Thr Ala Tyr Val Ala Leu Ser
1745                1750                1755
Cys Ala Asn Leu Phe Ile Gly Ile Asn Ser Ser Ala Ile Thr Phe
1760                1765                1770
Ile Leu Glu Leu Phe Glu Asn Asn Arg Thr Leu Leu Arg Phe Asn
1775                1780                1785
Ala Val Leu Arg Lys Leu Leu Ile Val Phe Pro His Phe Cys Leu
1790                1795                1800
Gly Arg Gly Leu Ile Asp Leu Ala Leu Ser Gln Ala Val Thr Asp
1805                1810                1815
Val Tyr Ala Arg Phe Gly Glu Glu His Ser Ala Asn Pro Phe His
1820                1825                1830
Trp Asp Leu Ile Gly Lys Asn Leu Phe Ala Met Val Val Glu Gly
1835                1840                1845
Val Val Tyr Phe Leu Leu Thr Leu Leu Val Gln Arg His Phe Phe
1850                1855                1860
Leu Ser Gln Trp Ile Ala Glu Pro Thr Lys Glu Pro Ile Val Asp
1865                1870                1875
Glu Asp Asp Val Ala Glu Arg Gln Arg Ile Ile Thr Gly
1880                1885                1890
Gly Asn Lys Thr Asp Ile Leu Arg Leu His Glu Leu Thr Lys Ile
1895                1900                1905
Tyr Pro Gly Thr Ser Ser Pro Ala Val Asp Arg Leu Cys Val Gly
1910                1915                1920
Val Arg Pro Gly Glu Cys Phe Gly Leu Leu Gly Val Asn Gly Ala
1925                1930                1935
Gly Lys Thr Thr Thr Phe Lys Met Leu Thr Gly Asp Thr Thr Val
1940                1945                1950
Thr Ser Gly Asp Ala Thr Val Ala Gly Lys Ser Ile Leu Thr Asn
1955                1960                1965
Ile Ser Glu Val His Gln Asn Met Gly Tyr Cys Pro Gln Phe Asp
1970                1975                1980
Ala Ile Asp Glu Leu Leu Thr Gly Arg Glu His Leu Tyr Leu Tyr
1985                1990                1995
Ala Arg Leu Arg Gly Val Pro Ala Glu Glu Ile Glu Lys Leu Ala
2000                2005                2010
Asn Trp Ser Ile Lys Ser Leu Gly Leu Thr Val Tyr Ala Asp Cys
2015                2020                2025
Leu Ala Gly Thr Tyr Ser Gly Gly Asn Lys Arg Lys Leu Ser Thr
2030                2035                2040
Ala Ile Ala Leu Ile Gly Cys Pro Pro Leu Val Leu Leu Asp Glu
2045                2050                2055
Pro Thr Thr Gly Met Asp Pro Gln Ala Arg Arg Met Leu Trp Asn
2060                2065                2070
Val Ile Val Ser Ile Ile Arg Glu Gly Arg Ala Val Val Leu Thr
2075                2080                2085
Ser His Ser Met Glu Glu Cys Glu Ala Leu Cys Thr Arg Leu Ala
2090                2095                2100
```

```
Ile Met Val Lys Gly Ala Phe Arg Cys Met Gly Thr Ile Gln His
    2105                2110                2115
Leu Lys Ser Lys Phe Gly Asp Gly Tyr Ile Val Thr Met Lys Ile
    2120                2125                2130
Lys Ser Pro Lys Asp Asp Leu Leu Pro Asp Leu Asn Pro Val Glu
    2135                2140                2145
Gln Phe Phe Gln Gly Asn Phe Pro Gly Ser Val Gln Arg Glu Arg
    2150                2155                2160
His Tyr Asn Met Leu Gln Phe Gln Val Ser Ser Ser Leu Ala
    2165                2170                2175
Arg Ile Phe Gln Leu Leu Leu Ser His Lys Asp Ser Leu Leu Ile
    2180                2185                2190
Glu Glu Tyr Ser Val Thr Gln Thr Thr Leu Asp Gln Val Phe Val
    2195                2200                2205
Asn Phe Ala Lys Gln Gln Thr Glu Ser His Asp Leu Pro Leu His
    2210                2215                2220
Pro Arg Ala Ala Gly Ala Ser Arg Gln Ala Gln Asp
    2225                2230                2235
```

<210> SEQ ID NO 7
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 7
atcctctgac tcagcaatca ca                                    22

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 8
ttgcaattac aaatgcaatg g                                     21

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 9
atccataccc ttcccactcc                                       20

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 10
gcagcagaag ataagcacac c                                     21

<210> SEQ ID NO 11
<211> LENGTH: 38
<212> TYPE: PRT

<213> ORGANISM: Homo sapiens

<400> SEQUENCE: 11

Glu Tyr Pro Cys Gly Asn Ser Thr Pro Trp Lys Thr Pro Ser Val Ser
1               5                   10                  15

Pro Asn Ile Thr Gln Leu Phe Gln Lys Gln Lys Trp Thr Gln Val Asn
            20                  25                  30

Pro Ser Pro Ser Cys Arg
        35

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 12
accctctgct aagctcagag                                            20

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 13
accccacact tccaacctg                                             19

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
aagtcctact gcacacatgg                                            20

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 15
acactcccac cccaagatc                                             19

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 16
ttcccaaaaa ggccaactc                                             19

<210> SEQ ID NO 17
<211> LENGTH: 19
<212> TYPE: DNA
<213> ORGANISM: Artificial Sequence
<220> FEATURE:

```
<223> OTHER INFORMATION: Oligonucleotide primer

<400> SEQUENCE: 17
cacgcacgtg tgcattcag                                              19

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 18
gctatttcct tattaatgag gc                                          22

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
ccaactctcc ctgttctttc                                             20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
tgtttccaat cgactctggc                                             20

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 21
ttcttgcctt tctcaggctg g                                           21

<210> SEQ ID NO 22
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 22
gtattcccag gttctgtgg                                              19

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 23
taccccagga atcaccttg                                              19
```

-continued

```
<210> SEQ ID NO 24
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 24
agcatatagg agatcagact g                                                 21

<210> SEQ ID NO 25
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 25
tgacataagt ggggtaaatg g                                                 21

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
gagcattggc ctcacagcag                                                   20

<210> SEQ ID NO 27
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 27
ccccaggttt gtttcacc                                                     18

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 28
agacatgtga tgtggataca c                                                 21

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 29
gtgggaggtc cagggtacac                                                   20

<210> SEQ ID NO 30
<211> LENGTH: 19
<212> TYPE: DNA
<213> ORGANISM: Artificial Sequence
<220> FEATURE:
<223> OTHER INFORMATION: Oligonucleotide primer
```

-continued

```
<400> SEQUENCE: 30
aggggcagaa aagacacac                                                    19

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 31
tagcgattaa ctctttcctg g                                                 21

<210> SEQ ID NO 32
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 32
ctcttcaggg agccttagc                                                    19

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 33
ttcaagacca cttgacttgc                                                   20

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 34
tgggacagca gccttatc                                                     18

<210> SEQ ID NO 35
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 35
ccaaatgtaa tttcccactg ac                                                22

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 36
aatgagttcc gagtcaccct g                                                 21

<210> SEQ ID NO 37
<211> LENGTH: 18
```

```
<212> TYPE: DNA
<213> ORGANISM: Artificial Sequence
<220> FEATURE:
<223> OTHER INFORMATION: Oligonucleotide primer

<400> SEQUENCE: 37
cccattcgcg tgtcatgg                                                18

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 38
tccatctggg ctttgttctc                                              20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
aatccaggca catgaacagg                                              20

<210> SEQ ID NO 40
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 40
aggctggtgg gagagagc                                                18

<210> SEQ ID NO 41
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 41
agtggacccc ctcagagg                                                18

<210> SEQ ID NO 42
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 42
ctgttgcatt ggataaaagg c                                            21

<210> SEQ ID NO 43
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 43
```

-continued gatgaatgga gagggctgg                                          19

<210> SEQ ID NO 44
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 44
ctgcggtaag gtaggatagg g                                       21

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 45
cacaccgttt acatagaggg c                                       21

<210> SEQ ID NO 46
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 46
cctctcccct cctttcctg                                          19

<210> SEQ ID NO 47
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 47
gtcagtttcc gtaggcttc                                          19

<210> SEQ ID NO 48
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 48
tggggccatg taattaggc                                          19

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 49
tgggaaagag tagacagccg                                         20

<210> SEQ ID NO 50
<211> LENGTH: 18
<212> TYPE: DNA
<213> ORGANISM: Artificial Sequence

```
<220> FEATURE:
<223> OTHER INFORMATION: Oligonucleotide primer

<400> SEQUENCE: 50
actgaacctg gtgtgggg                                                 18

<210> SEQ ID NO 51
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 51
tatctctgcc tgtgcccag                                                19

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 52
gtaagatcag ctgctggaag                                               20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 53
gaagctctcc tgcaccaagc                                               20

<210> SEQ ID NO 54
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 54 aggtacccccc acaatgcc                                                18

<210> SEQ ID NO 55
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 55
tcattgtggt tccagtactc ag                                            22

<210> SEQ ID NO 56
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 56
tttttgcaac tatatagcca gg                                            22
```

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 57
agcctgtgtg agtagccatg                                                    20

<210> SEQ ID NO 58
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 58
gcatcagggc gaggctgtc                                                     19

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 59
cccagcaata ctgggagatg                                                    20

<210> SEQ ID NO 60
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 60
ggtaacctca cagtcttcc                                                     19

<210> SEQ ID NO 61
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 61
gggaacgatg gcttttttgc                                                    19

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 62
tcccattatg aagcaatacc                                                    20

<210> SEQ ID NO 63
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 63
ccttagactt tcgagatgg                                                       19

<210> SEQ ID NO 64
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 64
gctaccagcc tggtatttca ttg                                                  23

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 65
gttataaccc atgcctgaag                                                      20

<210> SEQ ID NO 66
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 66
tgcacgcgca cgtgtgac                                                        18

<210> SEQ ID NO 67
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 67
tgaaggtccc agtgaagtgg g                                                    21

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
cagcagctat ccagtaaagg                                                      20

<210> SEQ ID NO 69
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 69
aacgcctgcc atcttgaac                                                       19

<210> SEQ ID NO 70

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 70
gttgggcaca attcttatgc                                                    20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 71
gttgtttgga ggtcaggtac                                                    20

<210> SEQ ID NO 72
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 72
aacatcaccc agctgttcca g                                                  21

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 73
actcaggaga taccagggac                                                    20

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 74
ggaagacaac aagcagtttc ac                                                 22

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 75
atctactgcc ctgatcatac                                                    20

<210> SEQ ID NO 76
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 76
```
aagactgaga cttcagtctt c						21

<210> SEQ ID NO 77
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 77
ggtgtgcctt ttaaaagtgt gc					22

<210> SEQ ID NO 78
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 78
ttcatgtttc cctacaaaac cc					22

<210> SEQ ID NO 79
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 79
catgagagtt tctcattcat gg					22

<210> SEQ ID NO 80
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 80
tgtttacatg gttttaggg cc					22

<210> SEQ ID NO 81
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 81
ttcagcagga ggagggatg					19

<210> SEQ ID NO 82
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 82
cctttccttc actgatttct gc					22

<210> SEQ ID NO 83
<211> LENGTH: 18
<212> TYPE: DNA

```
<213> ORGANISM: Artificial Sequence
<220> FEATURE:
<223> OTHER INFORMATION: Oligonucleotide primer

<400> SEQUENCE: 83
aatcagcact tcgcggtg                                              18

<210> SEQ ID NO 84
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 84
tgtaaggcct tcccaaagc                                             19

<210> SEQ ID NO 85
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 85
tggtccttca gcgcacacac                                            20

<210> SEQ ID NO 86
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 86
cattttgcag agctggcagc                                            20

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 87
cttctgtcag gagatgatcc                                            20

<210> SEQ ID NO 88
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 88
ggagtgcatt atatccagac g                                          21

<210> SEQ ID NO 89
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 89
cctggctctg cttgaccaac                                            20
```

<210> SEQ ID NO 90
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 90
tgctgtcctg tgagagcatc					20

<210> SEQ ID NO 91
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 91
gtaaccctcc cagctttgg					19

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 92
cagttcccac ataaggcctg					20

<210> SEQ ID NO 93
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 93
cagttctgga tgccctgag					19

<210> SEQ ID NO 94
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 94
gaagagaggt cccatggaaa gg				22

<210> SEQ ID NO 95
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 95
gcttgcataa gcatatcaat tg				22

<210> SEQ ID NO 96
<211> LENGTH: 21
<212> TYPE: DNA
<213> ORGANISM: Artificial Sequence
<220> FEATURE:

<223> OTHER INFORMATION: Oligonucleotide primer

<400> SEQUENCE: 96
ctcctaaacc atcctttgct c          21

<210> SEQ ID NO 97
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 97
aggcaggcac aagagctg          18

<210> SEQ ID NO 98
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 98
cttaccctgg ggcctgac          18

<210> SEQ ID NO 99
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 99
ctcagagcca ccctactata g          21

<210> SEQ ID NO 100
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 100
gaagcttctc cagccctagc          20

<210> SEQ ID NO 101
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 101
tgcactctca tgaaacaggc          20

<210> SEQ ID NO 102
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 102
gtttggggtg tttgcttgtc          20

```
<210> SEQ ID NO 103
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 103
acctctttcc ccaacccaga g                                    21

<210> SEQ ID NO 104
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 104
gaagcagtaa tcagaagggc                                      20

<210> SEQ ID NO 105
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 105
gcctcacatt cttccatgct g                                    21

<210> SEQ ID NO 106
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 106
tcacatccca caggcaagag                                      20

<210> SEQ ID NO 107
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 107
ttccaagtgt caatggagaa c                                    21

<210> SEQ ID NO 108
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 108
attaccttag gcccaaccac                                      20

<210> SEQ ID NO 109
<211> LENGTH: 19
<212> TYPE: DNA
<213> ORGANISM: Artificial Sequence
<220> FEATURE:
<223> OTHER INFORMATION: Oligonucleotide primer
```

```
<400> SEQUENCE: 109
acactgggtg ttctggacc                                            19

<210> SEQ ID NO 110
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 110
gtgtagggtg gtgttttcc                                            19

<210> SEQ ID NO 111
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 111
aagcccagtg aaccagctgg                                           20

<210> SEQ ID NO 112
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 112
tcagctgagt gcccttcag                                            19

<210> SEQ ID NO 113
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 113
aggtgagcaa gtcagtttcg g                                         21

<210> SEQ ID NO 114
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 114
ggtcttcgtg tgtggtcatt                                           20

<210> SEQ ID NO 115
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 115
ggtccagttc ttccagag                                             18

<210> SEQ ID NO 116
<211> LENGTH: 22
```

-continued

```
<212> TYPE: DNA
<213> ORGANISM: Artificial Sequence
<220> FEATURE:
<223> OTHER INFORMATION: Oligonucleotide primer

<400> SEQUENCE: 116
atcctctgac tcagcaatca ca                                             22

<210> SEQ ID NO 117
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 117
ttgcaattac aaatgcaatg g                                              21

<210> SEQ ID NO 118
<211> LENGTH: 2261
<212> TYPE: PRT
<213> ORGANISM: Mouse
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: misc_feature
<222> LOCATION: (13)..(13)
<223> OTHER INFORMATION: Xaa is any amino acid
<220> FEATURE:
<221> NAME/KEY: misc_feature
<222> LOCATION: (136)..(136)
<223> OTHER INFORMATION: Xaa is any amino acid
<220> FEATURE:
<221> NAME/KEY: misc_feature
<222> LOCATION: (175)..(175)
<223> OTHER INFORMATION: Xaa is any amino acid
<220> FEATURE:
<221> NAME/KEY: misc_feature
<222> LOCATION: (221)..(221)
<223> OTHER INFORMATION: Xaa is any amino acid
<220> FEATURE:
<221> NAME/KEY: misc_feature
<222> LOCATION: (331)..(331)
<223> OTHER INFORMATION: Xaa is any amino acid
<220> FEATURE:
<221> NAME/KEY: misc_feature
<222> LOCATION: (401)..(401)
<223> OTHER INFORMATION: Xaa is any amino acid
<220> FEATURE:
<221> NAME/KEY: misc_feature
<222> LOCATION: (522)..(522)
<223> OTHER INFORMATION: Xaa is any amino acid
<220> FEATURE:
<221> NAME/KEY: misc_feature
<222> LOCATION: (614)..(614)
<223> OTHER INFORMATION: Xaa is any amino acid

<400> SEQUENCE: 118

Met Ala Cys Lys Pro Gln Leu Arg Leu Leu Leu Trp Lys Asn Leu Thr
1               5                   10                  15

Phe Arg Arg Arg Gln Thr Cys Gln Leu Leu Leu Glu Val Ala Trp Pro
                20                  25                  30

Leu Phe Ile Phe Leu Ile Leu Ile Ser Val Arg Leu Ser Tyr Pro Pro
            35                  40                  45

Tyr Glu Gln His Glu Cys His Phe Pro Asn Lys Ala Met Pro Ser Ala
        50                  55                  60

Gly Thr Leu Pro Trp Val Gln Gly Ile Ile Cys Asn Ala Asn Asn Pro
65                  70                  75                  80
```

-continued

```
Cys Phe Arg Tyr Pro Thr Pro Gly Glu Ala Pro Gly Val Val Gly Asn
                 85                  90                  95

Phe Asn Lys Ser Ile Val Ser Arg Leu Phe Ser Asp Ala Gln Arg Leu
            100                 105                 110

Leu Leu Tyr Ser Gln Arg Asp Thr Ser Ile Lys Asp Met His Lys Val
            115                 120                 125

Leu Arg Met Leu Arg Gln Ile Lys His Pro Asn Ser Asn Leu Lys Leu
        130                 135                 140

Gln Asp Phe Leu Val Asp Asn Glu Thr Phe Ser Gly Phe Leu Gln His
145                 150                 155                 160

Asn Leu Ser Leu Pro Arg Ser Thr Val Asp Ser Leu Leu Gln Lys Asn
                165                 170                 175

Val Gly Leu Gln Lys Val Phe Leu Gln Gly Tyr Gln Leu His Leu Ala
                180                 185                 190

Ser Leu Cys Asn Gly Ser Lys Leu Glu Glu Ile Ile Gln Leu Gly Asp
            195                 200                 205

Ala Glu Val Ser Ala Leu Cys Gly Leu Pro Arg Lys Lys Leu Asp Ala
        210                 215                 220

Ala Glu Arg Val Leu Arg Tyr Asn Met Asp Ile Leu Lys Pro Val Val
225                 230                 235                 240

Thr Lys Leu Asn Ser Thr Ser His Leu Pro Thr Gln His Leu Ala Glu
                245                 250                 255

Ala Thr Thr Val Leu Leu Asp Ser Leu Gly Gly Leu Ala Gln Glu Leu
            260                 265                 270

Phe Ser Thr Lys Ser Trp Ser Asp Met Arg Gln Glu Val Met Phe Leu
        275                 280                 285

Thr Asn Val Asn Ser Ser Ser Ser Thr Gln Ile Tyr Gln Ala Val
290                 295                 300

Ser Arg Ile Val Cys Gly His Pro Glu Gly Gly Leu Lys Ile Lys
305                 310                 315                 320

Ser Leu Asn Trp Tyr Glu Asp Asn Asn Tyr Lys Ala Leu Phe Gly Gly
                325                 330                 335

Asn Asn Thr Glu Glu Asp Val Asp Thr Phe Tyr Asp Asn Ser Thr Thr
            340                 345                 350

Pro Tyr Cys Asn Asp Leu Met Lys Asn Leu Glu Ser Ser Pro Leu Ser
        355                 360                 365

Arg Ile Ile Trp Lys Ala Leu Lys Pro Leu Leu Val Gly Lys Ile Leu
        370                 375                 380

Tyr Thr Pro Asp Thr Pro Ala Thr Arg Gln Val Met Ala Glu Val Asn
385                 390                 395                 400

Lys Thr Phe Gln Glu Leu Ala Val Phe His Asp Leu Glu Gly Met Trp
            405                 410                 415

Glu Glu Leu Ser Pro Gln Ile Trp Thr Phe Met Glu Asn Ser Gln Glu
                420                 425                 430

Met Asp Leu Val Arg Thr Leu Leu Asp Ser Arg Gly Asn Asp Gln Phe
            435                 440                 445

Trp Glu Gln Lys Leu Asp Gly Leu Asp Trp Thr Ala Gln Asp Ile Met
450                 455                 460

Ala Phe Leu Ala Lys Asn Pro Glu Asp Val Gln Ser Pro Asn Gly Ser
465                 470                 475                 480

Val Tyr Thr Trp Arg Glu Ala Phe Asn Glu Thr Asn Gln Ala Ile Gln
                485                 490                 495
```

-continued

```
Thr Ile Ser Arg Phe Met Glu Cys Val Asn Leu Asn Lys Leu Glu Pro
        500                 505                 510

Ile Pro Thr Glu Val Arg Leu Ile Asn Lys Ser Met Glu Leu Leu Asp
        515                 520                 525

Glu Arg Lys Phe Trp Ala Gly Ile Val Phe Thr Gly Ile Thr Pro Asp
        530                 535                 540

Ser Val Glu Leu Pro His His Val Lys Tyr Lys Ile Arg Met Asp Ile
545                 550                 555                 560

Asp Asn Val Glu Arg Thr Asn Lys Ile Lys Asp Gly Tyr Trp Asp Pro
                565                 570                 575

Gly Pro Arg Ala Asp Pro Phe Glu Asp Met Arg Tyr Val Trp Gly Gly
        580                 585                 590

Phe Ala Tyr Leu Gln Asp Val Val Glu Gln Ala Ile Ile Arg Val Leu
        595                 600                 605

Thr Gly Ser Glu Lys Lys Thr Gly Val Tyr Val Gln Gln Met Pro Tyr
        610                 615                 620

Pro Cys Tyr Val Asp Asp Ile Phe Leu Arg Val Met Ser Arg Ser Met
625                 630                 635                 640

Pro Leu Phe Met Thr Leu Ala Trp Ile Tyr Ser Val Ala Val Ile Ile
                645                 650                 655

Lys Ser Ile Val Tyr Glu Lys Glu Ala Arg Leu Lys Glu Thr Met Arg
                660                 665                 670

Ile Met Gly Leu Asp Asn Gly Ile Leu Trp Phe Ser Trp Phe Val Ser
                675                 680                 685

Ser Leu Ile Pro Leu Leu Val Ser Ala Gly Leu Leu Val Val Ile Leu
        690                 695                 700

Lys Leu Gly Asn Leu Leu Pro Tyr Ser Asp Pro Ser Val Val Phe Val
705                 710                 715                 720

Phe Leu Ser Val Phe Ala Met Val Thr Ile Leu Gln Cys Phe Leu Ile
                725                 730                 735

Ser Thr Leu Phe Ser Arg Ala Asn Leu Ala Ala Ala Cys Gly Gly Ile
                740                 745                 750

Ile Tyr Phe Thr Leu Tyr Leu Pro Tyr Val Leu Cys Val Ala Trp Gln
        755                 760                 765

Asp Tyr Val Gly Phe Ser Ile Lys Ile Phe Ala Ser Leu Leu Ser Pro
        770                 775                 780

Val Ala Phe Gly Phe Gly Cys Glu Tyr Phe Ala Leu Phe Glu Glu Gln
785                 790                 795                 800

Gly Ile Gly Val Gln Trp Asp Asn Leu Phe Glu Ser Pro Val Glu Glu
                805                 810                 815

Asp Gly Phe Asn Leu Thr Thr Ala Val Ser Met Met Leu Phe Asp Thr
                820                 825                 830

Phe Leu Tyr Gly Val Met Thr Trp Tyr Ile Glu Ala Val Phe Pro Gly
        835                 840                 845

Gln Tyr Gly Ile Pro Arg Pro Trp Tyr Phe Pro Cys Thr Lys Ser Tyr
        850                 855                 860

Trp Phe Gly Glu Glu Ile Asp Glu Lys Ser His Pro Gly Ser Ser Gln
865                 870                 875                 880

Lys Gly Val Ser Glu Ile Cys Met Glu Glu Pro Thr His Leu Arg
                885                 890                 895

Leu Gly Val Ser Ile Gln Asn Leu Val Lys Val Tyr Arg Asp Gly Met
                900                 905                 910

Lys Val Ala Val Asp Gly Leu Ala Leu Asn Phe Tyr Glu Gly Gln Ile
```

```
            915                 920                 925
Thr Ser Phe Leu Gly His Asn Gly Ala Gly Lys Thr Thr Met Ser
            930                 935                 940

Ile Leu Thr Gly Leu Phe Pro Pro Thr Ser Gly Thr Ala Tyr Ile Leu
945                 950                 955                 960

Gly Lys Asp Ile Arg Ser Glu Met Ser Ser Ile Arg Gln Asn Leu Gly
                965                 970                 975

Val Cys Pro Gln His Asn Val Leu Phe Asp Met Leu Thr Val Glu Glu
                980                 985                 990

His Ile Trp Phe Tyr Ala Arg Leu Lys Gly Leu Ser Glu Lys His Val
                995                1000                1005

Lys Ala Glu Met Glu Gln Met Ala Leu Asp Val Gly Leu Pro Pro
    1010                1015                1020

Ser Lys Leu Lys Ser Lys Thr Ser Gln Leu Ser Gly Gly Met Gln
    1025                1030                1035

Arg Lys Leu Ser Val Ala Leu Ala Phe Val Gly Gly Ser Lys Val
    1040                1045                1050

Val Ile Leu Asp Glu Pro Thr Ala Gly Val Asp Pro Tyr Ser Arg
    1055                1060                1065

Arg Gly Ile Trp Glu Leu Leu Leu Lys Tyr Arg Gln Gly Arg Thr
    1070                1075                1080

Ile Ile Leu Ser Thr His His Met Asp Glu Ala Asp Ile Leu Gly
    1085                1090                1095

Asp Arg Ile Ala Ile Ile Ser His Gly Lys Leu Cys Cys Val Gly
    1100                1105                1110

Ser Ser Leu Phe Leu Lys Asn Gln Leu Gly Thr Gly Tyr Tyr Leu
    1115                1120                1125

Thr Leu Val Lys Lys Asp Val Glu Ser Ser Leu Ser Ser Cys Arg
    1130                1135                1140

Asn Ser Ser Ser Thr Val Ser Cys Leu Lys Lys Glu Asp Ser Val
    1145                1150                1155

Ser Gln Ser Ser Ser Asp Ala Gly Leu Gly Ser Asp His Glu Ser
    1160                1165                1170

Asp Thr Leu Thr Ile Asp Val Ser Ala Ile Ser Asn Leu Ile Arg
    1175                1180                1185

Lys His Val Ser Glu Ala Arg Leu Val Glu Asp Ile Gly His Glu
    1190                1195                1200

Leu Thr Tyr Val Leu Pro Tyr Glu Ala Ala Lys Glu Gly Ala Phe
    1205                1210                1215

Val Glu Leu Phe His Glu Ile Asp Asp Arg Leu Ser Asp Leu Gly
    1220                1225                1230

Ile Ser Ser Tyr Gly Ile Ser Glu Thr Thr Leu Glu Glu Ile Phe
    1235                1240                1245

Leu Lys Val Ala Glu Glu Ser Gly Val Asp Ala Glu Thr Ser Asp
    1250                1255                1260

Gly Thr Leu Pro Ala Arg Arg Asn Arg Arg Ala Phe Gly Asp Lys
    1265                1270                1275

Gln Ser Cys Leu His Pro Phe Thr Glu Asp Asp Ala Val Asp Pro
    1280                1285                1290

Asn Asp Ser Asp Ile Asp Pro Glu Ser Arg Glu Thr Asp Leu Leu
    1295                1300                1305

Ser Gly Met Asp Gly Lys Gly Ser Tyr Gln Leu Lys Gly Trp Lys
    1310                1315                1320
```

-continued

```
Leu Thr Gln Gln Gln Phe Val Ala Leu Leu Trp Lys Arg Leu Leu
    1325                1330                1335
Ile Ala Arg Arg Ser Arg Lys Gly Phe Phe Ala Gln Ile Val Leu
    1340                1345                1350
Pro Ala Val Phe Val Cys Ile Ala Leu Val Phe Ser Leu Ile Val
    1355                1360                1365
Pro Pro Phe Gly Lys Tyr Pro Ser Leu Glu Leu Gln Pro Trp Met
    1370                1375                1380
Tyr Asn Glu Gln Tyr Thr Phe Val Ser Asn Asp Ala Pro Glu Asp
    1385                1390                1395
Met Gly Thr Gln Glu Leu Leu Asn Ala Leu Thr Lys Asp Pro Gly
    1400                1405                1410
Phe Gly Thr Arg Cys Met Glu Gly Asn Pro Ile Pro Asp Thr Pro
    1415                1420                1425
Cys Leu Ala Gly Glu Glu Asp Trp Thr Ile Ser Pro Val Pro Gln
    1430                1435                1440
Ser Ile Val Asp Leu Phe Gln Asn Gly Asn Trp Thr Met Lys Asn
    1445                1450                1455
Pro Ser Pro Ala Cys Gln Cys Ser Ser Asp Lys Ile Lys Lys Met
    1460                1465                1470
Leu Pro Val Cys Pro Pro Gly Ala Gly Gly Leu Pro Pro Pro Gln
    1475                1480                1485
Arg Lys Gln Lys Thr Ala Asp Ile Leu Gln Asn Leu Thr Gly Arg
    1490                1495                1500
Asn Ile Ser Asp Tyr Leu Val Lys Thr Tyr Val Gln Ile Ile Ala
    1505                1510                1515
Lys Ser Leu Lys Asn Lys Ile Trp Val Asn Glu Phe Arg Tyr Gly
    1520                1525                1530
Gly Phe Ser Leu Gly Val Ser Asn Ser Gln Ala Leu Pro Pro Ser
    1535                1540                1545
His Glu Val Asn Asp Ala Ile Lys Gln Met Lys Lys Leu Leu Lys
    1550                1555                1560
Leu Thr Lys Asp Thr Ser Ala Asp Arg Phe Leu Ser Ser Leu Gly
    1565                1570                1575
Arg Phe Met Ala Gly Leu Asp Thr Lys Asn Asn Val Lys Val Trp
    1580                1585                1590
Phe Asn Asn Lys Gly Trp His Ala Ile Ser Ser Phe Leu Asn Val
    1595                1600                1605
Ile Asn Asn Ala Ile Leu Arg Ala Asn Leu Gln Lys Gly Glu Asn
    1610                1615                1620
Pro Ser Gln Tyr Gly Ile Thr Ala Phe Asn His Pro Leu Asn Leu
    1625                1630                1635
Thr Lys Gln Gln Leu Ser Glu Val Ala Leu Met Thr Thr Ser Val
    1640                1645                1650
Asp Val Leu Val Ser Ile Cys Val Ile Phe Ala Met Ser Phe Val
    1655                1660                1665
Pro Ala Ser Phe Val Val Phe Leu Ile Gln Glu Arg Val Ser Lys
    1670                1675                1680
Ala Lys His Leu Gln Phe Ile Ser Gly Val Lys Pro Val Ile Tyr
    1685                1690                1695
Trp Leu Ser Asn Phe Val Trp Asp Met Cys Asn Tyr Val Val Pro
    1700                1705                1710
```

```
Ala Thr Leu Val Ile Ile Ile Phe Ile Gly Phe Gln Gln Lys Ser
    1715                1720                1725

Tyr Val Ser Ser Thr Asn Leu Pro Val Leu Ala Leu Leu Leu Leu
    1730                1735                1740

Leu Tyr Gly Trp Ser Ile Thr Pro Leu Met Tyr Pro Ala Ser Phe
    1745                1750                1755

Val Phe Lys Ile Pro Ser Thr Ala Tyr Val Val Leu Thr Ser Val
    1760                1765                1770

Asn Leu Phe Ile Gly Ile Asn Gly Ser Val Ala Thr Phe Val Leu
    1775                1780                1785

Glu Leu Phe Thr Asn Asn Lys Leu Asn Asp Ile Asn Asp Ile Leu
    1790                1795                1800

Lys Ser Val Phe Leu Ile Phe Pro His Phe Cys Leu Gly Arg Gly
    1805                1810                1815

Leu Ile Asp Met Val Lys Asn Gln Ala Met Ala Asp Ala Leu Glu
    1820                1825                1830

Arg Phe Gly Glu Asn Arg Phe Val Ser Pro Leu Ser Trp Asp Leu
    1835                1840                1845

Val Gly Arg Asn Leu Phe Ala Met Ala Val Glu Gly Val Val Phe
    1850                1855                1860

Phe Leu Ile Thr Val Leu Ile Gln Tyr Arg Phe Phe Ile Arg Pro
    1865                1870                1875

Arg Pro Val Lys Ala Lys Leu Pro Pro Leu Asn Asp Glu Asp Glu
    1880                1885                1890

Asp Val Arg Arg Glu Arg Gln Arg Ile Leu Asp Gly Gly Gly Gln
    1895                1900                1905

Asn Asp Ile Leu Glu Ile Lys Glu Leu Thr Lys Ile Tyr Arg Arg
    1910                1915                1920

Lys Arg Lys Pro Ala Val Asp Arg Ile Cys Ile Gly Ile Pro Pro
    1925                1930                1935

Gly Glu Cys Phe Gly Leu Leu Gly Val Asn Gly Ala Gly Lys Ser
    1940                1945                1950

Thr Thr Phe Lys Met Leu Thr Gly Asp Thr Pro Val Thr Arg Gly
    1955                1960                1965

Asp Ala Phe Leu Asn Lys Asn Ser Ile Leu Ser Asn Ile His Glu
    1970                1975                1980

Val His Gln Asn Met Gly Tyr Cys Pro Gln Phe Asp Ala Ile Thr
    1985                1990                1995

Glu Leu Leu Thr Gly Arg Glu His Val Glu Phe Phe Ala Leu Leu
    2000                2005                2010

Arg Gly Val Pro Glu Lys Glu Val Gly Lys Phe Gly Glu Trp Ala
    2015                2020                2025

Ile Arg Lys Leu Gly Leu Val Lys Tyr Gly Glu Lys Tyr Ala Ser
    2030                2035                2040

Asn Tyr Ser Gly Gly Asn Lys Arg Lys Leu Ser Thr Ala Met Ala
    2045                2050                2055

Leu Ile Gly Gly Pro Pro Val Val Phe Leu Asp Glu Pro Thr Thr
    2060                2065                2070

Gly Met Asp Pro Lys Ala Arg Arg Phe Leu Trp Asn Cys Ala Leu
    2075                2080                2085

Ser Ile Val Lys Glu Gly Arg Ser Val Val Leu Thr Ser His Ser
    2090                2095                2100

Met Glu Glu Cys Glu Ala Leu Cys Thr Arg Met Ala Ile Met Val
```

-continued

```
            2105                  2110                  2115
Asn Gly Arg Phe Arg Cys Leu Gly Ser Val Gln His Leu Lys Asn
            2120                  2125                  2130

Arg Phe Gly Asp Gly Tyr Thr Ile Val Val Arg Ile Ala Gly Ser
            2135                  2140                  2145

Asn Pro Asp Leu Lys Pro Val Gln Glu Phe Phe Gly Leu Ala Phe
            2150                  2155                  2160

Pro Gly Ser Val Leu Lys Glu Lys His Arg Asn Met Leu Gln Tyr
            2165                  2170                  2175

Gln Leu Pro Ser Ser Leu Ser Ser Leu Ala Arg Ile Phe Ser Ile
            2180                  2185                  2190

Leu Ser Gln Ser Lys Lys Arg Leu His Ile Glu Asp Tyr Ser Val
            2195                  2200                  2205

Ser Gln Thr Thr Leu Asp Gln Val Phe Val Asn Phe Ala Lys Asp
            2210                  2215                  2220

Gln Ser Asp Asp Asp His Leu Lys Asp Leu Ser Leu His Lys Asn
            2225                  2230                  2235

Gln Thr Val Val Asp Val Ala Val Leu Thr Ser Phe Leu Gln Asp
            2240                  2245                  2250

Glu Lys Val Lys Glu Ser Tyr Val
            2255                  2260

<210> SEQ ID NO 119
<211> LENGTH: 1472
<212> TYPE: PRT
<213> ORGANISM: Mouse

<400> SEQUENCE: 119

Gln Ala Cys Ala Met Glu Ser Arg His Phe Glu Glu Thr Arg Gly Met
1                5                  10                  15

Glu Glu Glu Pro Thr His Leu Pro Leu Val Val Cys Val Asp Lys Leu
                20                  25                  30

Thr Lys Val Tyr Lys Asn Asp Lys Lys Leu Ala Leu Asn Lys Leu Ser
            35                  40                  45

Leu Asn Leu Tyr Glu Asn Gln Val Val Ser Phe Leu Gly His Asn Gly
        50                  55                  60

Ala Gly Lys Thr Thr Thr Met Ser Ile Leu Thr Gly Leu Phe Pro Pro
65                  70                  75                  80

Thr Ser Gly Ser Ala Thr Ile Tyr Gly His Asp Ile Arg Thr Glu Met
                85                  90                  95

Asp Glu Ile Arg Lys Asn Leu Gly Met Cys Pro Gln His Asn Val Leu
            100                 105                 110

Phe Asp Arg Leu Thr Val Glu Glu His Leu Trp Phe Tyr Ser Arg Leu
        115                 120                 125

Lys Ser Met Ala Gln Glu Glu Ile Arg Lys Glu Thr Asp Lys Met Ile
    130                 135                 140

Glu Asp Leu Glu Leu Ser Asn Lys Arg His Ser Leu Val Gln Thr Leu
145                 150                 155                 160

Ser Gly Gly Met Lys Arg Lys Leu Ser Val Ala Ile Ala Phe Val Gly
                165                 170                 175

Gly Ser Arg Ala Ile Ile Leu Asp Glu Pro Thr Ala Gly Val Asp Pro
            180                 185                 190

Tyr Ala Arg Arg Ala Ile Trp Asp Leu Ile Leu Lys Tyr Lys Pro Gly
        195                 200                 205
```

-continued

```
Arg Thr Ile Leu Leu Ser Thr His His Met Asp Glu Ala Asp Leu Leu
    210                 215                 220

Gly Asp Arg Ile Ala Ile Ile Ser His Gly Lys Leu Lys Cys Cys Gly
225                 230                 235                 240

Ser Pro Leu Phe Leu Lys Gly Ala Tyr Lys Asp Gly Tyr Arg Leu Thr
                245                 250                 255

Leu Val Lys Gln Pro Ala Glu Pro Gly Thr Ser Gln Glu Pro Gly Leu
            260                 265                 270

Ala Ser Ser Pro Ser Gly Cys Pro Arg Leu Ser Ser Cys Ser Glu Pro
        275                 280                 285

Gln Val Ser Gln Phe Ile Arg Lys His Val Ala Ser Ser Leu Leu Val
    290                 295                 300

Ser Asp Thr Ser Thr Glu Leu Ser Tyr Ile Leu Pro Ser Glu Ala Val
305                 310                 315                 320

Lys Lys Gly Ala Phe Glu Arg Leu Phe Gln Gln Leu Glu His Ser Leu
                325                 330                 335

Asp Ala Leu His Leu Ser Ser Phe Gly Leu Met Asp Thr Thr Leu Glu
            340                 345                 350

Glu Val Phe Leu Lys Val Ser Glu Glu Asp Gln Ser Leu Glu Asn Ser
        355                 360                 365

Glu Ala Asp Val Lys Glu Ser Arg Lys Asp Val Leu Pro Gly Ala Glu
    370                 375                 380

Gly Leu Thr Ala Val Gly Gly Gln Ala Gly Asn Leu Ala Arg Cys Ser
385                 390                 395                 400

Glu Leu Ala Gln Ser Gln Ala Ser Leu Gln Ser Ala Ser Ser Val Gly
                405                 410                 415

Ser Ala Arg Gly Glu Glu Gly Thr Gly Tyr Ser Asp Gly Tyr Gly Asp
            420                 425                 430

Tyr Arg Pro Leu Phe Asp Asn Leu Gln Asp Pro Asp Asn Val Ser Leu
        435                 440                 445

Gln Glu Ala Glu Met Glu Ala Leu Ala Gln Val Gly Gln Gly Ser Arg
    450                 455                 460

Lys Leu Glu Gly Trp Trp Leu Lys Met Arg Gln Phe His Gly Leu Leu
465                 470                 475                 480

Val Lys Arg Phe His Cys Ala Arg Arg Asn Ser Lys Ala Leu Cys Ser
                485                 490                 495

Gln Ile Leu Leu Pro Ala Phe Phe Val Cys Val Ala Met Thr Val Ala
            500                 505                 510

Leu Ser Val Pro Glu Ile Gly Asp Leu Pro Pro Leu Val Leu Ser Pro
        515                 520                 525

Ser Gln Tyr His Asn Tyr Thr Gln Pro Arg Gly Asn Phe Ile Pro Tyr
    530                 535                 540

Ala Asn Glu Glu Arg Gln Glu Tyr Arg Leu Arg Leu Ser Pro Asp Ala
545                 550                 555                 560

Ser Pro Gln Gln Leu Val Ser Thr Phe Arg Leu Pro Ser Gly Val Gly
                565                 570                 575

Ala Thr Cys Val Leu Lys Ser Pro Ala Asn Gly Ser Leu Gly Pro Met
            580                 585                 590

Leu Asn Leu Ser Ser Gly Glu Ser Arg Leu Leu Ala Ala Arg Phe Phe
        595                 600                 605

Asp Ser Met Cys Leu Glu Ser Phe Thr Gln Gly Leu Pro Leu Ser Asn
    610                 615                 620

Phe Val Pro Pro Pro Ser Pro Ala Pro Ser Asp Ser Pro Val Lys
```

-continued

```
625                 630                 635                 640
Pro Asp Glu Asp Ser Leu Gln Ala Trp Asn Met Ser Leu Pro Pro Thr
                645                 650                 655
Ala Gly Pro Glu Thr Trp Thr Ser Ala Pro Ser Leu Pro Arg Leu Val
                660                 665                 670
His Glu Pro Val Arg Cys Thr Cys Ser Ala Gln Gly Thr Gly Phe Ser
                675                 680                 685
Cys Pro Ser Ser Val Gly Gly His Pro Pro Gln Met Arg Val Val Thr
            690                 695                 700
Gly Asp Ile Leu Thr Asp Ile Thr Gly His Asn Val Ser Glu Tyr Leu
705                 710                 715                 720
Leu Phe Thr Ser Asp Arg Phe Arg Leu His Arg Tyr Gly Ala Ile Thr
                725                 730                 735
Phe Gly Asn Val Gln Lys Ser Ile Pro Ala Ser Phe Gly Ala Arg Val
                740                 745                 750
Pro Pro Met Val Arg Lys Ile Ala Val Arg Arg Val Ala Gln Val Leu
                755                 760                 765
Tyr Asn Asn Lys Gly Tyr His Ser Met Pro Thr Tyr Leu Asn Ser Leu
                770                 775                 780
Asn Asn Ala Ile Leu Arg Ala Asn Leu Pro Lys Ser Lys Gly Asn Pro
785                 790                 795                 800
Ala Ala Tyr Lys Ile Thr Val Thr Asn His Pro Met Asn Lys Thr Ser
                805                 810                 815
Ala Ser Leu Ser Leu Asp Tyr Leu Leu Gln Gly Thr Asp Val Val Ile
                820                 825                 830
Ala Ile Phe Ile Ile Val Ala Met Ser Phe Val Pro Ala Ser Phe Val
                835                 840                 845
Val Phe Leu Val Ala Glu Lys Ser Thr Lys Ala Lys His Leu Gln Phe
                850                 855                 860
Val Ser Gly Cys Asn Pro Val Ile Tyr Trp Leu Ala Asn Tyr Val Trp
865                 870                 875                 880
Asp Met Leu Asn Tyr Leu Val Pro Ala Thr Cys Cys Val Ile Ile Leu
                885                 890                 895
Phe Val Phe Asp Leu Pro Ala Tyr Thr Ser Pro Thr Asn Phe Pro Ala
                900                 905                 910
Val Leu Ser Leu Phe Leu Leu Tyr Gly Trp Ser Ile Thr Pro Ile Met
                915                 920                 925
Tyr Pro Ala Ser Phe Trp Phe Glu Val Pro Ser Ser Ala Tyr Val Phe
                930                 935                 940
Leu Ile Val Ile Asn Leu Phe Ile Gly Ile Thr Ala Thr Val Ala Thr
945                 950                 955                 960
Phe Leu Leu Gln Leu Phe Glu His Asp Lys Asp Leu Lys Val Val Asn
                965                 970                 975
Ser Tyr Leu Lys Ser Cys Phe Leu Ile Phe Pro Asn Tyr Asn Leu Gly
                980                 985                 990
His Gly Leu Met Glu Met Ala Tyr Asn Glu Tyr Ile Asn Glu Tyr Tyr
                995                 1000                1005
Ala Lys Ile Gly Gln Phe Asp Lys Met Lys Ser Pro Phe Glu Trp
                1010                1015                1020
Asp Ile Val Thr Arg Gly Leu Val Ala Met Thr Val Glu Gly Phe
                1025                1030                1035
Val Gly Phe Phe Leu Thr Ile Met Cys Gln Tyr Asn Phe Leu Arg
                1040                1045                1050
```

```
Gln Pro Gln Arg Leu Pro Val Ser Thr Lys Pro Val Glu Asp Asp
        1055                1060                1065

Val Asp Val Ala Ser Glu Arg Gln Arg Val Leu Arg Gly Asp Ala
    1070                1075                1080

Asp Asn Asp Met Val Lys Ile Glu Asn Leu Thr Lys Val Tyr Lys
        1085                1090                1095

Ser Arg Lys Ile Gly Arg Ile Leu Ala Val Asp Arg Leu Cys Leu
    1100                1105                1110

Gly Val Cys Val Pro Gly Glu Cys Phe Gly Leu Leu Gly Val Asn
    1115                1120                1125

Gly Ala Gly Lys Thr Ser Thr Phe Lys Met Leu Thr Gly Asp Glu
    1130                1135                1140

Ser Thr Thr Gly Gly Glu Ala Phe Val Asn Gly His Ser Val Leu
    1145                1150                1155

Lys Asp Leu Leu Gln Val Gln Gln Ser Leu Gly Tyr Cys Pro Gln
    1160                1165                1170

Phe Asp Val Pro Val Asp Glu Leu Thr Ala Arg Glu His Leu Gln
    1175                1180                1185

Leu Tyr Thr Arg Leu Arg Cys Ile Pro Trp Lys Asp Glu Ala Gln
    1190                1195                1200

Val Val Lys Trp Ala Leu Glu Lys Leu Glu Leu Thr Lys Tyr Ala
    1205                1210                1215

Asp Lys Pro Ala Gly Thr Tyr Ser Gly Gly Asn Lys Arg Lys Leu
    1220                1225                1230

Ser Thr Ala Ile Ala Leu Ile Gly Tyr Pro Ala Phe Ile Phe Leu
    1235                1240                1245

Asp Glu Pro Thr Thr Gly Met Asp Pro Lys Ala Arg Arg Phe Leu
    1250                1255                1260

Trp Asn Leu Ile Leu Asp Leu Ile Lys Thr Gly Arg Ser Val Val
    1265                1270                1275

Leu Thr Ser His Ser Met Glu Glu Cys Glu Ala Leu Cys Thr Arg
    1280                1285                1290

Leu Ala Ile Met Val Asn Gly Arg Leu His Cys Leu Gly Ser Ile
    1295                1300                1305

Gln His Leu Lys Asn Arg Phe Gly Asp Gly Tyr Met Ile Thr Val
    1310                1315                1320

Arg Thr Lys Ser Ser Gln Asn Val Lys Asp Val Val Arg Phe Phe
    1325                1330                1335

Asn Arg Asn Phe Pro Glu Ala His Ala Gln Gly Lys Thr Pro Tyr
    1340                1345                1350

Lys Val Gln Tyr Gln Leu Lys Ser Glu His Ile Ser Leu Ala Gln
    1355                1360                1365

Val Phe Ser Lys Met Glu Gln Val Val Gly Val Leu Gly Ile Glu
    1370                1375                1380

Asp Tyr Ser Val Ser Gln Thr Thr Leu Asp Asn Val Phe Val Asn
    1385                1390                1395

Phe Ala Lys Lys Gln Ser Asp Asn Val Glu Gln Gln Glu Ala Glu
    1400                1405                1410

Pro Ser Ser Leu Pro Ser Pro Leu Gly Leu Leu Ser Leu Leu Arg
    1415                1420                1425

Pro Arg Pro Ala Pro Thr Glu Leu Arg Ala Leu Val Ala Asp Glu
    1430                1435                1440
```

-continued

```
Pro Glu  Asp Leu Asp Thr Glu  Asp Glu Gly Leu Ile  Ser Phe Glu
    1445             1450                 1455

Glu Glu  Arg Ala Gln Leu Ser  Phe Asn Thr Asp Thr  Leu Cys
    1460             1465                 1470

<210> SEQ ID NO 120
<211> LENGTH: 1704
<212> TYPE: PRT
<213> ORGANISM: Homo sapiens

<400> SEQUENCE: 120

Met Ala Val Leu Arg Gln Leu Ala Leu Leu Trp Lys Asn Tyr Thr
 1               5                  10                 15

Leu Gln Lys Arg Lys Val Leu Val Thr Val Leu Glu Leu Phe Leu Pro
            20                  25                  30

Leu Leu Phe Ser Gly Ile Leu Ile Trp Leu Arg Leu Lys Ile Gln Ser
             35                  40                  45

Glu Asn Val Pro Asn Ala Thr Ile Tyr Pro Gly Gln Ser Ile Gln Glu
     50                  55                  60

Leu Pro Leu Phe Phe Thr Phe Pro Pro Gly Asp Thr Trp Glu Leu
65              70                  75                  80

Ala Tyr Ile Pro Ser His Ser Asp Ala Ala Lys Thr Val Thr Glu Thr
                85                  90                  95

Val Arg Arg Ala Leu Val Ile Asn Met Arg Val Arg Gly Phe Pro Ser
            100                 105                 110

Glu Lys Asp Phe Glu Asp Tyr Ile Arg Tyr Asp Asn Cys Ser Ser Ser
            115                 120                 125

Val Leu Ala Ala Val Val Phe Glu His Pro Phe Asn His Ser Lys Glu
            130                 135                 140

Pro Leu Pro Leu Ala Val Lys Tyr His Leu Arg Phe Ser Tyr Thr Arg
145                 150                 155                 160

Arg Asn Tyr Met Trp Thr Gln Thr Gly Ser Phe Phe Leu Lys Glu Thr
                165                 170                 175

Glu Gly Trp His Thr Thr Ser Leu Phe Pro Leu Phe Pro Asn Pro Gly
            180                 185                 190

Pro Arg Glu Pro Thr Ser Pro Asp Gly Gly Glu Pro Gly Tyr Ile Arg
            195                 200                 205

Glu Gly Phe Leu Ala Val Gln His Ala Val Asp Arg Ala Ile Met Glu
            210                 215                 220

Tyr His Ala Asp Ala Ala Thr Arg Gln Leu Phe Gln Arg Leu Thr Val
225                 230                 235                 240

Thr Ile Lys Arg Phe Pro Tyr Pro Pro Phe Ile Glu Asp Pro Phe Leu
                245                 250                 255

Val Ala Ile Gln Tyr Gln Leu Pro Leu Leu Leu Leu Ser Phe Thr
            260                 265                 270

Tyr Thr Ala Leu Thr Ile Ala Arg Ala Val Val Gln Glu Lys Glu Arg
            275                 280                 285

Arg Leu Lys Glu Tyr Met Arg Met Met Gly Leu Ser Ser Trp Leu His
            290                 295                 300

Trp Ser Ala Trp Phe Leu Leu Phe Phe Leu Phe Leu Leu Ile Ala Ala
305                 310                 315                 320

Ser Phe Met Thr Leu Leu Phe Cys Val Lys Val Lys Pro Asn Val Ala
                325                 330                 335

Val Leu Ser Arg Ser Asp Pro Ser Leu Val Leu Ala Phe Leu Leu Cys
            340                 345                 350
```

```
Phe Ala Ile Ser Thr Ile Ser Phe Ser Phe Met Val Ser Thr Phe Phe
            355                 360                 365
Ser Lys Ala Asn Met Ala Ala Ala Phe Gly Gly Phe Leu Tyr Phe Phe
    370                 375                 380
Thr Tyr Ile Pro Tyr Phe Phe Val Ala Pro Arg Tyr Asn Trp Met Thr
385                 390                 395                 400
Leu Ser Gln Lys Leu Cys Ser Cys Leu Leu Ser Asn Val Ala Met Ala
                405                 410                 415
Met Gly Ala Gln Leu Ile Gly Lys Phe Glu Ala Lys Gly Met Gly Ile
            420                 425                 430
Gln Trp Arg Asp Leu Leu Ser Pro Val Asn Val Asp Asp Phe Cys
            435                 440                 445
Phe Gly Gln Val Leu Gly Met Leu Leu Leu Asp Ser Val Leu Tyr Gly
        450                 455                 460
Leu Val Thr Trp Tyr Met Glu Ala Val Phe Pro Gly Gln Phe Gly Val
465                 470                 475                 480
Pro Gln Pro Trp Tyr Phe Phe Ile Met Pro Ser Tyr Trp Cys Gly Lys
            485                 490                 495
Pro Arg Ala Val Ala Gly Lys Glu Glu Asp Ser Asp Pro Glu Lys
            500                 505                 510
Ala Leu Arg Asn Glu Tyr Phe Glu Ala Glu Pro Glu Asp Leu Val Ala
        515                 520                 525
Gly Ile Lys Ile Lys His Leu Ser Lys Val Phe Arg Val Gly Asn Lys
        530                 535                 540
Asp Arg Ala Ala Val Arg Asp Leu Asn Leu Asn Leu Tyr Glu Gly Gln
545                 550                 555                 560
Ile Thr Val Leu Leu Gly His Asn Gly Ala Gly Lys Thr Thr Thr Leu
                565                 570                 575
Ser Met Leu Thr Gly Leu Phe Pro Pro Thr Ser Gly Arg Ala Tyr Ile
            580                 585                 590
Ser Gly Tyr Glu Ile Ser Gln Asp Met Val Gln Ile Arg Lys Ser Leu
        595                 600                 605
Gly Leu Cys Pro Gln His Asp Ile Leu Phe Asp Asn Leu Thr Val Ala
    610                 615                 620
Glu His Leu Tyr Phe Tyr Ala Gln Leu Lys Gly Leu Ser Arg Gln Lys
625                 630                 635                 640
Cys Pro Glu Glu Val Lys Gln Met Leu His Ile Ile Gly Leu Glu Asp
                645                 650                 655
Lys Trp Asn Ser Arg Ser Arg Phe Leu Ser Gly Gly Met Arg Arg Lys
            660                 665                 670
Leu Ser Ile Gly Ile Ala Leu Ile Ala Gly Ser Lys Val Leu Ile Leu
        675                 680                 685
Asp Glu Pro Thr Ser Gly Met Asp Ala Ile Ser Arg Arg Ala Ile Trp
    690                 695                 700
Asp Leu Leu Gln Arg Gln Lys Ser Asp Arg Thr Ile Val Leu Thr Thr
705                 710                 715                 720
His Phe Met Asp Glu Ala Asp Leu Leu Gly Asp Arg Ile Ala Ile Met
                725                 730                 735
Ala Lys Gly Glu Leu Gln Cys Cys Gly Ser Ser Leu Phe Leu Lys Gln
            740                 745                 750
Lys Tyr Gly Ala Gly Tyr His Met Thr Leu Val Lys Glu Pro His Cys
        755                 760                 765
```

-continued

```
Asn Pro Glu Asp Ile Ser Gln Leu Val His His Val Pro Asn Ala
    770             775             780
Thr Leu Glu Ser Ser Ala Gly Ala Glu Leu Ser Phe Ile Leu Pro Arg
785             790             795             800
Glu Ser Thr His Arg Phe Gly Leu Phe Ala Lys Leu Glu Lys Lys
                805             810             815
Gln Lys Glu Leu Gly Ile Ala Ser Phe Gly Ala Ser Ile Thr Thr Met
            820             825             830
Glu Glu Val Phe Leu Arg Val Gly Lys Leu Val Asp Ser Ser Met Asp
            835             840             845
Ile Gln Ala Ile Gln Leu Pro Ala Leu Gln Tyr Gln His Glu Arg Arg
    850             855             860
Ala Ser Asp Trp Ala Val Asp Ser Asn Leu Cys Gly Ala Met Asp Pro
865             870             875             880
Ser Asp Gly Ile Gly Ala Leu Ile Glu Glu Arg Thr Ala Val Lys
                885             890             895
Leu Asn Thr Gly Leu Ala Leu His Cys Gln Gln Phe Trp Ala Met Phe
            900             905             910
Leu Lys Lys Ala Ala Tyr Ser Trp Arg Glu Trp Lys Met Val Ala Ala
            915             920             925
Gln Val Leu Val Pro Leu Thr Cys Val Thr Leu Ala Leu Leu Ala Ile
    930             935             940
Asn Tyr Ser Ser Glu Leu Phe Asp Asp Pro Met Leu Arg Leu Thr Leu
945             950             955             960
Gly Glu Tyr Gly Arg Thr Val Val Pro Phe Ser Val Pro Gly Thr Ser
                965             970             975
Gln Leu Gly Gln Gln Leu Ser Glu His Leu Lys Asp Ala Leu Gln Ala
            980             985             990
Glu Gly Gln Glu Pro Arg Glu Val  Leu Gly Asp Leu Glu  Glu Phe Leu
            995             1000              1005
Ile Phe  Arg Ala Ser Val Glu  Gly Gly Gly Phe Asn  Glu Arg Cys
    1010              1015              1020
Leu Val  Ala Ala Ser Phe Arg  Asp Val Gly Glu Arg  Thr Val Val
    1025              1030              1035
Asn Ala  Leu Phe Asn Asn Gln  Ala Tyr His Ser Pro  Ala Thr Ala
    1040              1045              1050
Leu Ala  Val Val Asp Asn Leu  Leu Phe Lys Leu Leu  Cys Gly Pro
    1055              1060              1065
His Ala  Ser Ile Val Val Ser  Asn Phe Pro Gln Pro  Arg Ser Ala
    1070              1075              1080
Leu Gln  Ala Ala Lys Asp Gln  Phe Asn Glu Gly Arg  Lys Gly Phe
    1085              1090              1095
Asp Ile  Ala Leu Asn Leu Leu  Phe Ala Met Ala Phe  Leu Ala Ser
    1100              1105              1110
Thr Phe  Ser Ile Leu Ala Val  Ser Glu Arg Ala Val  Gln Ala Lys
    1115              1120              1125
His Val  Gln Phe Val Ser Gly  Val His Val Ala Ser  Phe Trp Leu
    1130              1135              1140
Ser Ala  Leu Leu Trp Asp Leu  Ile Ser Phe Leu Ile  Pro Ser Leu
    1145              1150              1155
Leu Leu  Leu Val Val Phe Lys  Ala Phe Asp Val Arg  Ala Phe Thr
    1160              1165              1170
Arg Asp  Gly His Met Ala Asp  Thr Leu Leu Leu Leu  Leu Leu Tyr
```

-continued

```
            1175                1180                    1185

Gly Trp Ala Ile Ile Pro Leu Met Tyr Leu Met Asn Phe Phe Phe
    1190                1195                    1200

Leu Gly Ala Ala Thr Ala Tyr Thr Arg Leu Thr Ile Phe Asn Ile
    1205                1210                    1215

Leu Ser Gly Ile Ala Thr Phe Leu Met Val Thr Ile Met Arg Ile
    1220                1225                    1230

Pro Ala Val Lys Leu Glu Glu Leu Ser Lys Thr Leu Asp His Val
    1235                1240                    1245

Phe Leu Val Leu Pro Asn His Cys Leu Gly Met Ala Val Ser Ser
    1250                1255                    1260

Phe Tyr Glu Asn Tyr Glu Thr Arg Arg Tyr Cys Thr Ser Ser Glu
    1265                1270                    1275

Val Ala Ala His Tyr Cys Lys Lys Tyr Asn Ile Gln Tyr Gln Glu
    1280                1285                    1290

Asn Phe Tyr Ala Trp Ser Ala Pro Gly Val Gly Arg Phe Val Ala
    1295                1300                    1305

Ser Met Ala Ala Ser Gly Cys Ala Tyr Leu Ile Leu Leu Phe Leu
    1310                1315                    1320

Ile Glu Thr Asn Leu Leu Gln Arg Leu Arg Gly Ile Leu Cys Ala
    1325                1330                    1335

Leu Arg Arg Arg Arg Thr Leu Thr Glu Leu Tyr Thr Pro Met Pro
    1340                1345                    1350

Val Leu Pro Glu Asp Gln Asp Val Ala Asp Glu Arg Thr Arg Ile
    1355                1360                    1365

Leu Ala Pro Ser Pro Asp Ser Leu Leu His Thr Pro Leu Ile Ile
    1370                1375                    1380

Lys Glu Leu Ser Lys Val Tyr Glu Gln Arg Val Pro Leu Leu Ala
    1385                1390                    1395

Val Asp Arg Leu Ser Leu Ala Val Gln Lys Gly Glu Cys Phe Gly
    1400                1405                    1410

Leu Leu Gly Phe Asn Gly Ala Gly Lys Thr Thr Thr Phe Lys Met
    1415                1420                    1425

Leu Thr Gly Glu Glu Ser Leu Thr Ser Gly Asp Ala Phe Val Gly
    1430                1435                    1440

Gly His Arg Ile Ser Ser Asp Val Gly Lys Val Arg Gln Arg Ile
    1445                1450                    1455

Gly Tyr Cys Pro Gln Phe Asp Ala Leu Leu Asp His Met Thr Gly
    1460                1465                    1470

Arg Glu Met Leu Val Met Tyr Ala Arg Leu Arg Gly Ile Pro Glu
    1475                1480                    1485

Arg His Ile Gly Ala Cys Val Glu Asn Thr Leu Arg Gly Leu Leu
    1490                1495                    1500

Leu Glu Pro His Ala Asn Lys Leu Val Arg Thr Tyr Ser Gly Gly
    1505                1510                    1515

Asn Lys Arg Lys Leu Ser Thr Gly Ile Ala Leu Ile Gly Glu Pro
    1520                1525                    1530

Ala Val Ile Phe Leu Asp Glu Pro Ser Thr Gly Met Asp Pro Val
    1535                1540                    1545

Ala Arg Arg Leu Leu Trp Asp Thr Val Ala Arg Ala Arg Glu Ser
    1550                1555                    1560

Gly Lys Ala Ile Ile Ile Thr Ser His Ser Met Glu Glu Cys Glu
    1565                1570                    1575
```

-continued

```
Ala Leu Cys Thr Arg Leu Ala Ile Met Val Gln Gly Gln Phe Lys
    1580                1585                1590

Cys Leu Gly Ser Pro Gln His Leu Lys Ser Lys Phe Gly Ser Gly
    1595                1600                1605

Tyr Ser Leu Arg Ala Lys Val Gln Ser Glu Gly Gln Gln Glu Ala
    1610                1615                1620

Leu Glu Glu Phe Lys Ala Phe Val Asp Leu Thr Phe Pro Gly Ser
    1625                1630                1635

Val Leu Glu Asp Glu His Gln Gly Met Val His Tyr His Leu Pro
    1640                1645                1650

Gly Arg Asp Leu Ser Trp Ala Lys Val Phe Gly Ile Leu Glu Lys
    1655                1660                1665

Ala Lys Glu Lys Tyr Gly Val Asp Asp Tyr Ser Val Ser Gln Ile
    1670                1675                1680

Ser Leu Glu Gln Val Phe Leu Ser Phe Ala His Leu Gln Pro Pro
    1685                1690                1695

Thr Ala Glu Glu Gly Arg
    1700
```

US 6,713,300 B1

NUCLEIC ACID AND AMINO ACID SEQUENCES FOR ATP-BINDING CASSETTE TRANSPORTER AND METHODS OF SCREENING FOR AGENTS THAT MODIFY ATP-BINDING CASSETTE TRANSPORTER

REFERENCE TO RELATED APPLICATIONS

This Application claims benefits of U.S. Provisional Application No. 60/039,388 filed Feb. 27, 1997.

REFERENCE TO GOVERNMENT GRANTS

This work was supported in part by research grants from the Department of Health and Human Services, grant numbers DHHS #2 T32GM07330-19 and #3 T32EY07102-0553, the National Institutes of Health, grant number M01-RR00064. The United States Government may have certain rights in this invention.

BACKGROUND OF THE INVENTION

Macular degeneration affects approximately 1.7 million individuals in the U.S. and is the most common cause of acquired visual impairment in those over the age of 65. Stargardt disease (STGD; McKusick Mendelian Inheritance (MIM) #248200) is arguably the most common hereditary recessive macular dystrophy and is characterized by juvenile to young adult onset, central visual impairment, progressive bilateral atrophy of the macular retinal pigment epithelium (RPE) and neuroepithelium, and the frequent appearance of orange-yellow flecks distributed around the macula and/or the midretinal periphery (Stargardt, 1909; Anderson et al., 1995). A clinically similar retinal disorder (Fundus Flavimaculatus, FFM, Franceschetti, 1963) often displays later age of onset and slower progression (Fishman, 1976; Noble and Carr, 1979). From linkage analysis, it has been concluded that STGD and FFM are most likely allelic autosomal recessive disorders with slightly different clinical manifestations caused by mutation(s) of a gene at chromosome 1p13–p21 (Gerber et al., 1995; Anderson et al., 1995). The STGD gene has been localized to a 4 cM region flanked by the recombinant markers D1S435 and D1S236 and a complete yeast artificial chromosome (YAC) contig of the region has been constructed (Anderson et al., 1995). Recently, the location of the STGD/FFM locus on human chromosome 1p has been refined to a 2 cM interval between polymorphic markers D1S406 and D1S236 by genetic linkage analysis in an independent set of STGD families (Hoyng et al., 1996). Autosomal dominant disorders with somewhat similar clinical phenotypes to STGD, identified in single large North American pedigrees, have been mapped to chromosome 13q34 (STGD2; MIM #153900; Zhang et al., 1994) and to chromosome 6q11–q14 (STGD3; MIM #600110; Stone et al., 1994) although these conditions are not characterized by the pathognomonic dark choroid observed by fluorescein angiography (Gass, 1987).

Members of the superfamily of mammalian ATP binding cassette (ABC) transporters are being considered as possible candidates for human disease phenotypes. The ABC superfamily includes genes whose products are transmembrane proteins involved in energy-dependent transport of a wide spectrum of substrates across membranes (Childs and Ling, 1994; Dean and Allikmets, 1995). Many disease-causing members of this superfamily result in defects in the transport of specific substrates (CFTR, Riordan et al., 1989; ALD, Mosser et al., 1993; SUR, Thomas et al., 1995; PMP70, Shimozawa et al., 1992; TAP2, de la Salle et al., 1994). In eukaryotes, ABC genes encode typically four domains that include two conserved ATP-binding domains (ATP) and two domains with multiple transmembrane (TM) segments (Hyde et al., 1990). The ATP-binding domains of ABC genes contain motifs of characteristic conserved residues (Walker A and B motifs) spaced by 90–120 amino acids. Both this conserved spacing and the "Signature" or "C" motif just upstream of the Walker B site distinguish members of the ABC superfamily from other ATP-binding proteins (Hyde et al., 1990; Michaelis and Berkower, 1995). These features have allowed the isolation of new ABC genes by hybridization, degenerate PCR, and inspection of DNA sequence databases (Allikmets et al., 1993, 1995; Dean eta l., 1994; Luciani et al., 1994).

The characterization of twenty-one new members of the ABC superfamily may permit characterization and functions assigned to these genes by determining their map locations and their patterns of expression (Allikmets et al., 1996). That many known ABC genes are involved in inherited human diseases suggests that some of these new loci will also encode proteins mutated in specific genetic disorders. Despite regionally localizing a gene by mapping, the determination of the precise localization and sequence of one gene nonetheless requires choosing the certain gene from about 250 genes, four to about five million base pairs, from within the regionally localized chromosomal site.

While advancements have been made as described above, mutations in retina-specific ABC transporter (ABCR) in patients with recessive macular dystrophy STGD/FFM have not yet been identified to Applicant's knowledge. That ABCR expression is limited to photoreceptors, as determined by the present invention, provides evidence as to why ABCR has not yet been sequenced. Further, the ABC1 subfamily of ABC transporters is not represented by any homolog in yeast (Michaelis and Berkower, 1995), suggesting that these genes evolved to perform specialized functions in multicellular organisms, which also lends support to why the ABCR gene has been difficult to identify. Unlike ABC genes in bacteria, the homologous genes in higher eukaryotes are much less well studied. The fact that prokaryotes contain a large number of ABC genes suggests that many mammalian members of the superfamily remain uncharacterized. The task of studying eukaryote ABC genes is more difficult because of the significantly higher complexity of eukaryotic systems and the apparent difference in function of even highly homologous genes. While ABC proteins are the principal transporters of a number of diverse compounds in bacterial cells, in contrast, eukaryotes have evolved other mechanisms for the transport of many amino acids and sugars. Eukaryotes have other reasons to diversify the role of ABC genes, for example, performing such functions as ion transport, toxin elimination, and secretion of signaling molecules.

Accordingly, there remains a need for the identification of the sequence of the gene, which in mutated forms is associated with retinal and/or macular degenerative diseases, including Stargardt Disease and Fundus Flavimaculatus, for example, in order to provide enhanced diagnoses and improved prognoses and interventional therapies for individuals affected with such diseases.

SUMMARY OF THE INVENTION

The present invention provides sequences encoding an ATP binding cassette transporter. Nucleic acid sequences, including SEQ ID NO: 1 which is a genomic sequence, and SEQ ID NOS: 2 and 5 which are cDNA sequences, are sequences to which the present invention is directed.

A further aspect of the present invention provides ATP binding cassette transporter polypeptides and/or proteins. SEQ ID NOS: 3 and 6 are novel polypeptides of the invention produced from nucleotide sequences encoding the ATP binding cassette transporter. Also within the scope of the present invention is a purified ATP binding cassette transporter.

The present invention also provides an expression vector comprising a nucleic acid sequence encoding an ATP binding cassette transporter, a transformed host cell capable of expressing a nucleic acid sequence encoding an ATP binding cassette transporter, a cell culture capable of expressing an ATP binding cassette transporter, and a protein preparation comprising an ATP binding cassette transporter.

The present invention is also directed to a method of screening for an agent that modifies ATP binding cassette transporter comprising combining purified ATP binding cassette transporter with an agent suspected of modifying ATP binding cassette transporter and observing a change in at least one characteristic associated with ATP binding cassette transporter. The present invention provides methods of identifying an agent that inhibits macular degeneration comprising combining purified ATP binding cassette transporter from a patient suspected of having macular degeneration and an agent suspected interacting with the ATP binding cassette transporter and observing an inhibition in at least one of the characteristics of diseases associated with the ATP binding cassette transporter. In addition, the present invention provides for methods of identifying an agent that induces onset of at least one characteristic associated with ATP binding cassette transporter comprising combining purified wild-type ATP binding cassette transporter with an agent suspected of inducing a macular degenerative disease and observing the onset of a characteristic associated with macular degeneration.

BRIEF DESCRIPTION OF THE FIGURES

FIG. 1A displays a physical map of the ABCR gene. Mega-YAC clones from the CEPH mega-YAC genomic library (Bellane-Chantelot et al., 1992) encompassing the 4 cM critical region for STGD are represented by horizontal bars with shaded circles indicating confirmed positives for STSs by landmark mapping. The individual STS markers and their physical order are shown below the YACs with arrows indicating the centromeric (cen) and telomeric (1pter) direction (Anderson et al., 1995). The horizontal double head arrow labeled STGD indicates the refined genetic interval delineated by historical recombinants (Anderson et al., 1995). FIG. 1B displays the results of agarose gel electrophoresis of PCR amplification products with primers from the 5' (GGTCTTCGTGTGTGGTCATT, SEQ ID NO: 114, GGTCCAGTTCTTCCAGAG, SEQ ID NO: 115, labeled 5' AGCR) or 3' (ATCCTCTGACTCAGCAATCACA, SEQ ID NO:116, TTGCAATTACAAATGCAATGG, SEQ ID NO: 117, labeled 3' ABCR) regions of ABCR on the 13 different YAC DNA templates indicated as diagonals above the gel. Thee asterisk denotes that YAC 680_b_5 was positive for the 5' ABCR PCR but negative for the 3' ABCR PCR. These data suggest the ABCR gene maps within the interval delineated by markers D1S3361–D1S236 and is transcribed toward the telomere, as depicted by the open horizontal box.

FIGS. 3A–H shows the sequence of the ABCR coding region within the genomic ABCR sequence, SEQ ID NO: 1. The sequence of the ABCR cDNA, SEQ ID NO: 2, is shown with the predicted protein sequence, SEQ ID NO: 3, in one-letter amino acid code below. The location of splice sites is shown by the symbol |.

FIGS. 4A–D displays the alignment of the ABCR protein, SEQ ID NO:3, with other members of the ABC1 subfamily. The deduced amino acid sequence of ABCR is shown aligned to known human and mouse proteins that are members of the same subfamily. Mouse Abc1 (SEQ ID NO:118); Abc2; mouse Abc2 (SEQ ID NO:119); and ABCC, human ABC gene (SEQ ID NO:120). The Walker A and B motifs and the Signature C motif are designated by underlining and the letters A, B, and C, respectively.

FIGS. 7A–H shows the localization of ABCR transcripts to photoreceptor cells. In situ hybridization was performed with digoxygenin-labeled riboprobes and visualized using an alkaline phosphatase conjugated anti-digoxygenin antibody. FIGS. 7A–D displays hybridization results of retina and choroid from a pigmented mouse (C57/B16); FIGS. 7E and 7F shows hybridization results of retina and choroid from an albino rat; and FIGS. 7G and 7H exhibits hybridization results of retina from a macaque monkey. FIGS. 7A, 7E, and 7G display results from a mouse abcr antisense probe; FIG. 7B exhibit results from a mouse abcr sense probe; FIG. 7C shows results from a macaque rhodopsin antisensr probe; and FIGS. 7D, 7F, and 7H display results from a mouse blue cone pigment antisense probe. ABCR transcripts are localized to the inner segments of the photoreceptor cell layer, a pattern that matches the distribution of rhodopsin transcripts but is distinct from the distribution of cone visual pigment transcripts. Hybridization is not observed in the RPE or choroid, as seen most clearly in the albino rat eye (arrowhead in FIG. 7E). The retinal layers indicated in FIG. 7B are: OS, outer segments; IS, inner segments; ONL, outer nuclear layer; OPL, outer plexiform layer; INL, inner nuclear layer; IPL, inner plexiform layer; GCL, ganglion cell layer.

DETAILED DESCRIPTION OF THE INVENTION

Figures 1A, 1B:
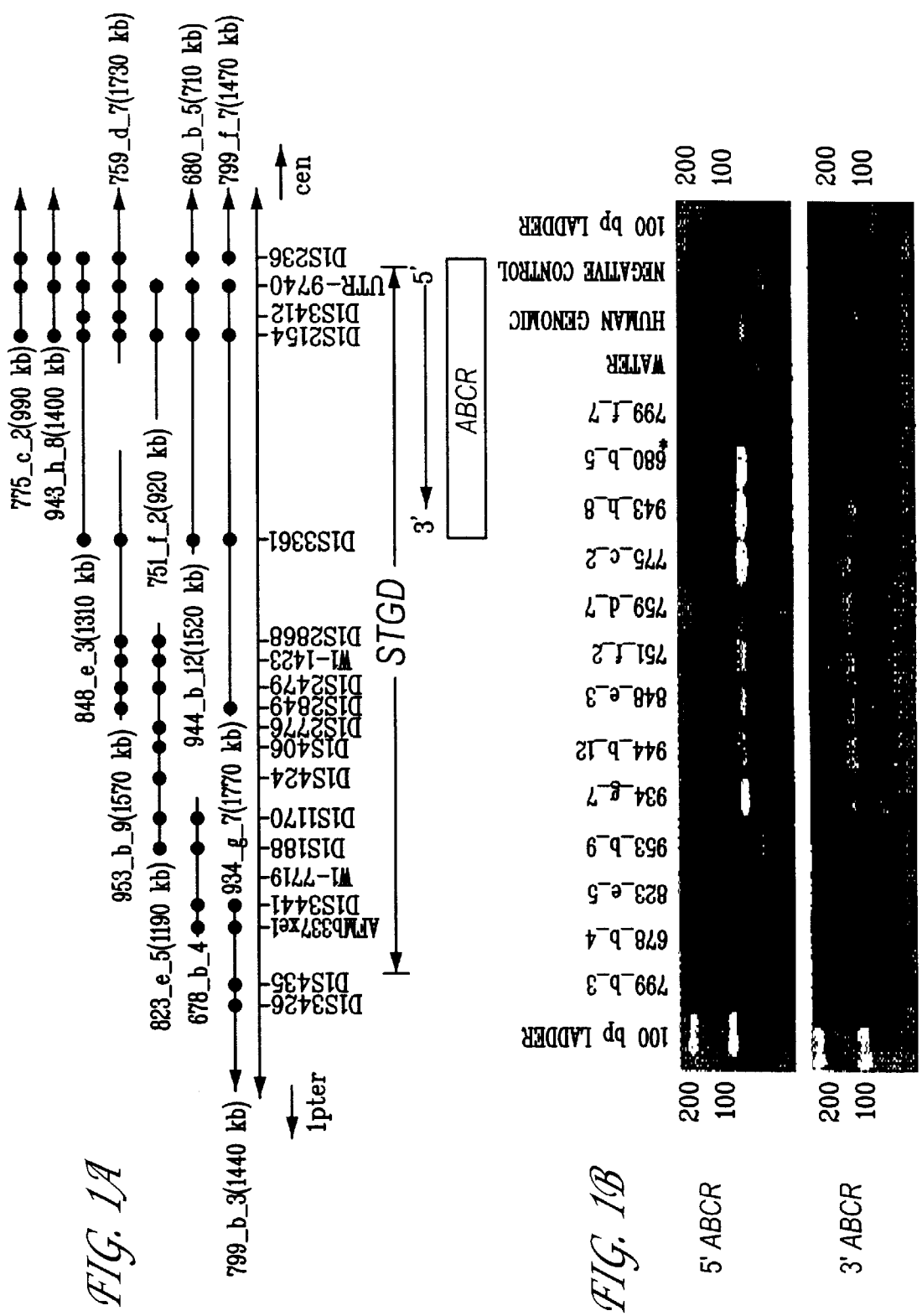
FIGS. 1A and 1B displays the ABCR gene and amplification products.

The present invention is directed to the nucleic acid and protein sequences encoding ATP binding cassette transporter. The ATP binding cassette transporter of the present invention is retina specific ATP binding cassette transporter (ABCR); more particularly, ABCR may be isolated from retinal cells, preferably photoreceptor cells. The present invention provides nucleotide sequences of ABCR including genomic sequences, SEQ ID NO: 1, and cDNA sequences SEQ ID NO: 2 and 5. Novel polypeptide sequences, SEQ ID NOS: 3 and 6, for ABCR, and the translated products of SEQ ID NOS: 2 and 5, respectively, and are also included in the present invention.

SEQ ID NO: 1 provides the human genomic DNA sequence of ABCR. SEQ ID NOS: 2 and 5 provide wild-type cDNA sequences of human ABCR, which result in translated products SEQ ID NOS: 3 and 6, respectively. While not intending to be bound by any particular theory of theories of operation, it is believed that SEQ ID NOS: 2 and 5 are isoforms of ABCR cDNA. The difference between SEQ ID NOS: 2 and 5 may be accounted for by an additional sequence in SEQ ID NO: 2 which is added between bases 4352 and 4353 of SEQ ID NO: 5. This difference is thought to arise from alternative splicing of the nascent transcript of ABCR, in which an alternative exon 30, SEQ ID NO: 4, is excluded. This alternative exon encodes an additional 38 amino acids, SEQ ID NO: 11.

Nucleic acids within in the scope of the present invention include cDNA, RNA, genomic DNA, fragments or portions within the sequences, antisense oligonucleotides. Sequences encoding the ABCR also include amino acid, polypeptide, and protein sequences. Variations in the nucleic acid and polypeptide sequences of the present invention are within the scope of the present invention and include N terminal and C terminal extensions, transcription and translation modifications, and modifications in the cDNA sequence to facilitate and improve transcription and translation efficiency. In addition, changes within the wild-type sequences identified herein which changed sequence retains substantially the same wild-type activity, such that the changed sequences are substantially similar to the ABCR sequences identified, are also considered within the scope of the present invention. Mismatches, insertions, and deletions which permit substantial similarity to the ABCR sequences, such as similarity in residues in hydrophobicity, hydrophilicity, basicity, and acidity, will be known to those of skill in the art once armed with the present disclosure. In addition, the isolated, or purified, sequences of the present invention may be natural, recombinant, synthetic, or a combination thereof. Wild-type activity associated with the ABCR sequences of the present invention include, inter alia, all or part of a sequence, or a sequence substantially similar thereto, that codes for ATP binding cassette transporter.

The genomic, SEQ ID NO: 1, and cDNA, SEQ ID NOS: 2 and 5, sequences are identified in FIG. 3 and encode ABCR, certain mutations of which are responsible for the class of retinal disorders known as retinal or macular degenerations. Macular degeneration is characterized by macular dystrophy, various alterations of the peripheral retina, central visual impairment, progressive bilateral atrophy of the macular retinal pigment epithelium (RPE) and neuroepithelium, frequent appearance of orange-yellow flecks distributed around the macula and/or the midretinal periphery, and subretinal deposition of lipfuscin-like material. Retinal and macular degenerative diseases include and are mot limited to Stargardt Disease, Fundus Flavimaculatus, age-related macular degeneration, and may include disorders variously called retinitis pigmentosa, combined rod and cone dystrophies, cone dystrophies and degenerations, pattern dystrophy, bull's eye maculopathies, and various other retinal degenerative disorders, some induced by drugs, toxins, environmental influences, and the like. Stargardt Disease is an autosomal recessive retinal disorder characterized by juvenile to adult-onset macular and retinal dystrophy. Fundus Flavimaculatus often displays later age of onset and slower progression. Some environmental insults and drug toxicities may create similar retinal degenerations. Linkage analysis reveals that Stargardt Disease and Fundus Flavimaculatus may be allelic autosomal recessive disorders with slightly different clinical manifestations. The identification of the ABCR gene suggests that different mutations within ABCR may be responsible for these clinical phenomena.

The present invention is also directed to a method of screening for an agent that modifies ATP binding cassette transporter comprising combining purified ATP binding cassette transporter with an agent of modifying ATP binding cassette transporter and observing a change in at least one characteristic associated with ATP binding cassette transporter.

"Modify" and variations thereof include changes such as and not limited to inhibit, suppress, delay, retard, slow, suspend, obstruct, and restrict, as well as induce, encourage, provoke, and cause. Modified may also be defined as complete inhibition such that macular degeneration is arrested, stopped, or blocked. Modifications may, directly or indirectly, inhibit or substantially inhibit, macular degeneration or induce, or substantially induce, macular degeneration, under certain circumstances.

Methods of identifying an agent that inhibits macular degeneration are embodied by the present invention and comprise combining purified ATP binding cassette transporter from a patient suspected of having macular degeneration and an agent suspected of interacting with the ATP binding cassette transporter and observing an inhibition in at least one of the characteristics of diseases associated with the ATP binding cassette transporter. Accordingly, such methods serve to reduce or prevent macular degeneration, such as in human patients. In addition, the present invention provides for methods of identifying an agent that induces onset of at least one characteristic associated with ATP binding cassette transporter comprising combining purified wild-type ATP binding cassette transporter with an agent suspected of inducing a macular degenerative disease and observing the onset of a characteristic associated with macular degenerative. Thus, such methods provide methods of using laboratory animals to determine causative agents of macular degeneration. The ATP binding cassette transporter may be provided for in the methods identified herein in the form of nucleic acids, such as and not limited to SEQ ID NOS: 1, 2, and 5 or as an amino acid, SEQ ID NOS: 3 and 6, for example. Accordingly, transcription and translation inhibitors may be separately identified. Characteristics associated with macular degeneration include and are not limited to central visual impairment, progressive bilateral atrophy of the macular retinal pigment epithelium (RPE) and neuroepithelium, and the frequent appearance of orange-yellow flecks distributed around the macula and/or the midretinal periphery. Accordingly, observing one or more of the characteristics set forth above results in identification of an agent that induces macular degeneration, whereas reduction or inhibition of at least one of the characteristics results in identification of an agent that inhibits macular degeneration.

Mutational analysis of ABCR in Stargardt Disease families revealed thus far seventy four mutations including fifty four single amino acid substitutions, five nonsense mutations resulting in early truncation of the protein, six frame shift mutations resulting in early truncation of the protein, three in-frame deletions resulting in loss of amino acid residues from the protein, and six splice site mutations resulting in incorrect processing of the nascent RNA transcript, see Table 2. Compound heterozygotes for mutations in ABCR were found in forty two families. Homozygous mutations were identified in three families with consanguineous parentage. Accordingly, mutations in wild-type ABCR which result in activities that are not associated with wild-type ABCR are herein referred to as sequences which are associated with macular degeneration. Such mutations include missense mutations, deletions, insertions, substantial differences in hydrophobicity, hydrophilicity, acidity, and basicity. Characteristics which are associated with retinal or macular degeneration include and are not limited to those characteristics set forth above.

Mutations in wild-type ABCR provide a method of detecting macular degeneration. Retinal or macular degeneration may be detected by obtaining a sample comprising patient nucleic acids from a patient tissue sample; amplifying retina-specific ATP binding cassette receptor specific nucleic acids from the patient nucleic acids to produce a test fragment; obtaining a sample comprising control nucleic acids from a control-tissue sample; amplifying control nucleic acids encoding wild-type retina-specific ATP binding cassette receptor to produce a control fragment; comprising the test fragment with the control fragment to detect the presence of a sequence difference in the test fragment, wherein a difference in the test fragment indicates macular degeneration. Mutations in the test fragment, including and not limited to each of the mutations identified above, may provide evidence of macular degeneration.

A purified ABCR protein is also provided by the present invention. The purified ABCR provides may have an amino acid sequence as provided by SEQ ID NOS: 3 and 6.

The present invention is directed to ABCR sequences obtained from mammals from the Order Rodentia, including and not limited to hamsters, rats, and mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

Generally, the sequences of the invention may be produced in host cells transformed with an expression vector comprising a nucleic acid sequence encoding ABCR. The transformed cells are cultured under conditions whereby the nucleic acid sequence coding for ABCR is expressed. After a suitable amount of time for the protein to accumulate, the protein may be purified from the transformed cells.

A gene coding for ABCR may be obtained from cDNA library. Suitable libraries can be obtained from commercial sources such as Clontech, Palo Also, Calif. Libraries may also be prepared using the following non-limiting examples: hamster insulin-secreting tumor (HIT), mouse αTC-6, and rat insulinoma (RIN) cells. Positive clones are then subjected to DNA sequencing to determine the presence of a DNA sequence coding for ABCR. DNA sequencing is accomplished using the chain termination method of Sanger et al., *Proc. Nat'l. Acad. Sci. U.S.A.*, 1977, 74, 5463. The DNA sequence encoding ABCR is then inserted into an expression vector for later expression in a host cell.

Expression vectors and host cells are selected to form an expression system capable of synthesizing ABCR. Vectors including and not limited to baculovirus vectors may be used in the present invention. Host cells suitable for use in the invention include prokaryotic and eukaryotic cells that can be transformed to stably contain the express ABCR. For example, nucleic acids coding for the recombinant protein may be expressed in prokaryotic or eukaryotic host cells, including the most commonly used bacterial host cell for the production of recombinant proteins, *E. coli*. Other microbial strains may also be used, however, such as *Bacillus subtilis*, and other enterobacteriaceae such as *Salmonella typhimurium* or *Serratia marcesens*, various species of Pseudomonas, or other bacterial strains.

The preferable eukaryotic system is yeast, such as *Saccharomyces cerevisiae*. Yeast artificial chromosome (YAC) systems are able to accommodate the large size of ABCR gene sequence or genomic clone. The principle of the YAC system is similar to that used in conventional cloning of DNA. Large fragments of cDNA are ligated into two "arms" of a YAC vector, and the ligation mixture is then introduced into the yeast by transformation. Each of the arms of the YAC vector carries a selectable marker as well as appropriately oriented sequences that function as telomeres in yeast. In addition, one of the two arms carries two small fragments that function as a centromere and as an origin of replication (also called an ARS element-autonomously replicating sequences). Yeast transformants that have taken up and stably maintained an artificial chromosome are identified as colonies on agar plates containing the components necessary for selection of one or both YAC arms. YAC vectors are designed to allow rapid identification of transformants that carry inserts of genomic DNA. Insertion of genomic DNA into the cloning site interrupts a suppressor tRNA gene and results in the formation of red rather than white colonies by yeast strains that carry an amber ade2 gene.

To clone in YAC vectors, genomic DNA from the test organism is prepared under conditions that result in relatively little shearing such that its average size is several million base pairs. The cDNA is then ligated to the arms of the YAC vector, which has been appropriately prepared to prevent self-ligation. As an alternative to partial digestion with EcoRI, YAC vectors may be used that will accept genomic DNA that has been digested to completion with rarely cutting restriction enzymes such as NotI or MluI.

In addition, insect cells, such as *Spodoptera frugiperda*; chicken cells, such as E3C/O and SL-29; mammalian cells, such as HeLa, Chinese hamster ovary cells (CHO), COS-7 or MDCK cells and the like may also be used. The foregoing list is illustrative only and is not intended in any way to limit the types of host cells suitable for expression of the nucleic acid sequences of the invention.

As used herein, expression vectors refer to any type of vector that can be manipulated to contain a nucleic acid sequence coding for ABCR, such as plasmid expression vectors, viral vectors, and yeast expression vectors. The selection of the expression vector is based on compatibility with the desired host cell such that expression of the nucleic acid encoding ABCR results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol, or kanamycin resistance.

Suitable expression vectors, promoters, enhancers, and other expression control elements are known in the art and may be found in Sambrook et al., *Molecular Cloning: A Laboratory Manual,* second edition, Cold Spring Harbor Laboratory Press, Cold Spring Harbor, N.Y. (1989), incorporated herein by reference in its entirety.

Transformed host cells containing a DNA sequence encoding ABCR may then be grown in an appropriate medium for the host. The cells are then grown until product accumulation reaches desired levels at which time the cells are then harvested and the protein product purified in accordance with conventional techniques. Suitable purification methods include, but are not limited to, SDS PAGE electrophoresis, phenylboronate-agarose, reactive green 19-agarose, concanavalin A sepharose, ion exchange chromatography, affinity chromatography, electrophoresis, dialysis and other methods of purification known in the art.

Protein preparations, of purified or unpurified ABCR by host cells, are accordingly produced which comprise ABCR and other material such as host cell components and/or cell medium, depending on the degree of purification of the protein.

The invention also includes a transgenic non-human animal, including and not limited to mammals, such as and not limited to a mouse, rat, or hamster, comprising a sequence encoding ABCR, or fragment thereof that substantially retains ABCR activity, introduced into the animal or an ancestor of the animal. The sequence may be wild-type or mutant and may be introduced into the animal at the embryonic or adult stage. The sequence is incorporated into the genome of an animal such that it is chromosomally incorporated into an activated state. A transgenic non-human animal has germ cells and somatic cells that contain an ABCR sequence. Embryo cells may be transfected with the gene as it occurs naturally, and transgenic animals are selected in which the gene has integrated into the chromosome at a locus which results in activation. Other activation methods include modifying the gene or its control sequences prior to introduction into the embryo. The embryo may be transfected using a vector containing the gene.

In addition, a transgenic non-human animal may be engineered wherein ABCR is suppressed. For purposes of the present invention, suppression of ABCR includes, and is not limited to strategies which cause ABCR not to be expressed. Such strategies may include and are not limited to inhibition of protein synthesis, pre-mRNA processing, or DNA replication. Each of the above strategies may be accomplished by antisense inhibition of ABCR gene expression. Many techniques for transferring antisense sequences into cells are known to those of skill, including and not limited to microinjection, viral-medicated transfer, somatic cell transformation, transgene integration, and the like, as set forth in Pinkert, Carl, *Transgenic Animal Technology,* 1994, Academic Press, Inc., San Diego, Calif., incorporated herein by reference in its entirety.

Further, a transgenic non-human animal may be prepared such that ABCR is knocked out. For purposes of the present invention, a knock-out includes and is not limited to disruption or rendering null the ABCR gene. A knock-out may be accomplished, for example, with antisense sequences for ABCR. The ABCR gene may be knocked out by injection of an antisense sequence for all or part of the ABCR sequence such as an antisense sequence for all or part of SEQ ID NO: 2. Once ABCR has been rendered null, correlation of the ABCR to macular degeneration may be tested. Sequences encoding mutations affecting the ABCR may be inserted to test for alterations in various retinal and macular degenerations exhibited by changes in the characteristics associated with retinal and macular degeneration.

An ABCR knock-out may be engineered by inserting synthetic DNA into the animal chromosome by homologous recombination. In this method, sequences flanking the target and insert DNA are identical, allowing strand exchange and crossing over to occur between the target and insert DNA. Sequences to be inserted typically include a gene for a selectable marker, such as drug resistance. Sequences to be targeted are typically coding regions of the genome, in this case part of the ABCR gene. In this process of homologous recombination, targeted sequences are replaced with insert sequences thus disrupting the targeted gene and rendering it nonfunctional. This nonfunctional gene is called a null allele of the gene.

To create the knockout mouse, a DNA construct containing the insert DNA and flanking sequences is made. This DNA construct is transfected into pluripotent embryonic stem cells competent for recombination. The identical flanking sequences align with one another, and chromosomal recombination occurs in which the targeted sequence is replaced with the insert sequence, as described in Bradley, A., Production and Analysis of Chimeric Mice, in *Tetracarbinomas and Embryonic Stem Cells—A Practical Approach,* 1987, E. Roberson, Editor, IRC Press, pages 113–151. The stem cells are injected into an embryo, which is then implanted into a female animal and allowed to be born. The animals may contain germ cells derived from the injected stem cells, and subsequent matings may produce animals heterozygous and homozygous for the disrupted gene.

Transgenic non-human animals may also be useful for testing nucleic acid changes to identify additional mutations responsible for macular degeneration. A transgenic non-human animal may comprise a recombinant ABCR.

The present invention is also directed to gene therapy. For purposes of the present invention, gene therapy refers to the transfer and stable insertion of new genetic information into cells for the therapeutic treatment of diseases or disorders. A foreign sequence or gene is transferred into a cell that proliferates to spread the new sequence or gene throughout the cell population. Sequences include antisense sequence of all or part of ABCR, such as an antisense sequence to all or part of the sequences identified as SEQ ID NO: 1, 2, and 5. Known methods of gene transfer include microinjection, electroporation, liposomes, chromosome transfer, transfection techniques, calcium-precipitation transfection techniques, and the like. In the instant case, macular degeneration may result from a loss of gene function, as a result of a mutation for example, or a gain of gene function, as a result of an extra copy of a gene, such as three copies of a wild-type gene, or a gene over expressed as a result of a mutation in a promoter, for example. Expression may be altered by activating or deactivating regulatory elements, such as a promoter. A mutation may be corrected by replacing the mutated sequence with a wild-type sequence or inserting an antisense sequence to bind to an over expressed sequence or to a regulatory sequence.

Numerous techniques are known in the art for the introduction of foreign genes into cells and may be used to construct the recombinant cells for purposes of gene therapy, in accordance with this embodiment of the invention. The technique used should provide for the stable transfer of the heterologous gene sequence to the stem cell, so that the heterologous gene sequence is heritable and expressible by stem cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, M. J., 1985, Pharmac. Ther. 29:69–92, incorporated herein by reference in its entirety).

The term "purified", when used to describe the state of nucleic acid sequences of the invention, refers to nucleic acid sequences substantially free of nucleic acid not coding for ABCR or other materials normally associated with nucleic acid in non-recombinant cells, i.e., in its "native state."

The term "purified" or "in purified form" when used to describe the state of an ABCR nucleic acid, protein, polypeptide, or amino acid sequence, refers to sequences substantially free, to at least some degree, of cellular material or other material normally associated with it in its native state. Preferably the sequence has a purity (homogeneity) of at least about 25% to about 100%. More preferably the purity is at least about 50%, when purified in accordance with standard techniques known in the art.

In accordance with methods of the present invention, methods of detecting retinal or macular degenerations in a patient are provided comprising obtaining a patient tissue sample for testing. The tissue sample may be solid or liquid, a body fluid sample such as and not limited to blood, skin, serum, saliva, sputum, mucus, bone narrow, urine, lymph, and a tear; and feces. In addition, a tissue sample from amniotic fluid or chorion may be provided for the detection or retinal or macular degeneration in utero in accordance with the present invention.

A test fragment is defined herein as an amplified sample comprising ABCR-specific nucleic acids from a patient suspected of having retinal or macular degeneration. A control fragment is an amplified sample comprising normal or wild-type ABCR-specific nucleic acids from an individual not suspected of having retinal or macular degeneration.

The method of amplifying nucleic acids may be the polymerase chain reaction using a pair of primers wherein at least one primer within the pair is selected from the group consisting of SEQ ID NOS: 12–113. When the polymerase chain reaction is the amplification method of choice, a pair of primers may be used such that one primer of the pair is selected from the group consisting of SEQ ID NOS: 12–113.

Nucleic acids, such as DNA (such as and not limited to, genomic DNA and cDNA) and/or RNA (such as, and not limited to, mRNA), are obtained from the patient sample. Preferably RNA is obtained.

Nucleic acid extraction is followed by amplification of the same by any technique known in the art. The amplification step includes the use of at least one primer sequence which is complementary to a portion of ABCR-specific expressed nucleic acids or sequences on flanking intronic genomic sequences in order to amplify exon or coding sequences. Primer sequences useful in the amplification methods include and are not limited to SEQ ID NOS: 12–113, which may be used in the amplification methods. Any primer sequence of about 10 nucleotides to about 35 nucleotides, more preferably about 15 nucleotides to about 30 nucleotides, even more preferably about 17 nucleotides to about 25 nucleotides may be useful in the amplification step of the methods of the present invention. In addition, mismatches within the sequences identified above, which achieve the methods of the invention, such that the mismatched sequences are substantially complementary and thus hybridizable to the sequence sought to be identified, are also considered within the scope of the disclosure. Mismatches which permit substantial similarity to SEQ ID NOS: 12–113, such as and not limited to sequences with similar hydrophobicity, hydrophilicity, basicity, and acidity, will be known to those of skill in the art once armed with the present disclosure. The primers may also be unmodified or modified. Primers may be prepared by any method known in the art such as by standard phosphoramidite chemistry. See Sambrook et al., supra.

The method of amplifying nucleic acids may be the polymerase chain reaction using a pair of primers wherein at least one primer within the pair is selected from the group consisting of SEQ ID NOS: 12–113. When the polymerase chain reaction is the amplification method of choice, a pair of primers may be used such that one primer of the pair is selected from the group consisting of SEQ ID NOS: 12–113.

When an amplification method includes the use of two primers, a first primer and a second primer, such as in the polymerase chain reaction, one of the first primer or second primer may be selected from the group consisting of SEQ ID NOS: 12–113. Any primer pairs which copy and amplify nucleic acids between the pairs pointed toward each other and which are specified for ABCR may be used in accordance with the methods of the present invention.

A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., PCR Protocols, Academic Press, Inc., San Diego Calif., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Alternatively, a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Application No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[alpha-thio]triphosphates in one strand of a restriction site (Walker, G. T., et al., *Proc. Natl. Acad, Sci.* (*U.S.A.*) 1992, 89:392–396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and which involves annealing several probes throughout a region targeted for amplification, followed by a repair reaction in which only two of the four bases are present. The other two bases can be added as biotinylated derivatives for easy detection. A similar approach is used in SDA.

ABCR-specific nucleic acids can also be detected using a cyclic probe reaction (CPR). In CPR, a probe having a 3' and 5' sequences of non-ABCR specific DNA and middle sequence of ABCR specific RNA is hybridized to DNA which is present in a sample. Upon hybridization, the reaction is treated with RNaseH, and the products of the probe identified as distinctive products, generate a signal which is released after digestion. The original template is annealed to another cycling probe and the reaction is repeated. Thus, CPR involves amplifying a signal generated by hybridization of a probe to a ABCR-specific expressed nucleic acid.

Still other amplification methods described in GB Application No. 2 202 328, and in PCT Application No. PCT/US89/01025, each of which is incorporated by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh D., et al., *Proc. Natl. Acad. Sci.* (U.S.A.) 1989, 86:1173, Gingeras T. R., et al., PCT Application WO 88/10315, each of which is incorporated herein by reference in its entirety), including nucleic acid sequence based amplification (NASBA) and 3SR. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has ABCR-specific sequences. Following polymerization, DNA/RNA hybrids are digested with RNase H while double standard DNA molecules are heat denatured again. In either case the single stranded DNA is made fully double stranded by addition of second ABCR-specific primer, followed by polymerization. The double standard DNA molecules are then multiply transcribed by a polymerase such as T7 or SP6. In an isothermal cyclic reaction, the RNAs are reverse transcribed into double stranded DNA, and transcribed once again with a polymerase such as T7 or SP6. The resulting products, whether truncated or complete, indicate ABCR-specific sequences.

Davey, C., et al., European Patent Application Publication No. 329,822, incorporated herein by reference in its entirety, disclose a nucleic acid amplification process involving cyclically synthesizing single-stranded RNA ("ssRNA"), ssDNA, and double-stranded DNA ("dsDNA") which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenox" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A. In: *PCR Protocols: A Guide to Methods and Applications* 1990, Academic Press, N.Y.) and "one-sided PCR" (Ohara, O., et al., *Proc. Natl. Acad. Sci.* (U.S.A.) 1989, 86:57673–5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., *Genomics* 1989, 4:560, incorporated herein by reference in its entirety), may also be used in the amplification step of the present invention.

Test fragment and control fragment may be amplified by any amplification methods known to those of skill in the art, including and not limited to the amplification methods set forth above. For purposes of the present invention, amplification of sequences encoding patient and wild-type ABCR includes amplification of a portion of a sequence such as and not limited to a portion of an ABCR sequence of SEQ ID NO:1, such as sequence of a length of about 10 nucleotides to about 1,000 nucleotides, more preferably about 10 nucleotides to about 100 nucleotides, or having at least 10 nucleotides occurring anywhere within the SEQ ID NO:1, where sequence differences are known to occur within ABCR test fragments. Thus, for example, a portion of the sequence encoding ABCR of a patient sample and a control sample may be amplified to detect sequence differences between these two sequences.

Following amplification of the test fragment and control fragment, comparison between the amplification products of the test fragment and control fragment is carried out. Sequence changes such as and not limited to nucleic acid transition, transversion, and restriction digest pattern alterations may be detected by comparison of the test fragment with the control fragment.

Alternatively, the presence or absence of the amplification product may be detected. The nucleic acids are fragmented into vary sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labeled probe encoding an ABCR mutation is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 500 nucleotides in length, and more preferably about 2,454 nucleotides in length. Mismatches which permit substantial similarity to the probe, such as and not limited to sequences with similar hydrophobicity, hydrophilicity, basicity, and acidity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}P$ labeling, and the like. Preferably, the product such as the PCR product, may be run on an agarose gel and visualized using a strain such as ethidium bromide. See Sambrook et al., supra. The matrix may then be analyzed by autoradiography to locate particular fragments which hybridize to the probe. Yet another alternative is the sequencing of the test fragment and the control fragment to identify sequence differences. Methods of nucleic acid sequencing are known to those of skill in the art, including and not limited to the methods of Maxam and Filbert, *Proc. Natl. Acad. Sci. USA* 1977, 74, 560–564 and Sanger, *Proc. Natl. Acad. Sci., USA* 1977, 74, 5463–5467.

A pharmaceutical composition comprising all or part of a sequence for ABCR may be delivered to a patient suspected of having retinal or macular degeneration. The sequence may be an antisense sequence. The composition of the present invention may be administered alone or may generally be administered in admixture with a pharmaceutical carrier. The pharmaceutically-acceptable carrier may be selected with regard to the intended route of administration and the standard pharmaceutical practice. The dosage will be about that of the sequence alone and will be set with regard to weight, and clinical condition of the patient. The proportional ratio of active ingredient to carrier will naturally depend, inter alia, on the chemical nature, solubility, and stability of the sequence, as well as the dosage contemplated.

The sequences of the invention may be employed in the method of the invention singly or in combination with other compounds, including and not limited to other sequences set forth in the present invention. The method of the invention may also be used in conjunction with other treatments such as and not limited to antibodies, for example. For in vivo applications the amount to be administered will also depend on such factors as the age, weight, and clinical condition of the patient. The composition of the present invention may be administration by any suitable route, including as an eye drop, inoculation and injection, for example, intravenous, intraocular, oral, intraperitoneal, intramuscular, subcutaneous, topically, and by absorption through epithelial or mucocutaneous linings, for example, conjunctival, nasal, oral, vaginal, rectal and gastrointestinal.

The mode of administration of the composition may determine the sites in the organism to which the compound will be delivered. For instance, topical application may be administered in creams, ointments, gels, oils, emulsions, pastes, lotions, and the like. For parenteral administration, the composition may be used in the form of sterile aqueous or non-aqueous solution which may contain another solute, for example, sufficient salts, glucose or dextrose to make the solution isotonic. A non-aqueous solution may be comprise an oil, for example. For oral mode of administration, the present invention may be used in the form of tablets, capsules, lozenges, troches, powders, syrups, elixirs, aqueous solutions and suspension, and the like. Various disintegrants, such as starch, and lubricating agents may be used. For oral administration in capsule form, useful diluents are lactose and high molecular weight polyethylene glycols. When aqueous suspensions are required for oral use, certain sweetening and/or flavoring agents may be added.

A diagnostic kit for detecting retinal or macular degeneration comprising in one or more containers at least one primer which is complementary to an ABCR sequence and a means for visualizing amplified DNA is also within the scope of the present invention. Alternatively, the kit may comprise two primers. In either case, the primers may be selected from the group consisting of SEQ ID NOS:12–113, for example. The diagnostic kit may comprise a pair of primers wherein one primer within said pair is complementary to a region of the ABCR gene, wherein one of said pair of primers is selected from the group consisting of SEQ ID NO: 12–113, a probe specific to the amplified product, and a means for visualizing amplified DNA, and optionally including one or more size markers, and positive and negative controls. The diagnostic kit of the present invention may comprise one or more of a fluorescent dye such as ethidium bromide stain, $^{32}P$, and biotin, as a means for visualizing or detecting amplified DNA. Optionally the kit may include one or more size markers, positive and negative controls, restriction enzymes, and/or a probe specific to the amplified product.

The following examples are illustrative but are not meant to be limiting of the invention.

EXAMPLES

Identification of the ABCR as a Candidate Gene for STGD

One of the 21 new human genes from the ABC superfamily, hereafter called ABCR (retina-specific ABC transporter), was identified (Allikmets et al. 1996) among expressed sequence tags (ESTs) obtained from 5,000 human retina cDNA clones (Wang, Y., Macke, J. P., Abella, B. S., Andreasson, K., Worley, P., Gilbert, D. J., Copeland, N. G., Jenkins, N. A., and Nathans, J. (1996)) and among ESTs obtained from human retina cDNA clones by the I.M.A.G.E. consortium (Lennon et al., 1996). ABCR is closely related to the previously described mouse and human ABC1 and ABC2 genes (Luciani et al., 1994; Allikmets et al., 1995). To determine whether ABCR might cause a disease, the gene was mapped with a whole genome radiation hybrid panel (GeneBridge 4; Research Genetics, Huntsville, Ala.). ABCR mapped to the human chromosome 1p13-p21 region, close to microsatellite markers D1S236 and D1S188. To define further the location of the gene, PCR primers, 3'UTR-For 5'ATCCTCTGACTCAGCAATCACA, SEQ ID NO: 7, and 3'UTR-Rev 5'TTGCAATTACAAATGCAATGG, SEQ ID NO:8, from the putative 3' untranslated region were used to screen YACs from the previously described contig between these anonymous markers (Anderson et al., 1995). At least 12 YACs contain the 3' end of the ABCR gene, including 924_e_9, 759_d_7, 775_c_2, 782_b_4, 982_g_5, 775_b_2, 765_a_3, 751_f_2, 848_e_3, 943_h_8, 934_g_7, and 944_b_12 (FIG. 1). These YACs delineate a region containing the STGD gene between markers D1S3361 and D1S236 (Anderson et al., 1995).

Expression of the ABCR Gene

Additional support suggesting that ABCR is a candidate STGD gene came from expression studies and inspection of the EST databases.

Searches of the dbEST (Boguski et al., 1993) database were performed with BLAST on the NCBI file server (Altschul et al., 1990). Amino acid alignments were generated with PILEUP (Feng and Doolittle, 1987). Sequences were analyzed with programs of the Genetics Computer Group package (Devereaux et al., 1984) on a VAX computer.

Clones corresponding to the mouse ortholog of the human ABCR gene were isolated from the mouse retina cDNA library and end-sequenced. The chromosomal location of the mouse ABCR gene was determined on The Jackson Laboratory (Bar Harbor, Me.) interspecific backcross mapping panel (C57BL/6JEi X SPRET/Ei)F1 X SPRET/Ei (Rowe et al., 1994) known as Jackson BSS. Mapping was performed by SSCP analysis with the primers MABCR1F 5'ATC CAT ACC CTT CCC ACT CC, SEQ ID NO:9, and MABCR1R 5'GCA GCA GAA GAT AAG CAC ACC, SEQ ID NO. 10. The allele pattern of the Abcr was compared to the 250 other loci mapped previously in the Jackson BSS cross (http://www.jax.org).

DNA fragments used as probes were purified on a 1% low-melting temperature agarose gel. The probe sequences are set forth within the genomic sequence of SEQ ID NO: 1 and FIG. 3. DNA was labeled directly in agarose with the Random Primed DNA Labeling Kit (Boehringer Mannheim, Indianapoils, Ind.) and hybridized to multiple tissue Northern blot and a Master blot (Clontech, Palo Alto, Calif.), according to the manufacturer's instructions. Each blot contained 2 µg of poly A⁺ RNA from various human tissues. Total RNA was isolated from adult rat tissues using the guanidinium thiocyanate method (Choezynski and Saachi, 1987and resolved by agarose gel electrophoresis in the presence of formaldehyde (Sambrook et al., 1989). Hybridization with the mouse ABCR probe was performed in 50% formamide, 5X SSC at 42° C., and filters were washed in 0.1X SSC at 68° C.

Figure 2:
FIG. 2 exhibits the size and tissue distribution of ABCR transcripts in the adult rat. A blot of total RNA from the indicated tissues was hybridized with a 1.6 kb mouse Abcr probe (top) and a ribosomal protein S26 probe (bottom; Kuwano et al., 1985). The ABCR probe revealed a predominant transcript of approximately 8 kb that is found in retina only. The mobility of the 28S and 18S ribosomal RNA are indicated at the right. B, brain; H, heart; K, kidney; Li, liver; Lu, lung; R, retina; S. spleen.

Hybridization of a 3'ABCR cDNA probe to a multiple tissue Northern blot and a MasterBlot (Clontech, Palo Alto, Calif.) indicated that the gene was not expressed detectably in any of the 50 non-retinal fetal and adult tissues examined, consistent with the observation that all 12 of the ABCR clones in the EST database originated from retinal cDNA libraries. Furthermore, screening cDNA libraries from both developing mouse eye and adult human retina with ABCR probes revealed an estimated at 0.1%–1% frequency of ABCR clones of all cDNA clones in the library. Hybridization of the ABCR probe to a Northern blot containing total RNA from rat retina and other tissues showed that the expression of this gene is uniquely retina-specific (FIG. 2). The transcript size is estimated to be 8 kb.

Sequence and Exon/Intron Structure of the ABCR cDNA

Several ESTs that were derived from retina cDNA libraries and had high similarity to the mouse Abcl gene were used to facilitate the assembly of most of the ABCR cDNA sequence. Retina cDNA clones were linked by RT-PCR, and repetitive screening of a human retina cDNA library with 3' and 5' PCR probes together with 5' RACE were used to characterize the terminal sequences of the gene.

cDNA clones containing ABCR sequences were obtained from a human retina cDNA library (Nathans et al., 1986) and sequenced fully. Primers were designed from the sequences of cDNA clones from 5' and 3' regions of the gene and used to link the identified cDNA clones by RT-PCR with retina QUICK-Clone cDNA (Clontech, Palo Alto, Calif.) as a template. PCR products were cloned into pGEM®-T vector (Promega, Madison, Wis.). Mouse ABCR cDNA clones were obtained from screening a developing mouse eye cDNA library (H. Sun, A. Lanahan, and J. Nathans, unpublished). The pGEM®-T Vector is prepared by cutting pGEM®-5Zf(+) DNA with EcoR V and adding to a 3' terminal thymidine to both ends. These single 3'-T overhangs at the insertion site greatly improve the efficiency of ligation of PCR products because of the nontemplate-dependent addition of a single deoxyadenosine (A) to the 3'-ends of PCR products by many thermostable polymerases. The pGEM®-5Zf(+) Vector contains the origin of replication of the filamentous phage f1 and can be used to produce ssDNA. The plasmid also contains T7 and SP6 RNA polymerase promoters flanking a multiple cloning region within the α-peptide coding region for the enzyme β-galactosidase. Insertional inactivation of the α-peptide allows recombinant clones to be identified directly by color screening on indicator plates. cDNA clones from various regions of the ABCR gene were used as probes to screen a human genomic library in Lambda FIX II (#946203, Stratagene, LaJolla, Calif.). Overlapping phase clones were mapped by EcoRI and BamHI digestion. A total of 6.9 kb of the ABCR sequence was assembled, (FIG. 3) resulting in a 6540 bp (2180 amino acid) open reading frame.

Screening of a bacteriophage lambda human genomic library with cDNA probes yielded a contig that spans approximately 100 kb and contains the majority of the ABCR coding region. The exon/intron structure of all fifty one exons of the gene were characterized by direct sequencing of genomic and cDNA clones. Intron sizes were estimated from the sizes of PCR products using primers from adjacent exons with genomic phage clones as templates.

Primers for the cDNA sequences of the ABCR were designed with the PRIMER program (Lincoln et al., 1991). Both ABCR cDNA clones and genomic clones became templates for sequencing. Sequencing was performed with the Taq Dyedeoxy Terminator Cycle Sequencing kit (Application Biosystems, Foster City, Calif.), according to the manufacturer's instructions. Sequencing reactions were resolved on an ABI 373A automated sequencer. Positions of introns were determined by comparison between genomic and cDNA sequences. Primers for amplification of individual exons were designed from adjacent intron sequences 20–50 bp from the splice site and are set forth in Table 1.

TABLE 1

Exon/intron Primers for ABCR

| PRIMER | SEQUENCE | SEQ ID NO |
|---|---|---|
| ABCR.EXON1:F | ACCCTCTGCTAAGCTCAGAG | 12 |
| ABCR.EXON1:R | ACCCCACACTTCCAACCTG | 13 |
| ABCR.EXON2:F | AAGTCCTACTGCACACATGG | 14 |
| ABCR.EXON2:R | ACACTCCCACCCCAAGATC | 15 |
| ABCR.EXON3:F | TTCCCAAAAAGGCCAACTC | 16 |
| ABCR.EXON3:R | CACGCACGTGTGCATTCAG | 17 |
| ABCR.EXON4:F | GCTATTTCCTTATTAATGAGGC | 18 |
| ABCR.EXON4:R | CCAACTCTCCCTGTTCTTTC | 19 |
| ABCR.EXON5:F | TGTTTCCAATCGACTCTGGC | 20 |
| ABCR.EXON5:R | TTCTTGCCTTTCTCAGGCTGG | 21 |
| ABCR.EXON6:F | GTATTCCCAGGTTCTGTGG | 22 |
| ABCR.EXON6:R | TACCCCAGGAATCACCTTG | 23 |
| ABCR.EXON7:F | AGCATATAGGAGATCAGACTG | 24 |
| ABCR.EXON7:R | TGACATAAGTGGGGTAAATGG | 25 |
| ABCR.EXON8:F | GAGCATTGGCCTCACAGCAG | 26 |
| ABCR.EXON8:R | CCCCAGGTTTGTTTCACC | 27 |
| ABCR.EXON9:F | AGACATGTGATGTGGATACAC | 28 |
| ABCR.EXON9:R | GTGGGAGGTCCAGGGTACAC | 29 |
| ABCR.EXON10:F | AGGGGCAGAAAAGACACAC | 30 |
| ABCR.EXON10:R | TAGCGATTAACTCTTTCCTGG | 31 |
| ABCR.EXON11:F | CTCTTCAGGGAGCCTTAGC | 32 |
| ABCR.EXON11:R | TTCAAGACCACTTGACTTGC | 33 |
| ABCR.EXON12:F | TGGGACAGCAGCCTTATC | 34 |
| ABCR.EXON12:R | CCAAATGTAATTTCCCACTGAC | 35 |
| ABCR.EXON13:F | AATGAGTTCCGAGTCACCCTG | 36 |
| ABCR.EXON13:R | CCCATTCGCGTGTCATGG | 37 |
| ABCR.EXON14:F | TCCATCTGGGCTTTGTTCTC | 38 |
| ABCR.EXON14:R | AATCCAGGCACATGAACAGG | 39 |
| ABCR.EXON15:F | AGGCTGGTGGGAGAGAGC | 40 |
| ABCR.EXON15:R | AGTGGACCCCCTCAGAGG | 41 |
| ABCR.EXON16:F | CTGTTGCATTGGATAAAAGGC | 42 |
| ABCR.EXON16:R | GATGAATGGAGAGGGCTGG | 43 |
| ABCR.EXON17:F | CTGCGGTAAGGTAGGATAGGG | 44 |
| ABCR.EXON17:R | CACACCGTTTACATAGAGGGC | 45 |
| ABCR.EXON18:F | CCTCTCCCCTCCTTTCCTG | 46 |
| ABCR.EXON18:R | GTCAGTTTCCGTAGGCTTC | 47 |
| ABCR.EXON19:F | TGGGGCCATGTAATTAGGC | 48 |
| ABCR.EXON19:R | TGGGAAAGAGTAGACAGCCG | 49 |
| ABCR.EXON20:F | ACTGAACCTGGTGTGGGG | 50 |
| ABCR.EXON20:R | TATCTCTGCCTGTGCCCAG | 51 |
| ABCR.EXON21:F | GTAAGATCAGCTGCTGGAAG | 52 |
| ABCR.EXON21:R | GAAGCTCTCCTGCACCAAGC | 53 |
| ABCR.EXON22:F | AGGTACCCCCACAATGCC | 54 |
| ABCR.EXON22:R | TCATTGTGGTTCCAGTACTCAG | 55 |
| ABCR.EXON23:F | TTTTTGCAACTATATAGCCAGG | 56 |
| ABCR.EXON23:R | AGCCTGTGTGAGTAGCCATG | 57 |
| ABCR.EXON24:F | GCATCAGGGCGAGGCTGTC | 58 |
| ABCR.EXON24:R | CCCAGCAATACTGGGAGATG | 59 |
| ABCR.EXON25:F | GGTAACCTCACAGTCTTCC | 60 |
| ABCR.EXON25:R | GGGAACGATGGCTTTTTGC | 61 |
| ABCR.EXON26:F | TCCCATTATGAAGCAATACC | 62 |
| ABCR.EXON26:R | CCTTAGACTTTCGAGATGG | 63 |
| ABCR.EXON27:F | GCTACCAGCCTGGTATTTCATTG | 64 |
| ABCR.EXON27:R | GTTATAACCCATGCCTGAAG | 65 |
| ABCR.EXON28:F | TGCACGCGCACGTGTGAC | 66 |
| ABCR.EXON28:R | TGAAGGTCCCAGTGAAGTGGG | 67 |
| ABCR.EXON29:F | CAGCAGCTATCCAGTAAAGG | 68 |
| ABCR.EXON29:R | AACGCCTGCCATCTTGAAC | 69 |
| ABCR.EXON30:F | GTTGGGCACAATTCTTATGC | 70 |
| ABCR.EXON30:R | GTTGTTTGGAGGTCAGGTAC | 71 |
| ABCR.EXON31:F | AACATCACCCAGCTGTTCCAG | 72 |
| ABCR.EXON31:R | ACTCAGGAGATACCAGGGAC | 73 |
| ABCR.EXON32:F | GGAAGACAACAAGCAGTTTCAC | 74 |
| ABCR.EXON32:R | ATCTACTGCCCTGATCATAC | 75 |
| ABCR.EXON33:F | AAGACTGAGACTTCAGTCTTC | 76 |
| ABCR.EXON33:R | GGTGTGCCTTTTAAAAGTGTGC | 77 |
| ABCR.EXON34:F | TTCATGTTTCCCTACAAAACCC | 78 |
| ABCR.EXON34:R | CATGAGAGTTTCTCATTCATGG | 79 |
| ABCR.EXON35:F | TGTTTACATGGTTTTTAGGGCC | 80 |
| ABCR.EXON35:R | TTCAGCAGGAGGAGGGATG | 81 |
| ABCR.EXON36:F | CCTTTCCTTCACTGATTTCTGC | 82 |
| ABCR.EXON36:R | AATCAGCACTTCGCGGTG | 83 |
| ABCR.EXON37:F | TGTAAGGCCTTCCCAAAGC | 84 |
| ABCR.EXON37:R | TGGTCCTTCAGCGCACACAC | 85 |
| ABCR.EXON38:F | CATTTTGCAGAGCTGGCAGC | 86 |
| ABCR.EXON38:R | CTTCTGTCAGGAGATGATCC | 87 |
| ABCR.EXON39:F | GGAGTGCATTATATCCAGACG | 88 |
| ABCR.EXON39:R | CCTGGCTCTGCTTGACCAAC | 89 |
| ABCR.EXON40:F | TGCTGTCCTGTGAGAGCATC | 90 |
| ABCR.EXON40:R | GTAACCCTCCCAGCTTTGG | 91 |
| ABCR.EXON41:F | CAGTTCCCACATAAGGCCTG | 92 |
| ABCR.EXON41:R | CAGTTCTGGATGCCCTGAG | 93 |
| ABCR.EXON42:F | GAAGAGAGGTCCCATGGAAAGG | 94 |
| ABCR.EXON42:R | GCTTGCATAAGCATATCAATTG | 95 |
| ABCR.EXON43:F | CTCCTAAACCATCCTTTGCTC | 96 |
| ABCR.EXON43:R | AGGCAGGCACAAGAGCTG | 97 |
| ABCR.EXON44:F | CTTACCCTGGGGCCTGAC | 98 |
| ABCR.EXON44:R | CTCAGAGCCACCCTACTATAG | 99 |
| ABCR.EXON45:F | GAAGCTTCTCCAGCCCTAGC | 100 |
| ABCR.EXON45:R | TGCACTCTCATGAAACAGGC | 101 |
| ABCR.EXON46:F | GTTTGGGGTGTTTGCTTGTC | 102 |
| ABCR.EXON46:R | ACCTCTTTCCCCAACCCAGAG | 103 |
| ABCR.EXON47:F | GAAGCAGTAATCAGAAGGGC | 104 |
| ABCR.EXON47:R | GCCTCACATTCTTCCATGCTG | 105 |
| ABCR.EXON48:F | TCACATCCCACAGGCAAGAG | 106 |
| ABCR.EXON48:R | TTCCAAGTGTCAATGGAGAAC | 107 |
| ABCR.EXON49:F | ATTACCTTAGGCCCAACCAC | 108 |
| ABCR.EXON49:R | ACACTGGGTGTTCTGGACC | 109 |
| ABCR.EXON50:F | GTGTAGGGTGGTGTTTTCC | 110 |
| ABCR.EXON50:R | AAGCCCAGTGAACCAGCTGG | 111 |
| ABCR.EXON51:F | TCAGCTGAGTGCCCTTCAG | 112 |
| ABCR.EXON51:R | AGGTGAGCAAGTCAGTTTCGG | 113 |

In Table 1, "F" indicates forward, i.e., 5' to 3', "R" indicates reverse, i.e., 3' to 5'. PCR conditions were 95° C. for 8 minutes; 5 cycles at 62° C. for 20 seconds, 70° C. for 30 seconds; 35 cycles at 60° C. for 20 seconds, 72° C. for 30 seconds; 72° C. for 5 minutes (except that $^a$ was performed at 90° C. for 5 minutes); 5 cycles at 94° C. for 40 seconds; 60° C. for 30 seconds; 72° C. for 20 seconds; 35 cycles at 94° C. for 40 seconds; 56° C. for 30 seconds; 72° C. for 20 seconds, and 72° C. for 5 minutes.

Amplification of exons was performed with AmpliTaq Gold polymerase in a 25 μl volume in 1X PCR buffer supplied by the manufacturer (Perkin Elmer, Foster City, Calif.). Samples were heated to 95° C. for 10 minutes and amplified for 35–40 cycles at 96° C. for 20 seconds; 58° C. for 30 seconds; and 72° C. for 30 seconds. PCR products were analyzed on 1–1.5% agarose gels and in some cases digested with an appropriate restriction enzymes to verify their sequence. Primer sequences and specific reaction conditions are set forth in Table 1. The sequence of the ABCR cDNA has been deposited with GenBank under accession #U88667.

Homology to ABC Superfamily Members

Figure 4B:
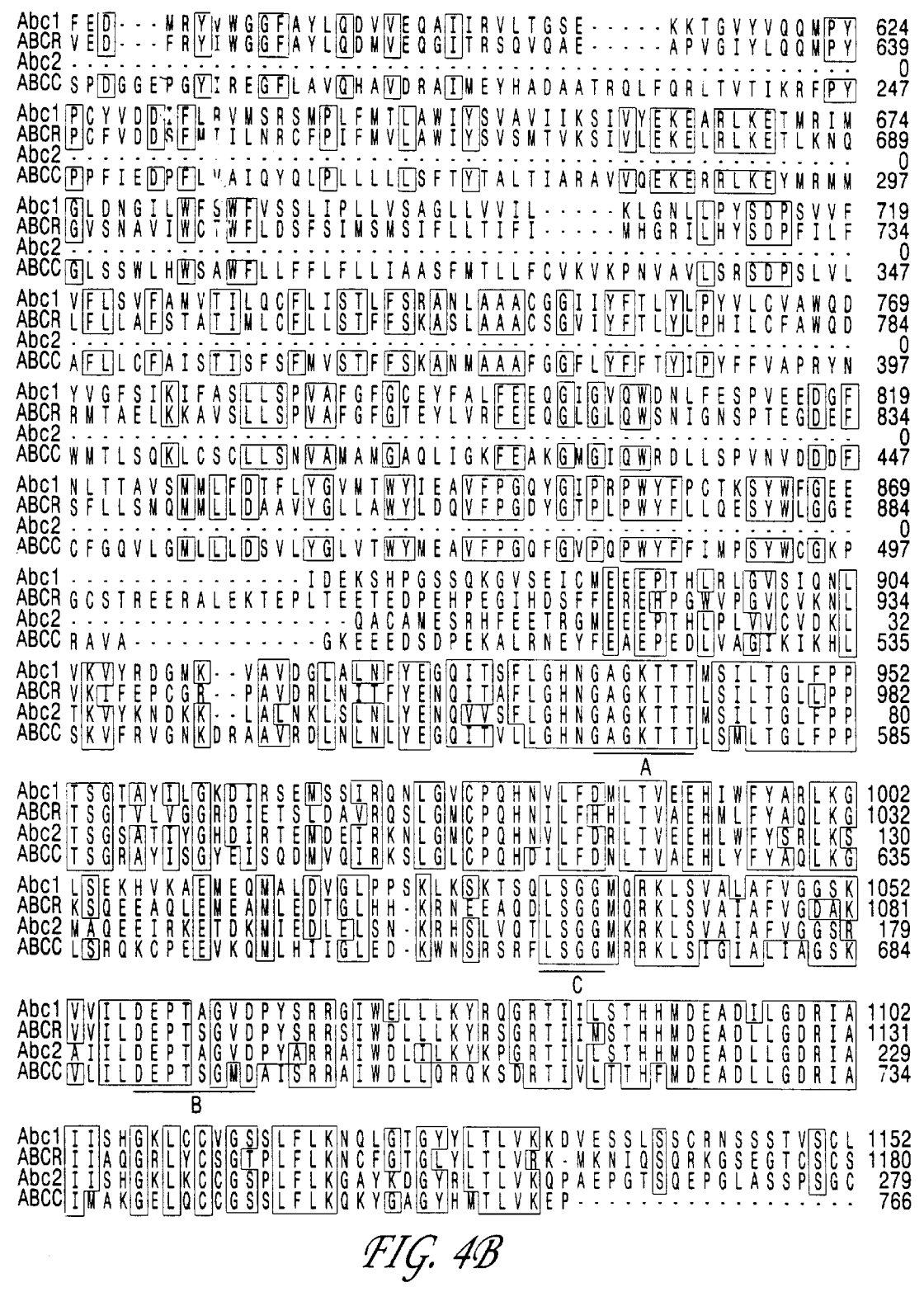

A BLAST search revealed that ABCR is most closely related to the previously characterized mouse Abc1 and Abc2 genes (Luciani et al., 1994) and to another human gene (ABCC) which maps to chromosome 16p13.3 (Klugbauer and Hofmann, 1996). These genes, together with ABCR and a gene from C. elegans (GenBank #Z29117), form a subfamily of genes specific to multicellular organisms and not represented in yeast (Michaelis and Berkower, 1995; Allikmets et al., 1996). Alignment of the cDNA sequence of ABCR with the Abc1, ABc2, and ABCC genes revealed, as expected, the highest degree of homology within the ATP-binding cassettes. The predicted amino acid identity of the ABCR gene to mouse Abc1 was 70% within the ATP-bending domains; even within hydrophobic membrane-spanning segments, homology ranged between 55 and 85% (FIG. 4). The putative ABCR initiator methionine shown in FIGS. 3 and 4 corresponds to a methionine codon at the 5' end of Abc1 (Luciani et al., 1994).

ABCR shows the composition of a typical full-length ABC transporter that consists of two transmembrane domains (TM), each with six membrane spanning hydrophobic segments, as predicted by a hydropathy plot (data not shown), and two highly conserved ATP-binding domains (FIGS. 3 and 4). In addition, the HH1 hydrophobic domain, located between the first ATP and second TM domain and specific to this subfamily (Luciani et al., 1994), showed a predicted 57% amino acid identity (24 of 42 amino acids) with the mouse Abc1 gene.

Figure 5:
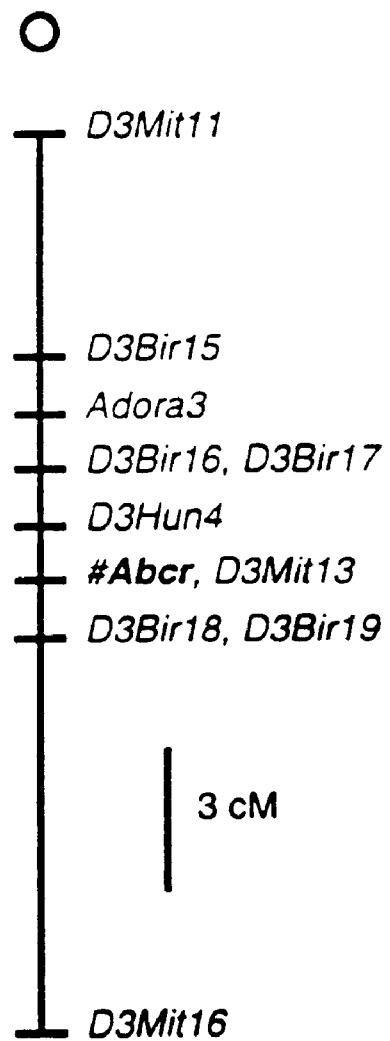
FIG. 5 exhibits the location of Abcr from a Jackson BSS Backcross showing a portion of mouse chromosome 3. The map is depicted with the centromere toward the top. A 3 cM scale bar is also shown. Loci mapping to the same position are listed in alphabetical order.

To characterize the mouse ortholog of ABCR, cDNA clones from a developing mouse eye library were isolated. A partial sequence of the mouse cDNA was utilized to design PCR primers to map the mouse Abcr gene in an interspecific backcross mapping panel (Jackson BSS). The allele pattern of Abcr was compared to 2450 other loci mapped previously in the Jackson BSS cross; linkage was found to the distal end of chromosome 3 (FIG. 5). No recombinants were observed between Abcr and D13Mit13. This region of the mouse genome is syntenic with human chromosome 1p13-p21. Thus far, no eye disease phenotype has been mapped to this region of mouse chromosome 3.

Compound Heterozygous and Homozygous Mutations in STGD Patients

One hundred forty-five North American and three Saudi Arabian families with STGD/FFM were examined. Among these, at least four were consanguineous families in which the parents were first cousins. Entry criteria for the characterization of the clinical and angiographic diagnosis of Stargardt disease, ascertainment of the families, and methodology for their collection, including the consanguineous families from Saudi Arabia, were as provided in Anderson et al., 1995; and Anderson, 1996.

Mutational analysis of the ABCR gene was pursued in the above identified one hundred forty-eight STGD families previously ascertained by strict definitional criteria and shown to be linked to chromosome 1 p (Anderson et al., 1995; Anderson, 1996). To date, all 51 exons have been used for mutation analysis.

Mutations were detected by a combined SSCP (Orita et al., 1989) and heteroduplex analysis (White et al., 1992) under optimized conditions (Glavač and Dean, 1993). Genomic DNA samples (50 ng) were amplified with AmpliTaq Gold polymerase in 1X PCR buffer supplied by the manufacturer (Perkin Elmer, Foster City, Calif.) containing [α-$^{32}$P] dCTP. Samples were heated to 95° C. for 10 minutes and amplified for 35–40 cycles at 96° C. for 20 seconds; 58° C. for 30 seconds; and 72° C. for 30 seconds. Products were diluted in 1:3 stop solution, denatured at 95° C. for 5 minutes, chilled in ice for 5 minutes, and loaded on gels. Gel formulations include 6% acrylamide:Bis (2.6% cross-linking), 10% glycerol at room temperature, 12W; and 10% acrylamide:Bis (1.5% cross-linking), at 4° C., 70 W. Gels were run for 2–16 hours (3000 Vh/100 bp), dried, and exposed to X-ray film for 2–12 hours. Some exons were analyzed by SSCP with MDE acrylamide (FMC Bioproducts, Rockland, Me.) with and without 10% glycerol for 18 hours, 4 watts at room temperature with α-P$^{32}$-dCTP labeled DNA. Heteroduplexes were identified from the double-stranded DNA at the bottom of the gels, and SSCPs were identified from the single-stranded region. Samples showing variation were compared with other family members to assess segregation of the alleles and with at least 40 unrelated control samples, from either Caucasian or Saudi Arabian populations, to distinguish mutations from polymorphisms unrelated to STGD. PCR products with SSCP or heteroduplex variants were obtained in a 25 μl volume, separated on a 1% agarose gel, and isolated by a DNA purification kit (PGC Scientific, Frederick, Md.). Sequencing was performed on an ABI sequencer with both dye primer and dye terminator chemistry.

Some mutations were identified with a heteroduplex analysis protocol (Roa et al., 1993). Equimolar amounts of control and patient PCR products were mixed in 0.2 ml tubes. Two volumes of PCR products from a normal individual served as a negative control, and MPZ exon 3 from patient BAB731 as a positive control (Roa et al., 1996). Samples were denatured at 95° C. for 2 minutes and cooled to 35° C. at a rate of 1° C./minute. Samples were loaded onto 1.0 mm thick, 40 cm MDE gels (FMC Bioproducts, Rockland, Me.,), electrophoresed at 600–800 V for 15–20 hours, and visualized with ethidium bromide. Samples showing a variant band were reamplified with biotinylated forward and reverse primers and immobilized on streptavidin-conjugated beads (Warner et al., 1996). The resulting single strands were sequenced by the dideoxy-sequencing method with Sequenase 2.0 (Amersham, Arlington Heights, Ill.).

A total of seventy five mutations were identified, the majority representing missense mutations in conserved amino acid positions. However, several insertions and deletions representing frameshifts were also found (Table 2). Two missense alterations (D847H, R943Q) were found in at least one control individual, suggesting that they are neutral polymorphisms. The remaining mutations were found in patients having macular degeneration and were not found in at least 220 unrelated normal controls 9440 chromosomes), consistent with the interpretation that these alterations represents disease-causing mutations, not polymorphisms. One of the mutations, 5892+1 G→T, occurs in family AR144 in which one of the affected children is recombinant for the flanking marker D1S236 (Anderson et al., 1995). This mutation, however, is present in the father as well as in both affected children. Therefore, the ABCR gene is non-recombinant with respect to the Stargardt disease locus.

Figure 6:
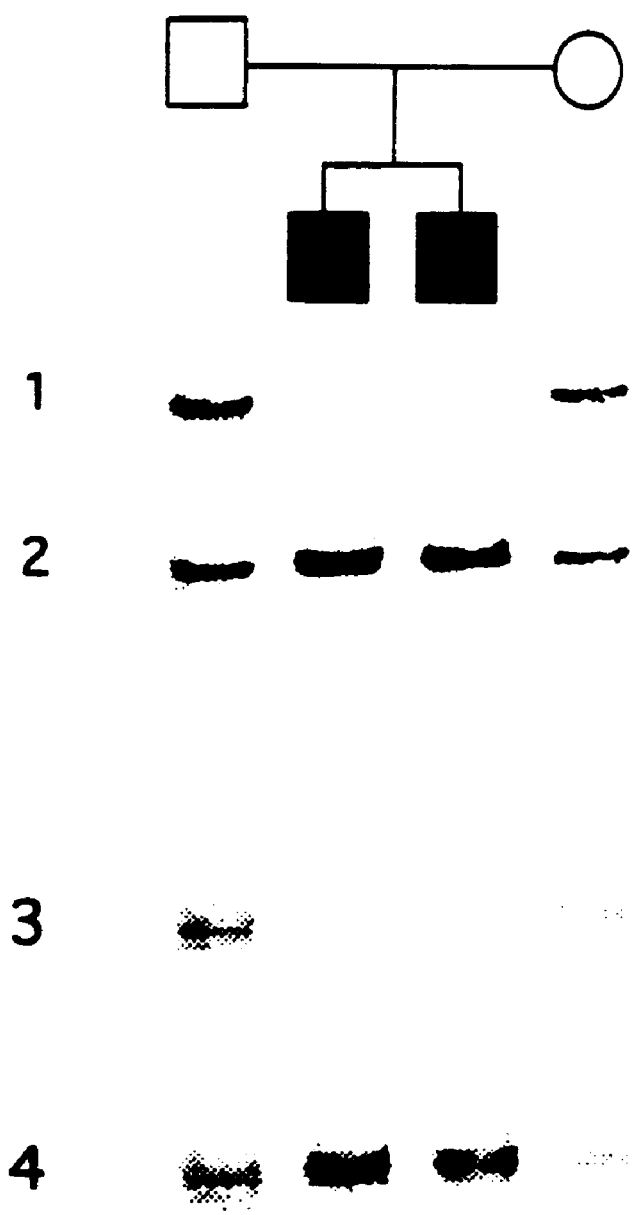
FIG. 6 shows the segregation of SSCP variants in exon 49 of the ABCR gene in kindred AR293. Sequence analysis of SSCP bands revealed the existence of wild-type sequence (bands 1 and 3) and mutant sequence (bands 2 and 4). DNA sequencing revealed a 15 base pair deletion, while the affected children (lanes 2 and 3) are homozygous. Haplotype analysis demonstrated homozygosity at the STGD locus in the two affected individuals.
Figure 8:
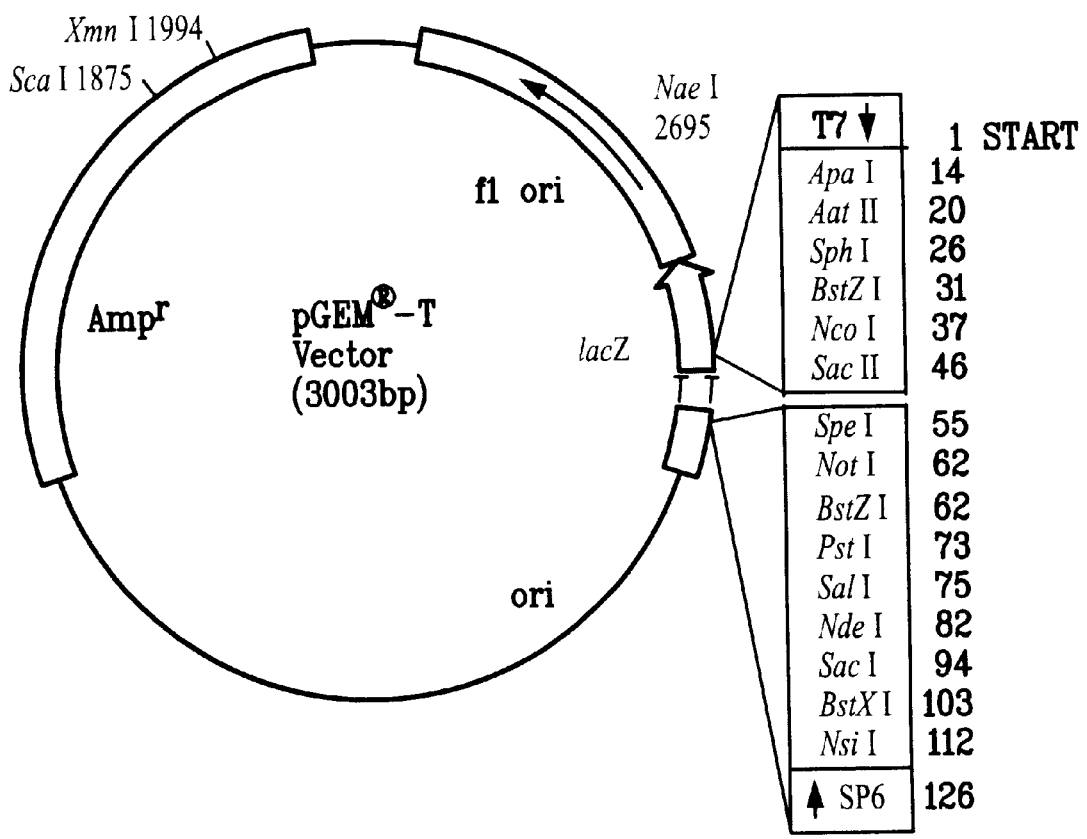
FIG. 8 provides a pGEM®-T Vector map.

The mutations are scattered throughout the coding sequence of the ABCR gene (see Table 2 and FIG. 3), although clustering within the conserved regions of the ATP-binding domains is noticeable. Homozygous mutations were detected in three likely consanguineous families, two Saudi Arabian and one North American (Anderson et al., 1995), in each of which only the affected individuals inherited the identical disease allele (Table 2; FIG. 6). Forty two compound heterozygous families were identified in which the two disease alleles were transmitted from different parents to only the affected offspring (Table 2).

TABLE 2

| Mutations in the ABCR gene in STGD Families | | | |
| --- | --- | --- | --- |
| Nucleotide | Amino Acid | # Families | Exon |
| 0223T->G | C75G | 1 | 3 |
| 0634C->T | R212C | 1 | 6 |
| 0664del13 | fs | 1 | 6 |
| 0746A->G | D249G | 1 | 6 |
| 1018T->G | Y340D | 2 | 8 |
| 1411G->A | E471K | 1 | 11 |
| 1569T->G | D523E | 1 | 12 |
| 1715G->A | R572Q | 2 | 12 |
| 1715G->C | R572P | 1 | 12 |
| 1804C->T | R602W | 1 | 13 |
| 1822T->A | F608I | 1 | 13 |

TABLE 2-continued

Mutations in the ABCR gene in STGD Families

| Nucleotide | Amino Acid | # Families | Exon |
|---|---|---|---|
| 1917C->A | Y639X | 1 | 13 |
| 2453G->A | G818E | 1 | 16 |
| 2461T->A | W821R | 1 | 16 |
| 2536G->C | D846H | 1 | 16 |
| 2588G->C | G863A | 11 | 17 |
| 2791G->A | V931M | 1 | 19 |
| 2827C->T | R943W | 1 | 19 |
| 2884delC | fs | 1 | 19 |
| 2894A->G | N965S | 3 | 19 |
| 3083C->T | A1028V | 14 | 21 |
| 3211delGT | fs | 1 | 22 |
| 3212C->T | S1071L | 1 | 22 |
| 3215T->C | V1072A | 1 | 22 |
| 3259G->A | E1087K | 1 | 22 |
| 3322C->T | R1108C | 6 | 22 |
| 3364G->A | E1122K | 1 | 23 |
| 3385G->T | R1129C | 1 | 23 |
| 3386G->T | R1129L | 1 | 23 |
| 3602T->G | L1201R | 1 | 24 |
| 3610G->A | D1204N | 1 | 25 |
| 4139C->T | P1380L | 2 | 28 |
| 4195G->A | E1399K | 1 | 28 |
| 4222T->C | W1408R | 3 | 28 |
| 4232insTATG | fs | 1 | 28 |
| 4253+5G->T | splice | 1 | 28 |
| 4297G->A | V1433I | 1 | 29 |
| 4316G->A | G1439D | 1 | 29 |
| 4319T->C | F1440S | 1 | 29 |
| 4346G->A | W1449X | 1 | 29 |
| 4462T->C | C1488R | 1 | 30 |
| 4469G->A | C1490Y | 1 | 31 |
| 4577C->T | T1526M | 6 | 32 |
| 4594G->A | D1532N | 2 | 32 |
| 4947delC | fs | 1 | 36 |
| 5041del15 | VVAIC1681del | 1 | 37 |
| 5196+2T->C | splice | 1 | 37 |
| 5281del9 | PAL1761del | 1 | 38 |
| 5459G->C | R1820P | 1 | 39 |
| 5512C->T | H1838Y | 1 | 40 |
| 5527C->T | R1843W | 1 | 40 |
| 5585+1G->A | splice | 1 | 41 |
| 5657G->A | G1886E | 1 | 41 |
| 5693G->A | R1898H | 4 | 41 |
| 5714+5G->A | splice | 8 | 41 |
| 5882G->A | G1961E | 16 | 43 |
| 5898+1G->A | splice | 3 | 43 |
| 5908C->T | L1970F | 1 | 44 |
| 5929G->A | G1977S | 1 | 44 |
| 6005+1G->T | splice | 1 | 44 |
| 6079C->T | L2027F | 11 | 45 |
| 6088C->T | R2030X | 1 | 45 |
| 6089G->A | R2030Q | 1 | 45 |
| 6112C->T | R2038W | 1 | 45 |
| 6148G->C | V2050L | 2 | 46 |
| 6166A->T | K2056X | 1 | 46 |
| 6229C->T | R2077W | 1 | 46 |
| 6286G->A | E2096K | 1 | 47 |
| 6316C->T | R2106C | 1 | 47 |
| 6391G->A | E2131K | 1 | 48 |
| 6415C->T | R2139W | 1 | 48 |
| 6445C->T | R2149X | 1 | 48 |
| 6543del36 | I181del12 | 1 | 49 |
| 6709delG | fs | 1 | 49 |

Mutations are named according to standard nomenclature. The column headed "Exon" denotes which of the 51 exons of ABCR contain the mutation. The column headed "# Families" denotes the number of Stargardt families which displayed the mutation. The column headed "Nucleotide" gives the base number starting from the A in the initiator ATG, followed by the wild type sequence and an arrow indicating the base it is changed to: del indicates a deletion of selected bases at the given position in the ABCR gene; ins indicates an insertion of selected bases at the given position; splice donor site mutations are indicated by the number of the last base of the given exon, followed by a plus sign and the number of bases into the intron where the mutation occurs. The column headed "Amino Acid" denotes the amino acid change a given mutation causes; fs indicates a frameshift mutation leading to a truncated protein; splice indicates a splice donor site mutation; del indicates an in-frame deletion of the given amino acids.

Mutations are named according to standard nomenclature. Exon numbering according to the nucleotide position starting from the A in the initiator ATG.

In Situ Hybridization

STGD is characterized histologically by a massive accumulation of a lipofuscin-like substance in the retinal pigment epithelium (RPE). This characteristic has led to the suggestion that STGD represents an RPE storage disorder (Blacharski et al., 1988). It was therefore of interest that ABCR transcripts were found to be abundant in the retina. To identify the site(s) of ABCR gene expression at higher resolution and to determine whether the gene is also expressed in the RPE, the distribution of ABCR transcripts was visualized by in situ hybridization to mouse, rat, bovine, and macaque ocular tissues.

In situ hybridization with digoxigenin-labeled riboprobes was performed as described by Schaeren-Wiemers and Gerfin-Moser, 1993. For mouse and rat, unfixed whole eyes were frozen and sectioned; macaque retinas were obtained following cardiac perfusion with paraformaldehyde as described (Zhou et al., 1996). An extra incubation of 30 min in 1% Triton X-100, 1X PBS was applied to the fixed monkey retina sections immediately after the acetylation step. The templates for probe synthesis were: (1) a 1.6 kb fragment encompassing the 3' end of the mouse Abcr coding region, (2) a full length cDNA clone encoding the mouse blue cone pigment (Chiu et al., 1994), and (3) a macaque rhodopsin coding region segment encoding residues 133 to 254 (Nickells, R. W., Burgoyne, C. F., Quigley, H. A., and Zack, D. J. (1995)).

This analysis showed that ABCR transcripts are present exclusively within photoreceptor cells (FIG. 7). ABCR transcripts are localized principally to the rod inner segments, a distribution that closely matches that of rhodopsin gene transcripts. Interestingly, ABCR hybridization was not observed at detectable levels in cone photoreceptors, as judged by comparisons with the hybridization patterns obtained with a blue cone pigment probe (compare FIG. 7A and FIG. 7D, FIG. 7E with FIG. 7F and FIG. 7G with FIG. 7H). Because melanin granules might obscure a weak hybridization signal in the RPE of a pigmented animal, the distribution of ABCR transcripts was also examined in both albino rats and albino mice. In these experiments, the ABCR hybridization signal was seen in the photoreceptor inner segments and was unequivocally absent from the RPE (FIG. 7E). Given that ABCR transcripts in each of these mammals, including a primate, are photoreceptor-specific, it is highly likely that the distribution of ABCR transcripts conforms to this pattern as well in the human retina.

The disclosures of each patent, patent application and publication cited or described in this document are hereby incorporated herein by reference, in their entirety.

Various modifications of the invention in addition to those shown and described herein will be apparent to those skilled in the art from the foregoing description. Such modifications are also intended to fall within the scope of the appended claims.

References

Allikmets, R., Singh, N., Sun, H., Shroyer, N. F., Hutchinson, A., Chidambaram, A., Gerrard, B., Baird, L., Stauffer, D., Peiffer, A., Rattner, A., Smallwood, P., Li, Y., Anderson, K. L., Lewis, R. A., Nathans, J., Leppert, M., Dean, M., Lupski, J. R., (1997) A photoreceptor cell-specific ATP-binding transporter gene (ABCR) is mutated in recessive Stargardt macular dystrophy. Nature Genetics. 15(3):236–46.

Allikmets, R., Shroyer, N. F., Singh, N., Seddon, J. M., Lewis, R. A., Bernsteinm P. S., Peiffer, A., Zabriskie, N. A., Li, Y., Hutchinson, A., Dean, M., Lupski, J. R., Leppert, M., (1997) Mutation of the Stargardt disease gene (ABCR) in age-related macular degeneration. Science. 277(5333):1805–7.

Allikmets, R., Gerrard B., Hutchinson, A., and Dean, M. (1996). Characterization of the human ABC superfamily: Isolation and mapping of 21 new genes using the Expressed Sequence Tag database. Hum. Mol. Genet. 5, 1649–1655.

Allikmets, R., Gerrard, B., Glavač, D., Ravnik-Glavač, M., Jenkins, N. A., Gilbert, D. J., Copeland, N. G., Modi, W., and Dean, M. (1995). Characterization and mapping of three new mammalian ATP-binding transporter genes from an EST database. Mam. Genome 6, 114–117.

Allikmets, R., Gerrard, B., Court, D. and Dean, M. (1993). Cloning and organization of the abc and mdl genes of *Escherichia coli*: relationship to eukaryotic multidrug resistance. Gene 136, 231–236.

Altschul, S. F., Gish, W., Miller, W., Myers, E. W., and Lipman, D. J. (1990). Basic local alignment search tool. J. Mol. Biol. 215, 403–410.

Anderson, K. L., Baird, L., Lewis, R. A., Chinault, A. C., Otterud, B., Leppert, M., and Lupski, J. R. (1995). A YAC contig encompassing the recessive Stargardt disease gene (STGD) on chromosome 1p. Am. J. Hum. Genet. 57, 1351–1363.

Anderson, K. L. (Jul. 30, 1996) Towards the Isolation of Genes for Recessively Inherited Ocular Disorders; Bardet-Biedl Syndrome, Leber Congenital Amaurosis, Primary Congenital Glaucoma, and Stargardt Disease. Ph.D. Thesis. Baylor College of Medicine.

Anderson, R. E. and Maude, M. B. (1971). Lipids of ocular tissues: the effects of essential fatty acid deficiency on the phospholipids of the photoreceptor membranes of rat retina. Arch. Biochem. Biophys. 151, 270–276.

Azarian, S. M., Travis, G. H., (1997) The photoreceptor rim protein is an ABC transporter encoded by the gene for recessive Stargardt's disease (ABCR). FEBS Letters. 409 (2):247–52.

Bellanne-Chantelot, C., et al. (1992). Mapping the Whole Human Genome by Fingerprinting Yeast Artificial Chromosomes. Cell 70, 1059–1068.

Birnbach, C. D., Järveläinen, M., Possin, D. E., and Milam, A. H. (1994). Histopathology and immunocytochemistry of the neurosensory retina in fundus flavimaculatus. Ophthalmology 101, 1211–1219.

Blacharski, D. A. (1988). Fundus flavimaculatus. In Retinal Dystrophies and Degenerations, D. A. Newsome, ed. (New York: Raven Press), pp. 135–159.

Boguski, M. S., Lowe, T. M., and Tolstoshev, C. M. (1993). dbEST-database for "expressed sequence tags". Nature Genet. 4, 332–333.

Chen, Z.-Y., Battinelli, E. M., Hendricks, R. W., Powell, F., Middleton-Price, H., Sims, K. B., Breakfield, X. O., and Craig, I. W. (1993). Norrie disease gene: characterization of deletions and possible function. Genomics 16, 533–535.

Childs, S., and Ling, V. (1994). The MDR superfamily of genes and its biological implications. In Important Advances in Oncology, V. T. DeVita, S. Hellman and S. A. Rosenberg, eds. (Philadelphia, Pa.: Lippincott Company), pp. 21–36.

Chiu, M. I., Zack, D. J., Wang, Y., and Nathans, J. (1994). Murine and bovine blue cone pigment genes: cloning and characterization of two new members of the S family of visual pigments. Genomics 21, 440–443.

Chomczynski, P. and Sacchi, N. (1987). Single-step method of RNA isolation by acid guanidinium thiocyanate-phenol-chloroform extraction. Anal. Biochem. 162, 156–159.

Daemen, F. J. M. (1973). Vertebrate rod outer segment membranes. Biochem. Biophys. Acta 300, 255–288.

de la Salle, H., Hanau, D., Fricker, D., Urlacher, A., Kelly, A., Salamero, J., Powis, S. H., Donato, L., Bausinger, H., Laforet, M., Jeras, M., Spehner, D., Bieber, T., Falkenrodt, A., Cazenave, J.-P., Trowsdale, J., and Tongio, M.-M. (1994). Homozygous human TAP peptide transporter mutation in HLA class I deficiency. Science 265, 237–241.

Dean, M., and Allikmets, R. (1995). Evolution of ATP-binding cassette transporter genes. Curr. Opin. Genet. Dev. 5, 779–785.

Dean, M., Allikmets, R., Gerrard, B., Stewart, C., Kistler, A., Shafer, B., Michaelis, S., and Strathern, J. (1994). Mapping and sequencing of two yeast genes belonging to the ATP-binding cassette superfamily. Yeast 10, 377–383.

Devereaux, J., Haeberli, P., and Smithies, O. (1984). A comprehensive set of sequence analysis programs for the VAX. Nucleic Acids Res. 12, 387–395.

Dowling, J. E. (1960). Chemistry of visual adaptation in the rat. Nature 188, 114–118.

Dryja, T. P. and Li, T. (1995). Molecular genetics of retinitis pigmentosa. Hum. Mol. Genet. 4, 1739–1743.

Eagle, R. C. Jr., Lucier, A. C., Bernadino, V. B. Jr., and Yanoff, M. (1980). Retinal pigment epithelial abnormalities in Fundus Flavimaculatus: A light and electron microscopic study. Ophthalmology 87, 1189–1200.

Feeney, L. (1978). Lipofuscin and melanin of human retinal pigment epithelium. Fluorescence, enzyme cytochemical, and ultrastructural studies Invest. Ophthalmol. Vis. Sci. 17, 583–600.

Feng, D.-F., and Doolittle, R. F. (1987). Progressive sequence alignment as a prerequisite to correct phyllogenetic trees. J. Mol. Evol. 25, 351–360.

Fishman, G. A. (1976). Fundus flavimaculatus: a clinical classification. Arch. Ophthalmol. 94, 2061–2067.

Fong, S.-L., Liou, G. I., Landers, R. A., Alvarez, R. A., and Bridges, C. D. (1984). Purification and characterization of a retinol-binding glycoprotein synthesized and secreted by bovine neural retina. J. Biol. Chem. 259, 6534–6542.

Franceschetti, A. (1964). Über tapeto-retinale Degenerationen im Kindesalter. In H. von Sautter, ed. Entwicklung und Fortschritt in der Augenheilkunde. (Stuttgart: Ferdinand Enke) pp. 107–120.

Gass, J. D. M. (1987). Stargardt's disease (Fundus Flavimaculatus) in Stereoscopic Atlas of Macular Diseases: Diagnosis and Treatment, Volume 1, 3rd edition. pages 256–261. The C. V. Mosby Company, St. Louis, Mo.

Gerber, S., Rozet, J.-M., Bonneau, D., Souied, E., Camuzat, A., Dufier, J.-L., Amalric, P., Weissenbach, J., Munnich, A., and Kaplan, J. (1995). A gene for late-onset fundus flavimaculatus with macular dystrophy maps to chromosome 1p13. Am . J. Hum. Genet. 56, 396–399.

Glavač, D., and Dean, M. (1993). Optimization of the single-strand conformation polymorphism (SSCP) technique for detection of point mutations. Hum. Mutat. 2, 404–414.

Hayes, K. C. (1974). Retinal degeneration in monkeys induced by deficiencies of vitamin E or A. Invest, Ophthalmology 13, 499–510.

Hettema, E. H., van Roermund, C. W. T., Distel, B., van den Berg, M., Vilela, C., Rodrigues-Pousada, C., Wanders, R. J. A., and Tabak, H. F. (1996). The ABC transporter proteins Pat1 and Pat2 are required for import of long-chain fatty acids into peroxisomes of Saccharomyces cervisiae. EMBO J. 15, 3813–3822.

Hoyng, C. B., Poppelaars, F., van de Pol, T. J. R., Kremer, H., Pinckers, A. J. L. G., Deutman, A. F., and Cremers, F. P. M. (1996). Genetic fine mapping of the gene for recessive Stargardt disease. Hum. Genet. 98, 500–504.

Hyde, S. C., Emsley, P., Hartshorn, M. J., Mimmack, M. M., Gileadi, U., Pearce, S. R., Gallagher, M. P., Gill, D. R., Hubbard, R. E., and Higgins, C. F. (1990). Structural model of ATP-binding proteins associated with cystic fibrosis, multidrug resistance and bacterial transport. Nature 346, 362–365.

Klein, B. A. and Krill, A. E. (1967). Fundus Flavimaculatus: clinical, functional, and histopathologic observations. Am. J. Ophthalmol. 64, 3–23.

Klugbauer, N., and Hofmann, F. (1996). Primary structure of a novel ABC transporter with a chromosomal localization on the band encoding the multidrug resistance-associated protein. FEBS Lett. 391, 61–65.

Kuwano, Y., Nakanishi, O., Nabeshima, Y.-I., Tanaka, T., and Ogata, K. (1985). Molecular cloning and nucleotide sequence of DNA complementary to rat ribosomal protein S26 messenger RNA. J. Biochem. (Tokyo) 97:832–992.

Lennon, G., Auffray, C., Polymeropoulos, M. and Soares, M. B. (1996). The I.M.A.G.E. consortium: An integrated molecular analysis of genomes and their expression. Genomics 33, 151–152.

Lincoln, A. L., Daly, M., and Lander, E. (1991). PRIMER: a computer program for automatically selecting PCR primers. Whitehead Institute Technical Report.

Lopez, P. F., Maumenee, I. H., de la Cruz, Z., Green, W. R. (1990). Autosomal-dominant fundus flavimaculatus: clinicopathologic correlation. Ophthalmology 97,798–809.

Luciani, M.-F., Denizot, F., Savary, S., Mattei, M. G., and Chimini, G. (1994). Cloning of two novel ABC transporters mapping on human chromosome 9. Genomics 21,150–159.

Luciani, M.-F., and Chimini, G. (1996). The ATP binding cassette transporter ABC1, is required for the engulfment of corpses generated by apoptotic cell death. EMBO J. 15, 226–235.

McDonnell, P. J., Kivlin, J. D., Maumenee, I. H., and Green, W. R. (1986). Fundus flavimaculatus without maculopathy: a clinicopathologic study. Ophthalmology 93, 116–119.

Meindl, A., Berger, W., Meitinger, T., van de Pol, D., Achatz, H., Dorner, C., Hasseman, M., Hellebrand, H., Gal, A., Cremers, F., and Ropers, H. H. (1992). Norrie disease is caused by mutations in an extracellular protein resembling c-terminal globular domain of mucins. Nat. Genet. 2, 139–143.

Meindl, A., Dry, K., Herrmann, K., Manson, F., Ciccodicola, A., Edgar, A., Carvalho, M. R. S., Achatz, H., Hellebrand, H., Lennon, A., Mibliaccio, C., Porter, K., Zrenner, E., Bird, A., Jay, M., Lorenz, B., Wittwer, B., D'urso, M., Meitinger, T., and Wright, A. (1996). A gene (RPGR) with homology to the RCC1 guanine nucleotide exchange factor is mutated in X-linked retinitis pigmentosa (RP3). Nat. Genet. 13, 35–42.

Michaelis, S., and Berkower, C. (1995). Sequence comparison of yeast ATP binding cassette (ABC) proteins. In Cold Spring Harbor Symposium on Quantitative Biology, vol.LX: Protein Kinesis—The Dynamics of Protein Trafficking and Stability. (Cold Spring Harbor Laboratory Press, Cold Spring Harbor).

Mosser, J., Douar, A.-M., Sarde, C.-O., Kioschis, P., Feil, R., Moser, H., Poustka, A.-M., Mandel, J.-L., and Aubourg, P. (1993). Putative X-linked adrenoleukodystrophy gene shares unexpected homology with ABC transporters. Nature 361, 726–730.

Nathans, J., Thomas, D., and Hogness, D. S. (1986). Molecular genetics of human color vision: the genes encoding blue, green, and red pigments. Science 232, 193–202.

Nickells, R. W., Burgoyne, C. F., Quigley, H. A., and Zack, D. J. (1995). Cloning and characterization of rodopsin cDNA from the old world monkey, Macaca fasciclaris. Investigative Ophthalmology and Visual Science 36:72–82.

Noble, K. G., and Carr, R. E. (1979). Stargardt's disease and fundus flavimaculatus. Arch. Ophthalmol. 97, 1281–1285.

Orita, M., Suzuki, Y., Sekiya, T., and Hayashi, K. (1989). Rapid and sensitive detection of point mutations and DNA polymorphisms using the polymerase chain reaction. Genomics 5, 874–879.

Rando, R. R. (1990). The chemistry of vitamin A and vision. Angew. Chem. Int. Ed. Engl. 29, 461–480.

Riordan, J. R., Rommens, J. M., Kerem, B.-S., Alon, N., Rozmahel, R., Grzelczak, Z., Zielenski, J., Lok, S., Plavsic, N., Chou, J.-L., Drumm, M. L., Ianuzzi, M. C., Collins, F. S., and Tsui, L.-C. (1989). Identification of the cystic fibrosis gene: cloning and characterization of complementary DNA. Science 245, 1066–1073.

Roa, B. B., Garcia, C. A., Suter, U., Kulpa, D. A., Wise, C. A., Mueller, J., Welcher, A. A., Snipes, G. J., Shooter, E. M., Patel, P. I., and Lupski, J. R. (1993). Charcot-Marie-Tooth disease type 1A, association with a spontaneous point mutation in the PMP22 gene. New Eng. J. Med. 329, 96–101.

Roa, B. B., Warner, L. E., Garcia, C. A., Russo, D., Lovelace, R., Chance P. F., and Lupski, J. R. (1996). Myelin protein zero (MPZ) gene mutations in nonduplication type 1 Charcot-Marie-Tooth disease. Hum. Mut. 7, 36–45.

Rowe, L. B., Nadeau, J. H., Turner, R., Frankel, W. N., Letts, V. A., Eppig, J., Ko, M. S. H., Thurston, S. J., and Birkenmeier, E. H. (1994). Maps from two interspecific backcross DNA panels available as a community genetic mapping resource. Mamm. Genome 5, 253–274.

Sambrook, J., Fritsch, E. F., and Maniatis, T. (1989). Molecular Cloning. (Cold Spring Harbor, N.Y.: Cold Spring Harbor Laboratory).

Schaeren-Wiemers, N., and Gerfin-Moser, A. (1993). A single protocol to detect transcripts of various types and expression levels in neural tissue and culture cells: in situ hybridization using digoxigenin-labeled cRNA probes. Histochemistry 100, 431–440.

Seabra, M. C., Brown, M. S., and Goldstein, J. L. (1993). Retinal degeneration in choroideremia: deficiency of Rab geranylgeranyl transferase. Science 259, 377–381.

Shani, N. and Valle, D. (1996). A *Saccharomyces cerevisiae* homolog of the human adrenoleukodystrophy transporter is a heterodimer of two half ATP-binding cassette transporters. Proc. Natl. Acad. Sci. USA 93, 11901–11906.

Shimozawa, N., Tsukamoto, T., Suzuki, Y., Orii, T., Shirayoshi, Y., Mori, T., and Fujiki, Y. (1992). A human gene responsible for Zellweger syndrome that affects peroxisome assembly. Science 255, 1132–1134.

Smit, J. J. M., Schinkel, A. H., Oude Elferink, R. P. J., Groen, A. K., Wagenaar, E., van Deemter, L., Mol, C. A. A. M., Ottenhoff, R., van der Lugt, N. M. T., van Roon, M. A., van der Valk, M. A., Offerhaus, G. J. A., Berns, A. J. M., and Borst, P. (1993). Homozygous disruption of the murine mdr2 P-glycoprotein gene leads to a complete absence of phospholipid from bile and to liver disease. Cell 75, 451–462.

Stargardt, K. (1909). Über familiäre, progressive Degeneration in der Maculagegend des Auges. Albrecht von Graefes Arch. Klin. Exp. Ophthalmol. 71, 534–550.

Steinmetz, R. L., Garner, A., Maguire, J. I., and Bird, A. C. (1991). Histopathology of incipient fundus flavimaculatus. Ophthalmology 98, 953–956.

Stone, E. M., Nichols, B. E., Kimura, A. E., Weingeist, T. A., Drack, A., and Sheffield, V. C. (1994). Clinical features of a Stargardt-like dominant progressive macular dystrophy with genetic linkage to chromosome 6q. Arch. Ophthalmol. 112, 765–772.

Sun, H., Nathans, J., (1997) Stargardt's ABCR is localized to the disc membrane of retinal rod outer segments. Nature Genetics. 17(1):15-6.

Thomas, P. M., Cote, G. J., Wohllk, N., Haddad, B., Mathew, P. M., Rabl, W., Aguilar-Bryan, L., Gagel, R. F., and Bryan, J. (1995). Mutations in the sulfonylurea receptor gene in familial persistent hyperinsulinemic hypoglycemia of infancy. Science 268, 426–429.

Valle, D. and Simell, O. (1995). The hyperornithinemias. In the Metabolic and Molecular Basis of Inherited Disease, Scriver, C. R., Beaudet, A. L., Sly, W. S., and Valle, D., eds. (New York: McGraw Hill), pp. 1147–1185.

van Helvoort, A., Smith, A. J., Spring, H., Fritzsche, I., Schinkel, A. H., Borst, P., and van Meer, G. (1996). MDR1 P-glycoprotein is a lipid translocase of broad specificity, while MDR3 P-glycoprotein specifically translocates phosphatidylcholine. Cell 87, 507–517.

Wang, Y., Macke, J. P., Abella, B. S., Andreasson, K., Worley, P., Gilbert, D. J., Copeland, N. G., Jenkins, N. A., and Nathans, J. (1996). A large family of putative transmembrane receptors homologous to the product of the Drosophilal tissue polarity gene frizzled. J. Biol. Chem. 271:4468–4476.

Warner, L. E., Hilz, M. J., Appel, S. H., Killian, J. M., Kolodny, E. H., Karpati, G., Carpenter, S., Watters, G. V., Wheeler, C., Witt, D., Bodell, A., Nelis, E., Van Broeckhoven, C., and Lupski, J. R. (1996). Clinical phenotypes of different MPZ ($P_0$) mutations may include Charcot-Marie-Tooth type 1B, Dejerine-Sottas, and congenital hypomyelination. Neuron 17, 451–460.

Weber, B. H. F., Vogt, G., Pruett, R. C., Stohr, H., and Felbor, U. (1994). Mutations in the tissue inhibitor of metalloproteinase-3 (TIMP3) in patients with Sorsby's fundus dystrophy. Nat. Genet. 8, 352–356.

Weiter, J. J., Delori, F. C., Wing, G. L., and Fitch, K. A. (1986). Retinal pigment epithelial lipofuscin and melanin and choroidal melanin in human eyes. Invest. Ophthalmol. Vis. Sci. 27, 145–152.

White, M. B., Carvalho, M., Derse, D., O'Brien, S. J., and Dean, M. (1992). Detecting single base substitutions as heteroduplex polymorphisms. Genomics 12, 301–306.

Wing, G. L., Blanchard, G. C., and Weiter, J. J. (1978). The topography and age relationship of lipofuscin concentration in the retinal pigment epithelium. Invest. Ophthalmol. Vis. Sci. 17, 601–607.

Zhang, K., Bither, P. P., Park, R., Donoso, L. A., Seidman, J. G., and Seidman, C. E. (1994). A dominant Stargardt's macular dystrophy locus maps to chromosome 13q34. Arch. Ophthalmol. 112, 759–764.

Zhou, H., Yoshioka, T., and Nathans, J. (1996). Retina-derived POU-domain factor-1: a complex POU-domain gene implicated in the development of retinal ganglion and amacrine cells. J. Neurosci. 16, 2261–2274.

Zinn, K. M. and Marmor, M. F. (1979). The Retinal Pigment Epithelium. (Harvard University Press, Cambridge, Mass.) pp 521.

What is claimed is:

1. A purified nucleic acid molecule comprising a sequence encoding a retina-specific ATP binding cassette transporter, wherein said retina-specific ATP binding cassette transporter comprises an amino acid sequence selected from the group consisting of SEQ ID NO:3 and SEQ ID NO:6.

2. A purified nucleic acid molecule comprising the sequence of SEQ ID NO:1.

3. A purified nucleic acid molecule comprising a sequence selected from the group consisting of SEQ ID NO:2 and SEQ ID NO:5.

4. An expression vector comprising a nucleic acid sequence encoding a retina-specific ATP binding cassette transporter, wherein said retina-specific ATP binding cassette transporter comprises an amino acid sequence selected from the group consisting of SEQ ID NO:3 and SEQ ID NO:6.

5. An expression vector comprising a nucleic acid sequence selected from the group consisting of SEQ ID NO:1, SEQ ID NO:2, and SEQ ID NO:5.

6. The expression vector of claim 4 wherein said nucleic acid sequence encodes the amino acid sequence of SEQ ID NO:3.

7. A host cell comprising an expression vector, wherein said expression vector comprises the nucleic acid sequence of SEQ ID NO:1.

8. A host cell comprising an expression vector, wherein said expression vector comprises a nucleic acid sequence selected from the group consisting of SEQ ID NO:2 and SEQ ID NO:5.

9. A host cell comprising an expression vector, wherein said expression vector comprises a nucleic acid sequence encoding an amino acid sequence selected from the group consisting of SEQ ID NO:3 and SEQ ID NO:6.

10. The host cell of claim 9, wherein said amino acid sequence comprises SEQ ID NO:3.

11. A cell culture comprising a culture of cells wherein at least one of said cells comprises an expression vector comprising a nucleic acid molecule encoding a retina-specific ATP binding cassette transporter, wherein said retina-specific ATP binding cassette transporter comprises an amino acid sequence selected from the group consisting of SEQ ID NO:3 and SEQ ID NO:6.

12. A cell culture comprising a culture of cells wherein at least one of said cells comprises an expression vector comprising a nucleic acid molecule comprising SEQ ID NO:1.

13. A cell culture comprising a culture of cells wherein at least one of said cells comprises an expression vector comprising a nucleic acid molecule selected from the group consisting of SEQ ID NO:2 and SEQ ID NO:5.

14. A nucleic acid molecule comprising a nucleic acid sequence identical to SEQ ID NO:2 except wherein said nucleic acid sequence comprises at least one mutation selected from the group consisting of 0223T→ G, 0634C→ T, 0746A→ G, 1018T→ G, 1411G→ A, 1569T→ G, 1715G→ A, 1715G→ C, 1804C→ T, 1822T→ A, 1917C→ A, 2453G→ A, 2461T→ A, 2536G→ C, 2588G→ C, 2791G→ A, 2827C→ T, 2894A→ G, 3083C→ T, 3212C→ T, 3215T→ C, 3259G→ A, 3322C→ T, 3364G→ A, 3385G→ T, 3386G→ T, 3602T→ G, 3610G→ A, 4139C→ T, 4195G→ A, 4222T→ C, 4297G→ A, 4316G→ A, 4319T→ C, 4346G→ A, 4462T→ C, 4469G→ A, 4577C→ T, 4594G→ A, 5041del15, 5281del9, 5459G→ C, 5512C→ T, 5527C→ T, 5657G→ A, 5693G→ A, 5882G→ A, 5908C→ T, 5929G→ A, 6079C→ T, 6088C→ T, 6089G→ A, 6112C→ T, 6148G→ C, 6166A→ T, 6229C→ T, 6286G→ A, 6316C→ T, 6391G→ A, 6415C→ T, 6445C→ T, 6543del36, 0664del13, 2884delC, 4232insTATG, 4947delC, 6709delG, 4253+5G→ T, 5196+2T→ C, 5585+1G→ A, 5714+5G→ A, 5898+1G→ A, and 6005+1G→ T.

15. The nucleic acid molecule of claim 14 wherein said mutation results in a frame shift.

16. The mucleic acid molecule of claim 14 wherein said mutation results in a splice site.

17. A purified nucleic acid molecule comprising a sequence encoding a retina-specific ATP binding cassette transporter comprising a sequence selected from the group consisting of SEQ ID NO:1, SEQ ID NO:2 and SEQ ID NO:5.

18. A purified nucleic acid molecule comprising a sequence selected from the group consisting of SEQ ID NO:1, SEQ ID NO:2, SEQ ID NO:4, and SEQ ID NO:5.

* * * * *

UNITED STATES PATENT AND TRADEMARK OFFICE
CERTIFICATE OF CORRECTION

PATENT NO.    : 6,713,300 B1
DATED         : March 30, 2004
INVENTOR(S)   : Rando Allikmets et al.

It is certified that error appears in the above-identified patent and that said Letters Patent is hereby corrected as shown below:

Title Page,
Item [73], Assignees, delete "by the Department of Health and Human Services, Washington, DC (US)" and insert -- by the Secretary of the Department of Health and Human Services, c/o National Institute of Health, Rockville, MD (US) --;
Item [56] References Cited, OTHER PUBLICATIONS,
The third "Allikmets, R. et al.," reference, delete "an dmapping" and insert -- and mapping --;
"Mosser, J. et al.," reference, delete "adrenoleukodysrophy" and insert --adrenoleukodystrophy --;
"Nickells, R.W. et al.," reference, delete "*Investigation*" and insert -- *Investigative* --;
"Stone, E.M. et al.," reference, delete "Stagardt-Like" and insert -- Stargardt-Like --;
"Warner, L.E. et al.," reference, delete "Clinincal" and insert -- Clinical --;
"Wu, D.Y. et al.," reference, delete "Reation" and insert -- Reaction --;
"Gerber, S. et al.," reference, delete "Statrgardt" and insert -- Stargardt --;

Column 1,
Line 8, delete "benefits" and insert -- benefit --;

Column 2,
Lines 12-13, delete "eta l.," and insert -- et al., --;

Column 3,
Line 55, delete "AGCR)" and insert -- ABCR) --;
Line 59, delete "Thee" and insert -- The --;

Column 4,
Line 4, delete "RNA" and insert -- RNAs --;
Line 48, delete "antisensr" and insert -- antisense --;

Column 5,
Line 13, delete "theory of" and insert -- theory or --;
Line 23, delete "within in" and insert -- within --;
Line 59, delete "lipfuscin-like" and insert -- lipofuscin-like --;
Line 61, delete "are mot" and insert -- are not --;

Column 6,
Line 44, delete "degenerative." and insert -- degeneration. --;

UNITED STATES PATENT AND TRADEMARK OFFICE
CERTIFICATE OF CORRECTION

PATENT NO. : 6,713,300 B1
DATED : March 30, 2004
INVENTOR(S) : Rando Allikmets et al.

It is certified that error appears in the above-identified patent and that said Letters Patent is hereby corrected as shown below:

Column 7,
Lines 25-26, delete "comprising" and insert -- comparing --;
Line 33, delete "provides" and insert -- protein --;
Line 56, delete "Also," and insert -- Alto, --;

Column 8,
Line 4, delete "the" and insert -- and --;
Line 11, delete "*marcesens*," and insert -- *marcescens*, --;

Column 9,
Line 52, delete "viral-medicated" insert -- viral-mediated --;

Column 10,
Lines 24-25, delete "*Tetracarbinomas*" and insert -- *Teratocarcinomas* --;

Column 11,
Line 35, delete "or retinal" and insert -- of retinal —;

Column 12,
Line 27, delete "specified" and insert -- specific --;

Column 14,
Line 26, delete " "Klenox" " and insert -- "Klenow" --;
Line 49, delete "86:57673-5677)," and insert -- 86:5673-5677), --;

Column 15,
Line 15, delete "vary" and insert -- varying --;
Line 39, delete "strain" and insert -- stain --;
Line 46, delete "Filbert," and insert -- Gilbert, --;

Column 16,
Line 6, delete "administration" and insert -- administered --;
Line 20, delete "be";

Column 17,
Line 50, delete "(Choezynski" and insert -- (Chomczynski --;
Line 51, delete "1987and" and insert -- 1987) and --;

UNITED STATES PATENT AND TRADEMARK OFFICE
CERTIFICATE OF CORRECTION

PATENT NO. : 6,713,300 B1
DATED : March 30, 2004
INVENTOR(S) : Rando Allikmets et al.

It is certified that error appears in the above-identified patent and that said Letters Patent is hereby corrected as shown below:

Column 18,
Line 61, delete "(Application" and insert -- (Applied --;

Column 20,
Line 32, delete "70°C." and insert -- 72° C. --;
Line 35, delete "90° C." and insert -- 94° C. --;
Line 65, delete "bending" and insert -- binding --;

Column 22,
Line 32, delete "controls 9440" and insert -- controls (440 --;
Line 63, Table 2, column 2, delete "RS72Q" and insert -- R572Q --;
Line 66, Table 2, column 2, delete "F6081" and insert -- F608I --;

Column 27,
Line 30, delete "97:832-992." and insert -- 97:983-992. --;

Column 29,
Line 34, delete "Spring," and insert -- Sprong, --;

Column 134,
Line 56, delete "mucleic" and insert -- nucleic --;

Signed and Sealed this

Ninth Day of November, 2004

JON W. DUDAS
*Director of the United States Patent and Trademark Office*